United States Patent
Gustafsson et al.

(10) Patent No.: US 6,617,320 B2
(45) Date of Patent: Sep. 9, 2003

(54) AMINO ACID DERIVATIVES

(75) Inventors: David Gustafsson, Kullavik (SE); Jan-Erik Nyström, Lindome (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/995,564

(22) Filed: Nov. 29, 2001

(65) Prior Publication Data

US 2002/0042396 A1 Apr. 11, 2002

Related U.S. Application Data

(60) Continuation of application No. 09/537,344, filed on Mar. 29, 2000, now Pat. No. 6,337,343, which is a division of application No. 08/687,466, filed as application No. PCT/SE96/00878 on Jul. 2, 1996, now Pat. No. 6,051,568.

(30) Foreign Application Priority Data

| Jul. 6, 1995 | (SE) | 9502487 |
|---|---|---|
| Jul. 7, 1995 | (SE) | 9502504 |
| Jul. 7, 1995 | (SE) | 9502505 |
| Nov. 7, 1995 | (SE) | 9503923 |
| Dec. 5, 1995 | (SE) | 9504349 |
| Dec. 22, 1995 | (GB) | 9526411 |

(51) Int. Cl.$^7$ ............... A61K 31/397; C07D 205/04
(52) U.S. Cl. ............... 514/210.17; 548/953
(58) Field of Search ............ 548/953; 514/210.17

(56) References Cited

U.S. PATENT DOCUMENTS

| 4,346,078 A | 8/1982 | Bajusz et al. |
|---|---|---|
| 5,561,146 A | 10/1996 | Kim et al. |
| 5,583,146 A | 12/1996 | Kimball et al. |
| 5,614,499 A | 3/1997 | Bylund et al. |
| 5,629,324 A | 5/1997 | Vacca et al. |
| 5,705,487 A | 1/1998 | Schacht et al. |
| 5,707,966 A | 1/1998 | Schacht et al. |
| 5,710,130 A | 1/1998 | Schacht et al. |
| 5,723,444 A | 3/1998 | Antonsson et al. |
| 5,726,159 A | 3/1998 | Schacht et al. |
| 5,741,792 A | 4/1998 | Kimball et al. |
| 5,741,799 A | 4/1998 | Kimball et al. |
| 5,744,487 A | 4/1998 | Ohshima et al. |
| 5,780,631 A | 7/1998 | Antonsson et al. |
| 5,783,563 A | 7/1998 | Antonsson et al. |
| 6,255,301 B1 | 7/2001 | Gustafsson et al. |

FOREIGN PATENT DOCUMENTS

| EP | 0 185 390 A2 | 6/1986 |
|---|---|---|
| EP | 0 195 212 A2 | 9/1986 |
| EP | 0 293 881 A2 | 12/1988 |
| EP | 0 362 002 A1 | 4/1990 |
| EP | 0 364 344 A2 | 4/1990 |
| EP | 0 364 344 A3 | 4/1990 |
| EP | 0 468 231 A2 | 1/1991 |
| EP | 0 468 231 A3 | 1/1992 |
| EP | 0 526 877 A3 | 2/1993 |
| EP | 0 526 877 A2 | 2/1993 |
| EP | 0 530 167 A1 | 3/1993 |
| EP | 0 542 525 A2 | 5/1993 |
| EP | 0 559 046 A1 | 9/1993 |
| EP | 0 601 459 A2 | 6/1994 |
| EP | 0 641 779 A1 | 3/1995 |
| EP | 0 648 780 A1 | 4/1995 |
| EP | 0 669 317 A1 | 8/1995 |
| EP | 0 686 642 A2 | 12/1995 |
| WO | WO 93/11152 A1 | 6/1993 |
| WO | WO 93/18060 A1 | 9/1993 |
| WO | WO 94/29336 | 12/1994 |
| WO | WO 95/01168 | 1/1995 |
| WO | WO 95/23609 | 9/1995 |
| WO | WO 95/35309 | 12/1995 |
| WO | WO 96/03374 A1 | 2/1996 |
| WO | WO 96/25426 | 8/1996 |
| WO | WO 96/32110 A1 | 10/1996 |

OTHER PUBLICATIONS

G. Claeson; "Synthetic peptides and peptidomimetics as substrates and inhibitors of thrombin and other proteases in the blood coagulation system"; Blood Coagulation and Fibrinolysis, 5, pp. 411–436 (1994).
B. Blomback et al; "Synthetic Peptides with Anticoagulant and Vasodilating Activity"; Scand. J. Clin. Lab. Invest. Suppl. 107, (1969) pp. 59–64.
D. Labes et al; "Hansch–Analyse der Hemmwirkung von 3– und 4–substituierten Benzamidinen gegenuber Thrombin, Plasmin and Trypsin"; Pharmazie, vol. 34, No. 10 (1979) pp. 649–653.
F. Markwardt et al; "Synthetic Low Molecular Weight Inhibitors of Serum Kallikrein"; Biochemical Pharmacology, vol. 23, (1974) pp. 2247–2256.
G. Claeson. "Synthetic peptides and peptidomimetics . . . " Blood Coagulation & Fibrinolysis, 5, pp. 411–436 (1994).
B. Blomback et al. "Synthetic peptides with anticoagulant and Vasodilating . . . " Scand. J. Clin. Lab. Invest. Suppl 107, (1969), pp. 59–64.
Labes et al, "Hansch–Analyse der Hemmwirkung von 3 und 4–substituierten Benzamidinen gegenuber Thrombin, Plasmin and Trypsin," Pharmazie, vol. 34, No. 10 (1979).
Markwardt et al, "Synthetic Low Molecular Weight Inhibitors of Serum Kallikrein," Biochemical Pharmacology, vol. 23, pp. 2247–2256 (1974).

Primary Examiner—Joseph K. McKane
Assistant Examiner—Golam M M Shameem
(74) Attorney, Agent, or Firm—Nixon & Vanderhye

(57) ABSTRACT

There is provided amino acid derivatives of formula I,

I

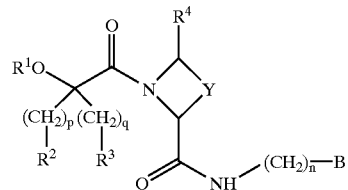

wherein p, q, $R^1$, $R^2$, $R^3$, $R^4$, Y, n and B have meanings given in the description which are useful as competitive inhibitors of trypsin-like proteases, such as hirombin, and in particular in the treatment of conditions where inhibition of thrombin is required (e.g. thrombosis) or as anticoagulants.

19 Claims, No Drawings

AMINO ACID DERIVATIVES

This application is a continuation-in-part of application Ser. No. 09/537,344, filed Mar. 29, 2000, now U.S. Pat. No. 6,337,343 which is a divisional of Ser. No. 08/687,466 filed Aug. 7, 1996, now U.S. Pat. No. 6,051,568, which is a 371 of PCT/SE96/00878 filed Jul. 2, 1996, the entire content of which is hereby incorporated by reference in this application.

FIELD OF THE INVENTION

This invention relates to novel pharmaceutically useful compounds, in particular competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel or in the heart, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would therefore be expected to exhibit antithrombotic activity. In addition, antithrombotic activity would be expected to be enhanced by effective inhibition of the positive feedback mechanism.

PRIOR ART

The development of low molecular weight inhibitors of thrombin has been described by Claesson in Blood Coagul. Fibrinol. (1994) 5, 411.

Blombäck et al. (*J. Clin. Lab. Invest* 24, suppl. 107, 59, (1969)) reported thrombin inhibitors based on the amino acid sequence situated around the cleavage site for the fibrinogen Aα chain. Of the amino acid sequences discussed, these authors suggested the sequence Phe-Val-Arg (P9-2-P1, hereinafter referred to as the P3-P2-P1 sequence) would be the most effective inhibitor (for a classification of substrate specificity see Schechten and Bergen, Biophys. Res. Commun. (1967) 27, 157 and (1968) 32, 898).

Thrombin inhibitors based on dipeptidyl derivatives with an α,ω-aminoalkyl guanidine in the P1-position are known from U.S. Pat. No 4,346,078 and International Patent Application WO 93/11152. Similar, structurally related, dipeptidyl derivatives have also been reported. For example International Patent Application WO 94/29336 discloses compounds with, for example, aminomethyl bennamidines, cyclic aminoalkyl amidines and cyclic aminoalkyl guanidines in the P1-position; European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidinopiperidine) in the P1-position, are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylaride ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on tripeptidyl derivatives have been disclosed in European Patent Applications 0 669 317, 0 686 642 and 0 648 780 and International Patent Applications WO 95/35309, WO 95/23609 and WO 94/29336.

However, there remains a need for effective inhibitors of trypsin-like serine proteases, such as thrombin. There is a particular need for compounds which are both orally bio-available and selective in inhibiting thiombin over other serine proteases. Compounds which exhibit competitive inhibitory activity towards thrombin would be expected to be especially useful as anticoagulants and therefore useful in the therapeutic treatment of thrombosis and related disorders.

DISCLOSURE OF THE INVENTION

According to the invention there is provided a compound of formula I,

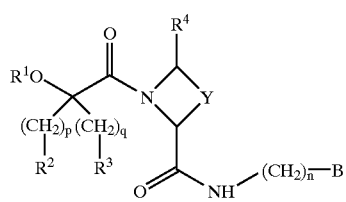

wherein p and q independently represent 0, 1, 2, 3 or 4;

$R^1$ represents H, 2,3-epoxypropyl, $C_{1-6}$ alkyl (which latter group is optionally substituted or terminated by one or more hydroxy group), a structural fragment of formula Ia

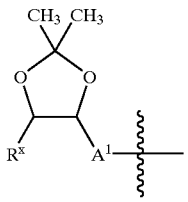

wherein $A^1$ represents a single bond or $C_{1-4}$ alkylene and $R^x$ represents H or $C_{1-4}$ alkyl, provided that there are no more than six carbon atoms in the chain $R^x$—C—C—$A^1$, or, when p represents 0, together with $R^2$ represents a structural fragment of formula Ib,

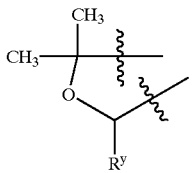

wherein $R^y$ represents H or $C_{1-3}$ alkyl;

$R^2$ represents H, Si(Me)$_3$, naphthyl, indolyl, CHR$^{21}$R$^{22}$ or $C_{1-4}$ alkyl (which latter group is optionally substituted or terminated by one or more fluorine or hydroxy group) or $C_{3-8}$ cycloalkyl or phenyl (which latter two groups are optionally substituted by one or more of $C_{1-4}$ alkyl, $C_{1-4}$ alkoxy, halo, hydroxy, cyano, nitro, methylenedioxy, trifluoromethyl, N(H)R$^{23}$, C(O)OR$^{24}$), or, when p represents 0, together with $R^1$ represents a structural fragment of formula Ib;

$R^3$ represents H, Si(Me)$_3$, naphthyl, indolyl, CHR$^{25}$R$^{26}$ or $C_{1-6}$ alkyl (which latter group) is optionally substituted or terminated by one or more fluorine or hydroxy group) or $C_{3-8}$ cycloalkyl or phenyl (which latter two groups are optionally substituted by one or more of $C_{1-4}$ allyl, $C_{1-4}$ alkoxy, halo, hydroxy, cyano, nitro, methylenedioxy, trifluoromethyl, N(H)R$^{27}$ or C(O)OR$^{28}$);

$R^{21}$, $R^{22}$, $R^{25}$ and $R^{26}$ independently represent cyclohexyl or phenyl;

$R^{23}$ and $R^{27}$ independently represent H, $C_{1-4}$ alkyl or C(O)R$^{29}$;

$R^{24}$, $R^{28}$ and $R^{29}$ independently represent H or $C_{1-4}$ alkyl;

$R^4$ represents H or $C_{1-4}$ alkyl;

Y represents $C_{1-3}$ alkylene optionally substituted by $C_{1-4}$ alkyl, hydroxy, methylene or oxo;

n represents 0, 1, 2, 3 or 4; and

B represents a structural fragment of formula IVa, IVb or IVc

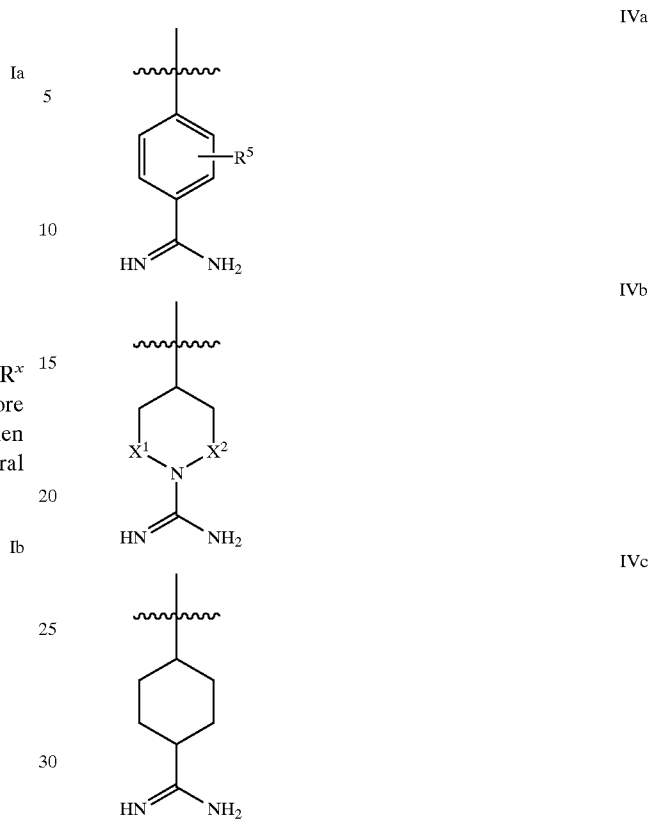

wherein
$R^5$ represents H, halo or $C_{1-4}$ alkyl; and
$X^1$ and $X^2$ independently represent a single bond or CH$_2$;
provided that when $R^1$, $R^2$ and $R^4$ all represent H, p represents 0, Y represents (CH$_2$)$_2$, n represents 1 and:
(a) $R^3$ represents unsubstituted phenyl and:
(i) B represents a structural fragment of formula IVa and $R^5$ represents H, then q does not represent 0 or 1; and
(ii) B represents a structural fragment of formula IVb and $X^1$ and $X^2$ both represent CH$_2$, then q does not represent 0; and
(b) $R^3$ represents unsubstituted cyclohexyl, B represents a structural fragment of formula IVa and $R^5$ represents H, then q does not represent 0;
or a pharmaceutically acceptable salt thereof (hereinafter referred to as "the compounds of the invention").

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. factional crystallisation or HPLC, techniques. Alternatively the desired optical isomers may be made by reaction of the appropriate optically active staring materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Alkyl groups which $R^1$, $R^x$, $R^y$, $R^2$, $R^3$, $R^4$, $R^5$, $R^{23}$, $R^{24}$, $R^{27}$, $R^{28}$ and $R^{29}$ may represent and which $R^2$, $R^3$ and Y may be substituted by; cycloallyl groups which $R^2$ and $R^3$ may represent; and alkoxy groups which $R^2$ and $R^3$ may be substituted by may be linear or branched, saturated or unsaturated. Alkylene groups which $A^1$ and Y may represent may be saturated or unsaturated.

Halo groups which $R^5$ may represent and which $R^2$ and $R^3$ may be substituted by include fluoro, chloro, bromo and iodo.

The wavy lines on the carbon atom in the fragments of formulae Ia, Ib, IVa, IVb and IVc signify the bond position of the fragment.

Abbreviations are listed at the end of this specification.

When B represents a structural fragment of formula IVa, IVc or IVb in which latter fragment $X^1$ and $X^2$ both represent $CH_2$, preferred compounds of the invention include those wherein n represents 1.

When B represents a structural fragment of formula IVb in which $X^1$ represents a single bond and $X^2$ represents either a single bond or $CH_2$, preferred compounds of the invention include those wherein n represents 2.

When B represents a structural fragment of formula IVa, preferred compounds of the invention include those wherein $R^5$ represents H.

Preferred compounds of formula I include those wherein:

$R^1$ represents H, methyl, 2,3-dihydroxypropyl or (2,2-dimethyl-1,3-dioxalan-4-yl)methyl;

p represents 0;

$R^2$ represents H, optionally substituted $C_{1-4}$ alkyl, or optionally substituted phenyl;

q represents 0, 1 or 2;

$R^3$ represents $C_{1-6}$ alkyl, naphthyl, indolyl, optionally substituted cyclohexyl or optionally substituted phenyl;

Y represents $CH_2$, $(CH_2)_2$, $(CH_2)_3$, $CH_2CH(CH_3)CH_2$, $CH_2C(=O)CH_2$ or $CH_2C(=CH_2)CH_2$;

$R^4$ represents H.

When $R^2$ represents $C_{1-4}$ alkyl, preferred optional substituents include hydroxy. Preferred points of attachment for the hydroxy group include the carbon atom which is a to the carbon atom to which $OR^1$ is attached.

More preferred compounds of the invention include those wherein:

$R^1$ represents H;

$R^2$ represents H, methyl, hydroxymethyl or ethyl;

q represents 0;

$R^3$ represents optionally substituted phenyl or optionally substituted cyclohexyl;

Y represents $CH_2$, $(CH_2)_2$ or $CH_2C(=CH_2)CH_2$;

When $R^1$ and $R^2$ both represent H, $R^3$ represents unsubstituted phenyl or unsubstituted cyclohexyl and q represents 0 or 1, preferred compounds of the invention include those wherein Y represents $CH_2$ or $CH_2C(=CH_2)CH_2$.

When $R^1$ represents H, $R^3$ represents unsubstituted phenyl or unsubstituted cyclohexyl and q represents 0 or 1, preferred compounds of the invention include those wherein $R^2$ represents methyl, hydroxymethyl or ethyl.

When $R^3$ represents cyclohexyl or phenyl, preferred optional substituents include hydroxy, fluoro, chloro, methyl, methoxy, amino, nitro, trifluoromethyl, methylenedioxy, ethoxy and propoxy. Particular substituents include hydroxy, mono- or difluoro, chloro, methyl, methoxy and methylenedioxy.

Particularly preferred compounds of the invention include those wherein

Y represents $CH_2$;

B represents a structural fragment of formula IVa.

Compounds of the invention in which the α-amino acid carbon in the fragment

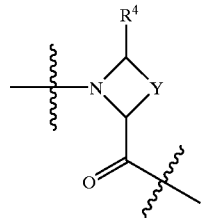

is in the S-configuration are preferred. The wavy lines on the nitrogen and carbon atom in the above fragment signify the bond position of the fragment.

When $R^1$ and $R^2$ both represent H and p represents 0, preferred compounds of the invention are those in which the carbon in the fragment.

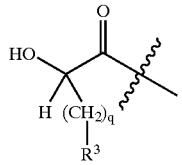

is in the R-configuration. The wavy line on the carbon atom in the above fragment signifies the bond position of the fragment.

Preferred compounds of the invention include:
Ch-(R,S)CH(OH)—C(O)-Aze-Pab;
Ch-(R)CH(OH)—C(O)-Aze-Pab;
Ph-(R)CH(OH)—C(O)-Aze-Pab;
Ph(3-Me)-(R,S)CH(OH)—C(O)-Aze-Pab;
Ph(3-OMe)-(R,S)CH(OH)—C(O)-Aze-Pab;
Ph(3,5-diOMe)-(R,S)CH(OH)—C(O)-Aze-Pab;
Ph(3-OMe,4-OH)—(R,S)CH(OH)—C(O)-Aze-Pab;
Ph-(R,S)C(Et)(OH)—C(O)-Aze-Pab;
Ph-(R,S)C(Et)(OH)—C(O)-Pro-Pab;
$(Ph)_2$C(OH)—C(O)-Aze-Pab;
Ph(3-OMe,4-OH)—(R,S)CH(OH)—C(O)-Pro-Pab;
Ph-(R)CH(OH)—C(O)-Aze-Pac;
Ph-(R)CH(OH)—C(O)—(R,S)Pic(cis-4-Me)-Pab;
Ph(3,4-(—O—$CH_2$—O—))—(R,S)CH(OH)—C(O)-Aze-Pab;
Ph(3-OMe)-(R,S)CH(OH)—C(O)-Pro-Pab;
Ph(3,5-diOMe)-(R,S)CH(OH)—C(O)-Pro-Pab;
Ph-(R,S)C(Me)(OH)—C(O)-Aze-Pab;
Ph(3,5-diMe)-(R,S)CH(OH)—C(O)-Aze-Pab;
Ph(3-$NH_2$)—(R,S)CH(OH)—C(O)-Aze-Pab;
Ph(3-$NH_2$)—(R,S)CH(OH)—C(O)-Pro-Pab;
Ph(3-$NO_2$)—(R,S)CH(OH)—C(O)-Pro-Pab;
Ph(3,4-(—O—$CH_2$—O—))—(R,S)CH(OH)—C(O)-Pro-Pab;
Ph(3,5-diF)-(R,S)CH(OH)—C(O)-Pro-Pab;
Ph-(R)CH(O—$CH_2$—(R,S)CH(—O—C($CH_3$)$_2$—O—$CH_2$—))—C(O)-Aze-Pab;
Ph-(R)C(Me)(OH)—C(O)-Pro-Pab;
Ph-(S)C(Me)(OH)—C(O)-Pro-Pab;
Ph-(3,4-diF)-(R,S)CH(OH)—C(O)-Pro-Pab;
Ph-(R)CH(OH)—C(O)—(R,S)Pic(4-methylene)-Pab;

Ph(3-Cl)—(R,S)CH(OH)—C(O)-Aze-Pab;
Ph-(R,S)C(—O—C(CH$_3$)$_2$—O—CH$_2$—)—C(O)-Aze-Pab;
Ph-(R,S)C(—O—C(CH$_3$)$_2$—O—CH$_2$—)—C(O)-Pro-Pab;
Ph-(R,S)C(CH$_2$OH)(OH)—C(O)-Aze-Pab; and
Ph-(R,S)C(CH$_2$OH)(OH)—C(O)-Pro-Pab.

Preparation

According to the invention there is also provided a process for the preparation of compounds of formula I which comprises:

(a) the coupling of a compound of formula V,

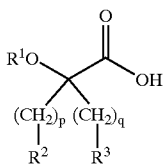

V wherein p, q, R$^1$, R$^2$ and R$^3$ are as hereinbefore defined with a compound of formula VI,

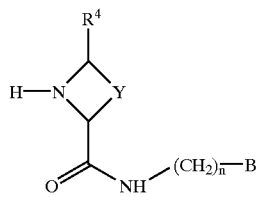

VI wherein R$^4$, Y, n and B are as hereinbefore defined; or (b) the coupling of a compound of formula VII,

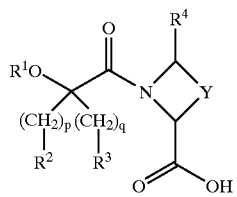

VII wherein p, q, R$^1$, R$^2$, R$^3$, R$^4$ and Y are as hereinbefore defined with a compound of formula VIII,

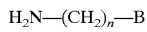 H$_2$N—(CH$_2$)$_n$—B    VIII wherein n and B are as hereinbefore defined;

for example in the presence of a coupling system (e.g. oxalyl chloride in DMF, EDC, DCC or TBTU), an appropriate base (e.g. pyridine, DMAP or DIPEA) and a suitable organic solvent (e.g. dichloromethane, acetonitrile or DMF).

Compounds of formula V are either commercially available, are well known in the literature, or are available using known techniques.

For example, compounds of formula V wherein R$^1$ and R$^2$ both represent H, p and q both represent 0 and R$^3$ represents naphthyl or phenyl optionally substituted by one or more of C$_{1-4}$ alkyl, C$_{1-4}$ alkoxy, halogen, hydroxy, cyano, methylenedioxy, nitro, trifluoromethyl, N(H)R$^{27}$ or C(O)OR$^{28}$ may be prepared by reaction of an aldehyde of formula IX,

 R$^{3a}$CHO    IX wherein R$^{3a}$ represents naphthyl or phenyl optionally substituted by one or more of C$_{1-4}$ ally, C$_{1-4}$ alkoxy, halogen, hydroxy, cyano, methylenedioxy, nitro, trifluoromethyl, N(H)R$^{27}$ or C(O)OR$^{28}$ and R$^{27}$ and R$^{28}$ are as hereinbefore defined, with:

(i) a compound of formula X,

 R"CN    X wherein R" represents H or (CH$_3$)$_3$Si, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis in the presence of an appropriate base (e.g. NaOH);

(ii) chloroform, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis in the presence of an appropriate base (e.g. NaOH);

(iii) a compound of formula XI,

XI wherein M represents Mg or Li, followed by oxidative cleavage (e.g. ozonolysis or osmium or ruthenium catalysed) under conditions which are well known to those skilled in the art; or iv) tris(methylthio)methane under conditions which are well known to those skilled in the art, followed by hydrolysis in the presence of an appropriate base.

Compounds of formula V wherein R$^1$ represents H, R$^2$ represents CH$_2$OH, p and q both represent 0 and R$^3$ represents naphthyl or phenyl optionally substituted by one or more of C$_{1-4}$ alkyl, C$_{1-4}$ alkoxy, halogen, hydroxy, cyano, methylenedioxy, nitro, trifluoromethyl, N(H)R$^{27}$ or C(O)OR$^{28}$ may be prepared by reaction of a compound of formula XII,

 R$^{3a}$C(O)C$_2$H$_5$    XII wherein R$^{3a}$ is as hereinbefore defined with sodium hypochlorite for example at room temperature in the presence of a suitable solvent (e.g. water).

Compounds of formula VI and VII are either commercially available, are well known in the literature, or are available using known techniques. For example compounds of formula VI may be made by standard peptide coupling of a compound of formula XIII,

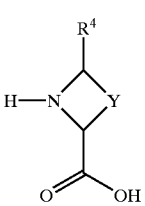

XIII wherein R$^4$ and Y are as hereinbefore defined with a compound of formula VIII as hereinbefore defined for example under conditions such as those described hereinbefore for synthesis of compounds of formula I. Similarly compound of formula VII may also be made by standard peptide coupling of a compound of formula XIII as hereinbefore defined with a compound of formula V as hereinbefore defined for example under conditions such as those described hereinbefore for synthesis of compounds of formula I.

Compounds of formula VIII, IX, X, XI, XII and XIII are either commercially available, are well known in the literature, or are available using known techniques. Substituents on the phenyl group in compounds of formula V, VII, IX and XII may be interconverted by techniques well known to those skilled in the art.

The compounds of the invention may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino, amidino, guanidino and carboxylic acid. Suitable protecting groups for hydroxy include trialkylsilyl and diarylalkylsilyl groups (e.g. tertbutyldimethylsilyl, tertbutyldiphenylsilyl or trimethylsilyl) and tetrahydropyranyl. Suitable protecting groups for hydroxy groups, which groups are attached to adjacent carbon atoms include O,O'-isopropylidene. Suitable protecting groups for amino, amidino and guanidino include tertbutyloxycarboryl or benzyloxycarbonyl. Amidino and guanidino nitrogens may be either mono- or diprotected. Suitable protecting groups for carboxylic acid include $C_{1-6}$ alkyl or benzyl esters.

The protection and deprotection of functional groups may take place before or after coupling.

In particular, the compounds of the invention may be prepared by processes comprising the coupling of an N-acylated amino acid or an N-protected amino acid. When an N-protected amino acid is used the acyl group may be added after coupling and deprotection of the nitrogen atom may then be effected using standard methods theater.

Protecting groups may be removed in accordance with techniques which are well known to those skilled in the art and as described hereinafter.

Certain protected intermediates of formula I, in which the amidino and guanidino nitrogens in B are protected, and which may be made prior to a final deprotection stage to form compounds of the invention, are novel.

According to a further aspect of the invention there is provided a compound of formula XIV,

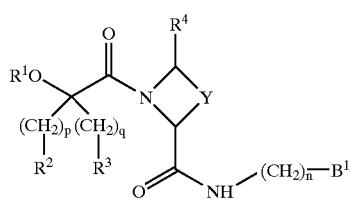

XIV wherein $B^1$ represents a structural fragment of formula IVd, IVe or IVf

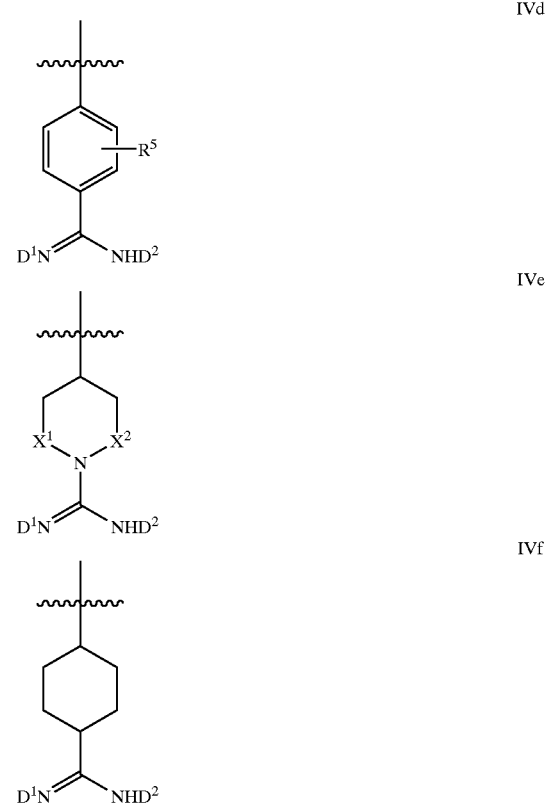

$D^1$ and $D^2$ independently represent H or benzyloxycarbonyl and p, q, $R^1$, $R^2$, $R^3$, $R^4$, Y, n, $R^5$, $X^1$ and $X^2$ are as hereinbefore defined, provided that $D^1$ and $D^2$ do not both represent H.

The wavy lines on the carbon atom in the fragments of formulae IVd, IVe or IVf signify the bond position of the fragment.

The use of protecting groups is fullly described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

It will also be appreciated by those skilled in the art that although such protected derivatives of compounds of formula I may not possess pharmacological activity as such, they may be administered parenterally or orally and thereafter metabolised in the body to form compounds of the invention which are pharmacologically active. Such derivatives may therefore be described as "prodrugs". All prodrugs of compounds of formula I are included within the scope of the invention.

Protected derivatives of compounds of formula I which are particularly useful as prodrugs include compounds of formula XIV.

Medical and Pharmaceutical Use

The compounds of the invention are useful because they possess pharmacological activity. They are therefore indicated as pharmaceuticals.

According to a further aspect of the invention there is thus provided the compounds of the invention for use as pharmaceuticals.

In particular, the compounds of the invention are potent inhibitors of thrombin, for example as demonstrated in the tests described below.

The compounds of the invention are thus expected to be usefull in those conditions where inhibition of thrombin is required.

The compounds of the invention are thus indicated in the treatment or prophylaxis of thrombosis and hypercoagulability in blood and tissues of animals including man.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the treatment of and/or prophylaxis of venous thrombosis and pulmonary embolism, arterial thrombosis (e.g. in myocardial infarction unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion (i.e. thrombosis) after thrombolysis, percutaneous trans-luminal angioplast (PTCA), coronary bypass operations, microsurgery and vascular surgery in general.

Further indications include the treatment and prophylaxis of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the present invention may also be useful for the treatment or prophylaxis of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous transluminal angioplasty (PTCA).

Compounds of the present invention that inhibit trypsin and/or thrombin may also be useful in the treatment of pancreatitis.

According to a further aspect of the invention, there is provided a method of treatment of a condition where inhibition of thrombin is required which method comprises administration of a therapeutically effective amount of a compound of formula I as defined above, or a pharmaceutically acceptable salt thereof, to a person suffering from, or susceptible to, such a condition.

Pharmaceutical Preparations

The compounds of the invention will normally be administered orally, subcutaneously buccally, rectally, dermally, nasally, tracheally, bronchially, by any other parenteral route or via inhalation, in the form of pharmaceutical preparations comprising the active ingredient either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors.

The compounds of the invention may further be combined with thrombolytics such as tissue plasminogen activator (natural or recombinant), streptokinase, urokinase, prourokinase, anisolated streptokinase plasminogen activator complex (ASPAC), animal salivary gland plasminogen activators, and the like, in the treatment of thrombotic diseases, in particular myocardial infarction.

According to a further aspect of the invention there is thus provided a pharmaceutical formulation including a compound of formula I as hereinbefore defined, or a pharmaceutically acceptable salt thereof, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

Biological Tests

Test A

Determination of Thrombin Clotting Time (TT)

Human thrombin (T 6769, Sigma Chem Co) in buffer solution, pH 7.4, 100 µl, and inhibitor solution, 100 µl, were incubated for one min. Pooled normal citrated human plasma, 100 µl, was then added and the clotting time measured in an automatic device (KC 10, Amelung).

The clotting time in seconds was plotted against the inhibitor concentration, and the $IC_{50}TT$ was determined by interpolation.

$IC_{50}TT$ is the concentration of inhibitor that doubles the thrombin clotting time for human plasma.

Test B

Determination of Activated Partial Thromboplastin Time (APTT)

APTT was determined in pooled normal human citrated plasma with the reagent PTT Automated 5 manufactured by Stago. The inhibitors were added to the plasma (10 µl inhibitor solution to 90 µl plasma) followed by the reagent and calcium chloride solution and APTT was determined in the mixture by use of the coagulation analyser KC10 (Amelung) according to the instructions of the reagent producer. The clotting time in seconds was plotted against the inhibitor concentration in plasma and the $IC_{50}APTT$ was determined by interpolation.

$IC_{50}APTT$ is defined as the concentration of inhibitor in human plasma that doubled the Activated Partial Thromboplastin Time.

Test C

Determination of Thrombin Time Ex Vivo

The inhibition of thrombin after oral or parenteral administration of the compounds of the invention were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L) and 9 parts of blood.

The tubes were centrifged to obtain platelet poor plasma The plasma was used for determination of thrombin time as described below.

The citrated rat plasma, 100 μl, was diluted with a saline solution, 0.9%, 100 μl, and plasma coagulation was started by the addition of human thrombin (T 6769, Sigma Chem Co, USA) in a buffer solution, pH 7.4, 100 μl. The clotting time was measured in an automatic device (KC 10, Amelumg, Germany).

Where a compound of formula XIV was administered, concentrations of the appropriate active thrombin inhibitor of formula I in the rat plasma were estimated by the use of standard curves relating the thrombin time in the pooled citrated rat plasma to known concentrations of the corresponding "active" thrombin inhibitor dissolved in saline.

Test D

Determination of Thrombin Time in Urine Ex Vivo

Conscious rats were placed in metabolism cages for 24 hours following oral administration of compounds of the invention. The thrombin time was determined on the collected urine as described below.

Pooled normal citrated human plasma (100 μL) was incubated with the concentrated rat urine, or saline dilutions thereof, for one minute. Plasma coagulation was then initiated by the administration of human thrombin (T 6769, Sigma Chem Company) in buffer solution (pH 7.4; 100 μL). The clotting time was measured in an automatic device (KC 10; Amelung).

Where a compound of formula XIV was administered, concentrations of the appropriate active thrombin inhibitor of formula I in the rat urine were estimated by the use of standard curves relating the thrombin time in the pooled normal citrated human plasma to known concentrations of the corresponding "active" thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted could be calculated.

The invention is illustrated by way of the following examples.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS). $^1$H NMR and $^{13}$C NMR measurements were performed on BRUKER ACP 300 and Varian UNITY plus 400 and 500 spectrometers, operating at $^1$H frequencies of 300.13, 399.96 and 499.82 MHz respectively, and at $^{13}$C frequencies of 75.46, 100.58 and 125.69 Mhz respectively.

Example 1

Ch-(R,S)CH(OH)—C(O)-Aze-Pab×HCl (i) Boc-Aze-OH

Di-tert-butyl dicarbonate (13.75 g; 63 mmol) was added with stirring at room temperature to a mixture of 5.777 g (57 mmol) of L-azetidine-2caboxylic acid (H-Aze-OH) and 6.04 g (57 mmol) of sodium carbonate in 50 mL of water and 100 mL of THF. After 60 h the THF was removed in vacuo and the mixture was diluted with water and acidified with 2 M potassium hydrogen sulphate. Extraction with methylene chloride followed by drying (magnesium sulphate) and evaporation of the solvent gave a residue which was crystallized from methylene chloride:hexane to give 10.87 g (95%) of colourless crystals.

$^1$H-NMR (300 MHz; CDCl$_3$): δ4.85–4.7 (br s, 1), 4.0–3.75 (m, 2), 2.65–2.35 (m, 2), 1.4 (s, 9).

(ii) Bo-Aze-Pab(Z)

At room temperature, EDC (13.5 g; 70 mmol) was added to a mixture of Boc-Aze-OH (10.87 g; 54 mmol; from step (i) above), H-Pab(Z)×HCl (18.31 g; 57 mmol; prepared according to the method described in International Patent Application WO 94/29336) and DMAP (9.9 g; 81 mmol) in acetonitrile (270 mL). After 16 h the solvent was removed in vacuo and replaced by ethyl acetate. The mixture was washed with water and an aqueous solution of citric acid. The organic layer was dried (magnesium sulphate) and the solvent was removed in vacuo to give a residue which gave Boc-Aze-Pab(Z) (17.83 g) upon crystallization from a mixture of methylene chloride, toluene, diisopropyl ether and petroleum ether.

$^1$H-NMR (300 MHz; CDCl$_3$): δ7.85–7.75 (d, 1), 7.45–7.2 (m, 7), 5.2 (s, 2), 4.7 (t, 1), 4.6–4.4 (m, 2), 3.95–3.8 ("q", 1), 3.8–3.7 (q, 1), 2.5–2.3 (m, 2), 1.4 (s, 9).

(iii) H-Aze-Pab(Z)

Boc-Aze-Pab(Z) (2.44 g; 5.2 mmol; from step (ii) above) was dissolved in a mixture of 10 mL of trifluoroacetic acid and 10 mL of methylene chloride. After 30 minutes the solvent and trifluoroacetic acid were removed in vacua and the residue was dissolved in methylene chloride. The organic phase was washed with 10% sodium carbonate solution and dried (potassium carbonate). Removal of the solvent in vacuo gave a residue which gave H-Aze-Pab(Z) (1.095 g, 57%) as colourles crystals upon crystallization from methylene chloride.

$^1$H-NMR (300 MHz, CD$_3$OD): δ7.85–7.75 (d, 2), 7.45–7.25(m, 7), 5.2 (s, 2), 4.5 (s, 2), 4.3 (d, 1), 3.65 (q, 1), 3.4–3.3 (m, 1), 2.7–2.5 (m, 1), 2.4–2.2 (m, 1).

(iv) Ch-(R,S)CH(OH)—C(O)-Aze-Pab(Z)

Prepared in accordance with the method described by Kelly and LaCour (Synth. Comm. 22, 859 (1992)) in the following way. To a solution of (R,S)-hexahydromandelic acid (0.30 g, 1.9 mmol), a catalytic amount of DMAP, and pyridine (0.31 g, 3.9 mmol) in methylene chloride (5 mL) was added TMSCl (0.42 g; 3.9 mmol) dropwise. The reaction was stirred at room temperature for 4 h. The reaction was cooled to 0° C. and a catalytic amount of DMF (3 drops from a 2 mL syringe) was added followed by oxalyl chloride (0.25 g; 2.0 mmol). The reaction was stirred for 1 h at 0° C., a mixture of H-Aze-Pab(Z) (0.67 g; 1.8 mmol; from step (iii) above) and pyridine (0.50 g; 6.3 mmol) was added and the reaction was allowed to warm to room temperature and stirred over night. A 10% solution of citric acid in methanol (6 mL) was added to the reaction After 30 minutes, the reaction was poured into a separating funnel and diluted with 30 mL of ethyl acetate and the aqueous phase was exuded with ethyl acetate. The combined organic layers were washed with a saturated bicarbonate solution followed by brine and dried (Na$_2$SO$_4$). After evaporation and flash chromatography on silica gel using methylene chloride:methanol (99:1 to 92:8) as eluent the sub-title compound (60 mg; 6%) was obtained;

$^1$H-NMR (300 MHz; CDCl$_3$) δ1.0–1.9 (m, 11 H), 2.4–2.7 (m, 2 H), 3.80 (d, 1 H), 4.05–4.25 (m, 1 H), 4.3–4.5 (m, 2 H), 4.85–5.0 (m, 1 H), 5.18 (s, 2 H), 7.1–7.5 (m, 7 H), 7.65–7.8 (m, 2 H), 7.86 (bt, 1 H, minor diastereomer and/or rotamer), 8.33 (bt, 1 H, major diastereomer and/or rotamer)

$^{13}$C-NMR (75 MHz, CDCl$_3$) amidine and carbonyl carbons: δ174.8, 170.6, 168.0 and 164.5.

(v) Ch-(R,S)CH(OH)—C(O)-Aze-Pab×HCl

Ch-(R,S)CH(OH)—C(O)-Aze-Pab(Z) (60 mg; 0.12 mmol; from step (iv) above) was dissolved in ethanol (5 mL), and 5% Pd/C and HCl (0.1 mL; conc.) were added. The mixture was hydrogenated at atmospheric pressure for 2 hours. After filtration and evaporation the product was purified through preparative RPLC using (0.005 M NH$_4$OAc, 0.005 M HOAc):CH$_3$CN 4:1 as eluent. After freeze drying, HCl (aq) was added and the solution was freeze dried. The yield of the title product was 15 mg (31%).

$^1$H-NMR (300 MHz; D$_2$O) the spectrum was complicated due to diastereomers and/or rotamers): δ0.7–2.0 (m, 11 H), 2.25–2.4 (m, 1 H), 2.65–2.9 (m, 1 H), 3.79 (d, 1 H, minor), 4.03 (d, 1 H, major), 4.05–4.15 (m, 2 H, minor), 4.35–4.45 (m (bt), 2 H, major), 4.5–4.6 (m, 2 H), 5.20 (m, 1 H, minor, the major signal overlapping with the HOD signal), 7.5–7.65 (m, 2 H), 7.75–7.85 (m, 2 H).

$^{13}$C-NMR (75 MHz; CDCl$_3$) amidine and carbonyl carbons (diastreomers and/or rotamers): δ1763, 175.4, 173.7, 173.3, 167.2 and 167.0.

Example 2

Ch-(R)CH(OH)—C(O)-Aze-Pab×HCl 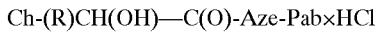

(i) Ch-(R)CH(OH)—C(O)-Aze-Pab(Z)

The sub-title compound was prepared according to the method described in Example 1(iv) (R)-hexahydromandelic acid (from 0.60 g; 3.8 mmol) yielding 0.15 g (10%).

(ii) Ch-(R)CH(OH)—C(O)-Aze-Pab×HCl

The title compound was prepared according to the method described in Example 1(v) from Ch-(R)CH(OH)—C(O)-Aze-Pab(Z) (0.12 g; 0.24 mmol; from step (i) above). Yield: 52 mg (54%).

$^1$H-NMR (300 MHz; D$_2$O; the spectrum was complicated due to rotamers): δ0.7–2.0 (m, 11 H), 2.25–2.4 (m, 1 H), 2.6–2.9 (m, 1 H), 3.79 (d, 1 H, minor), 4.02 (d, 1 H, major), 4.05–4.15 (m, 2 H, minor), 4.35–4.45 (m (bt), 2 H, major), 4.5–4.6 (m, 2 H), 5.19 (m, 1 H, minor, the major signal overlapping with the HOD signal), 7.5–7.65 (m, 2 H), 7.75–7.85 (m, 2 H).

$^{13}$C-NMR (75 MHz, CDCl$_3$) amidine and carbonyl carbons (rotamers): 171.9, 170.2, 169.8 and 163.8.

Example 3

(Et)$_2$C(OH)—C(O)-Aze-Pab×HCl 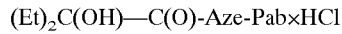

(i) H-Aze-Pab(Z)×2HCl

The subtitle compound was prepared by reaction of Boc-Aze-Pab(Z) (see Example 1(ii) above) with EtOAc staturated with gaseous HCl. The reaction mixture was evaporated after half an hour to give H-Aze-Pab(Z)×2HCl in a quantitative yield.

(ii) (Et)$_2$C(OH)—C(O)-Aze-Pab(Z)

A mixture of diethylglycolic acid (0.13 g; 0.80 mmol), H-Aze-Pab(Z)×2HCl (0.39 g; 0.88 mmol; from step (i) above), TBTU (0.28 g; 0.88 mmol) in DMF (15 mL) was cooled on an ice bath. DIPEA (0.41 g; 3.2 mmol), was added and the reaction mixture was stired at room temperature overnight. The resultant mixture was poured into 500 mL of water and extracted 3 times with ethyl acetate. The combined organic phase was washed with aqueous NaHCO$_3$ and water, dried (Na$_2$SO$_4$) and evaporated. The crude product was flash chromatographed on silica gel using methylene chloride:THF as eluent. Yield: 30 mg (8%).

$^1$H-NMR (400 MHz; CDCl$_3$): δ8.04 (bt, 1H), 7.77 (d, 2H), 7.40 (d, 2H), 7.35–7.2 (m, 5 H), 5.17 (s, 2H), 4.90 (m, 1 H), 4.46 (dd, 1 H), 4.39 (dd, 1 H), 4.3–4.2 (m, 2 H), 2.66 (m, 1 H), 2.44 (m, 1 H), 1.8–1.5 (m, 4 H), 0.9–4.75 (m, 6 H).

(iii) (Et)$_2$C(OH)—C(O)-Aze-Pab×HCl

The title compound was prepared according to the method described in Example 1(v) from (Et)$_2$C(OH)—C(O)-Aze-Pab(Z) (30 mg; 0.063 mmol; from step (ii) above). Yield: 19 mg (79%).

$^1$H-NMR (300 MHz; D$_2$O; the spectrum was complicated due to rotamers): δ7.80 (d, 2 H), 7.65–7.5 (m, 2 H), 5.43 (m, 1 H, minor rotamer) 4.90 (m, 1 H, major rotamer, 4.6–4.5 (m, 3 H), 4.11 (m, 1 H, rotamer), 3.70 (m, 1H, rotamer), 2.8–2.55 (m, 1 H), 2.35–2.15 (m, 1 H), 1.9–1.6 (m, 4 H), 1.0–0.75 (m, 6 H).

$^{13}$C-NMR (75 MHz; D$_2$O) amidine and carbonyl carbons (rotamers): δ178.3, 177.4, 175.0, 173.5, 167.2.

Example 4

(Ph)$_2$C(OH)—C(O)-Aze-Pab×HCl 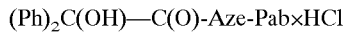

(i) (Ph)$_2$C(OH)—C(O)-Aze-Pab(Z)

The sub-title compound was prepared according to the method described in Example 3(ii) from benzilic acid (0.18 g; 0.80 mmol). Yield: 0.16 g (35%).

$^1$H-NMR (300 MHz; D$_2$O): δ7.93 (bt, 1 H), 7.71 (d, 2 H), 7.54–7.15 (m, 17 H), 5.14 (s, 2 H), 4.89 (m, 1 H), 4.57 (m, 1H), 4.48 (dd, 1 H), 4.35 (dd, 1 H), 3.60 (m, 1 H), 3.44 (m, 1 H), 2.44 (m, 1 H), 2.23 (m, 1 H).

(ii) (Ph)$_2$C(OH)—C(O)-Aze-Pab×HCl

The title compound was prepared according to the method described in Example 1(v) from (Ph)$_2$C(OH)—C(O)-Aze-Pab(Z) (0.16 g; 0.28 mmol; from step (i) above). Yield. 90 mg (68%).

$^1$H-NMR (400 MHz; D$_2$O) the spectrum was complicated due to rotamers: δ7.65–7.55 (m, 2 H), 7.4–7.1 (m, 12 H), 5.13 (m, 1 H, minor rotamer), 4.77 (m, 1 H, major rotamer), 4.43 (d, 1 H), 4.40 (d, 1 H), 4.12 (m, 1 H, major rotamer), 4.05–3.9 (m, 1 H, plus 1 H minor rotamer), 2.55 (m, 1 H, minor rotamer), 2.39 (m, 1 H, major rotamer), 2.08 (m, 1 H).

$^{13}$C-NMR (75 MHz, D$_2$O) amidine and carbonyl carbons (rotamers): δ175.7, 174.9, 174.6, 173.4, 167.1.

Example 5 n-C$_6$H$_{13}$—(R,S)CH(OH)—C(O)-Aze-Pab×HCl 

(i) n-C$_6$H$_{13}$—(R,S)CH(OH)—C(O)-Aze-Pab(Z)

The sub-title compound was prepared according to the method described in Example 3(ii) above from (R,S)-2-hydroxyoctanoic acid (0.13 g; 0.80 mmol yielding 0.25 g (61%).

$^1$H-NMR (400 MHz; CDCl$_3$): δ8.24 (bt, 1H, one diastereomer), 7.89 (bt, 1H, one diastereomer), 7.8–7.75 (n, 2H), 7.4–7.45 (m, 2H), 7.35–7.25 (m, 5 H), 5.18 (s, 2H), 4.95–4.85 (m, 1 H), 4.55–4.35 (m, 2 H), 4.2–4.0 (m, 3 H), 2.8–2.65 (m, 1 H), 2.6–2.4 (m, 1 H), 2.0–1.2 (m,10 H), 0.9–0.8 (m, 3 H).

(ii) n-C$_6$H$_{13}$—(R,S)CH(OH)—C(O)-Aze-Pab×HCl

The title compound was prepared according to the method described in Example 1(v) from n-C$_6$H$_{13}$—(R,S)CH(OH)—C(O)-Aze-Pab(Z) (0.14 g; 0.28 mmol; from step (i) above) yielding 88 mg (78%).

$^1$H-NMR (400 MHz; D$_2$O): δ7.7–7.6 (m, 2 H), 7.45–7.3 (m, 2 H), 5.03 (m, 1 H, one diastereomer) 4.74 (m, 1 H, one diastereomer overlapping with the water signal), 4.45–4.35 (m, 2 H), 4.3–4.1 (m, 2 H), 4.0–3.8 (m, 1H), 2.65–2.45 (m, 1 H), 2.3–2.1 (m, 1 H), 1.6–0.9 (m, 10 H), 0.75–0.65 (m, 3 H).

$^{13}$C-NMR (75 MHz; D$_2$O) amidine and carbonyl carbons (diasteomers and rotamers): δ176.8, 176.4, 176.0, 173.5, 173.3, 173.2, 167.2.

Example 6

Ph-(R)CH(OH)—C(O)-Aze-Pab(Z) 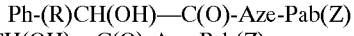

(i) Ph-(R)CH(OH)—C(O)-Aze-Pab(Z)

The sub-title compound was prepared according to the method described in Example 3(ii) from (R)-mandelic acid (0.12 g; 0.8 mmol). The crude product (0.315 g) was purified by flash chromatography (Si-gel; THF:EtOAc (6:4)). Yield 0.128 g (32%) of white powder, purity 91.2% (HPLC).

$^1$H-NMR (499.803 MHz, CDCl$_3$): δ8.14 (t, 1H), 7.72 (d, 2H, 7.42 (d, 2H), 7.33 (t, 4H), 7.28 (m, 3H), 7.22 (d, 2H), 5.18 (s, 2H), 4.92 (s, 1H), 4.79 (dd, 1H), 4.54 (broad s, 1H), 4.39 (d, 2H), 4.00 (q, 1H), 3.53 (q, 1H), 2.48 (m, 1H), 2.24 (m, 1H), 2.19 (broad s, 1H).

$^{13}$C-NMR (125.688 MHz; CDCl$_3$) (carboxylic and amidine carbons): δ173.1, 170.3, 168.1, 164.5.

(ii) Ph-(R)CH(OH)—C(O)-Aze-Pab

Ph-(R)CH(OH)—C(O)-Aze-Pab(Z) (107 mg, 0.214 mmol; from step (i) above) was dissolved in THF:water (2:1), 37 mg of Pd/C (4 mol % Pd) was added and the resulting solution was hydrogenated over 6 hours. The solution was filtrated through hyflo, and evaported to dryness. To the resulting white powder was added 20 mL of water acidified with 0.42 mL of 1M HCl (ca. 2 equivalents). The resulting solution was washed with 5 mL of EtOAc and 10 mL of diethyl ether, and freezered twice. Yield: 72 mg (84%) of white powder. Purity: 91% (HPLC).

$^1$H-NMR (399.968 MHz; D$_2$O): δ7.57 (t, 2H), 7.36 (d, 1H), 7.32 (s,3), 7.27 (s, 1H), 7.25 (d, 1H), 7.19 (m, 1H), 5.17 (s, 1H, major), 5.09 (s, 1H, minor), 5.00 (dd, 1, minor), 4.38 (s,2, major), 4.20 (dd, 1H, major), 3.98 (dd, 2H, minor), 3.97 (m, 1H, major), 3.75 (dd, 1H), 2.68 (s, 1H, minor), 2.65 (m, 1H, minor), 2.35 (m, 1H, major), 2.12 (m, 1H, major), 2.03 (m, 1H, minor).

$^{13}$C-NMR (111.581 MHz; D$_2$O) (carbonyl and amidine carbons): δ174.5, 173.2, 172.5, 172.4.

Example 7

Ph(4-CF$_3$)—(R,S)CH(OH)—C(O)-Aze-Pab×HCl (i) Ph(4CF$_3$)—(R,S)CH(OH)—C(O)-Aze-Pab(Z)

The sub-title compound was prepared according to method described in Example 3(ii) from (R,S)-4-tifluoromethylmandelic acid (0.19 g; 0.88 mmol). Flash chromatography (Si-gel, CH$_2$Cl$_2$:THF (6:4)) yielded 0.13 g (26%) of white powder.

$^1$H-NMR (300 MHz; CDCl$_3$): δ9.6–9.2 (b, 1H), 8.1 (bt, 1 H, diastereomer), 7.9 (bt, 1 H, diastereomer), 7.7–7.1 (m, 13 H), 5.16 (s, 2 H), 5.07 (s, 1 H, diastereomer), 4.98 (s, 1 H, diastereomer), 4.80 (m, 1 H), 4.5–4.2 (m, 2 H), 4.1–3.5 (m, 2 H), 2.5–2.2 (m, 2 H).

$^{13}$C-NMR (75 MHz; CDCl$_3$), amidine and carbonyl carbons (diastereomers): δ173.3, 172.4, 170.3, 168.3, 164.4

(ii) Ph-(4-CF$_3$)—(R,S)CH(OH)—C(O)-Aze-Pab×HCl

Prepared according to the method described in Example 1(v) from Ph(4CF$_3$)—(R,S)CH(OH)—C(O)-Aze-Pab(Z) (133 mg; 0.23 mmol; from step (i) above) to give the title compound as a white crystaline powder. Yield 77 mg (70%).

$^1$H-NMR (300 MHz; D$_2$O): δ8.84 (m, 1 H, diastereomer/rotamer), 8.73 (m, 1 H, diastereomer/rotamer), 8.52 (m, 1 H, diastereomer/rotamer), 7.8–7.4 (m, 8 H), 5.46, 5.44, 5.30, 5.20 (singlets, 1 H, diastereomers/rotamers), 4.96 (m, 1 H, diastereomer/rotamer, other signals from the same proton overlapping with the HDO-signal), 4.6–4.0 (m, 4 H), 2.9–2.5 (m, 1 H), 2.4–2.1 (m, 1 H).

$^{13}$C-NMR (75 MHz; D$_2$O), amidine and carbonyl carbons (diastermers and rotamers): δ173.6, 173.3, 173.1, 173.0, 172.9, 167.0.

Example 8

Ph-(4-OMe)-(R,S)CH(OH)—C(O)-Aze-Pab×HCl (i) Ph(4-OMe)-(R,S)CH(OH)—C(O)-Aze-Pab(Z)

The sub-title compound was prepared according to method 3(ii) from (R,S) 4-methoxymandelic acid (0.18 g; 1.0 mmol. Flash chromatography (Si-gel; EtOAc:MeOH (95:5)) yielded 27 mg (17%) of white powder.

Diastereomeric ratio 85:15; signals from the major diastereomer.

$^1$H-NMR (400 MHz; CDCl$_3$): δ8.19 (m, 1 H), 7.80 (d, 2 H), 7.45 (d, 2 H), 7.4–7.2 (m, 7 H), 7.13 (d, 2 H, minor rotamer), 6.90 (d, 2 H, major rotamer), 6.82 (d, 2 H, minor rotamer), 5.21 (s, 2 H), 4.9–4.85 (m, 2 H; thereof a singlet at 4.89 (1 H)), 4.6–4.4 (m, 2 H), 4.02 (m, 1 H), 3.81 (s, 3 H), 3.55 (m, 1 H), 2.62 (m, 1 H), 2.32 (m, 1 H).

$^{13}$C-NMR (100 MHz; CDCl$_3$) amidine and carbonyl carbons: δ173.6, 170.3, 167.8, 164.6.

(ii) Ph(4-OMe)-(R,S)CH(OH)—C(O)-Aze-Pab×HCl

The title compound was prepared according to method described in Example 1(v) from Ph(4OMe)-(R,S)CH (OH)—C(O)-Aze-Pab(Z) (27 mg; 0.05 mmol; from step (i) above). Yield 15 mg (68%) of white powder.

Diastereomeric ratio 85:15; signals from the major diastereomer $^1$H-NMR (400 MHz; D$_2$O): δ7.7–7.6 (m, 2 H), 7.5–7.3 (m, 4 H), 7.18 (d, 2 H, rotamer), 6.97 (d, 2 H, rotamer), 6.9–6.85 (m, 2 H, rotamer), 5.19 (s, 1 H, rotamer), 5.14 (s, 1 H, rotamer), 5.01 (m, 1 H, rotamer), 4.76 (m, 1 H rotamer), 4.48 (s, 1 H), 4.3–3.7 (m, 7 H, thereof 2 singlets at 3.78, 3.77 (3H)), 2.73 (m, 1 H, rotamer), 2.46 (m, 1 H, rotamer), 2.3–2.0 (m, 1 H).

$^{13}$C-NMR (75 MHz, D$_2$O), anidine and carbonyl carbons (rotamers): δ175.5, 174.1, 173.3, 173.1, 167.1, 167.0.

Example 9

Ph(4-OH)—(R,S)CH(OH)—C(O)-Aze-Pab×HCl (i) Ph(4-OH)—(R,S)CH(OH)—C(O)-Aze-Pab(Z)

The sub-title compound was prepared according to the method described in Example 3(ii) from (R,S)-4-hydroxymandelic acid (0.34 g; 2.0 mmol). Flash chromatography (Si-gel, EtOAc/EtOH 9/1) yielded 0.18 g (17%).

$^1$H-NMR (400 MHz; CDCl$_3$): δ7.70 (d, 2 H, minor diastereomer/rotamer), 7.64 (d, 2 H, major diastereomer/rotamer), 7.5–7.0 (m, 7 H), 6.82 (d, 2 H, major diastereomer/rotamer), 6.67 (d, 2 H, minor diastereomer/rotamer), 6.43 (d, 2 H, major diastereomer/rotamer), 5.30, 5.26, 5.22, 5.21 (singlets, 2 H, diastreomersrotamers), 4.95–4.8 (m, 2 H), 4.15–4.05 (m, 2 H), 4.0–3.7 (m, 2 H), 2.7–2.5, (m, 2 H).

(ii) Ph(4-OH)—(R,S)CH(OH)—C(O)-Aze-Pab×HCl

The sub-title compound was prepared according to the method described in Example 1(v) from Ph(4-OH)—(R,S) CH(OH)—C(O)-Aze-Pab(Z) (94 mg; 0.18 mmol; from step (i) above). Yield: 37 mg (49%) of white powder.

$^1$H-NMR (600 MHz; D$_2$O): δ7.76, 7.72, 7.71, 7.68, 7.52, 7.47, 7.40, 7.35, 7.25, 7.19, 7.11, 6.97, 6.82, 6.76, 6.73, 6.71 (doublets, 8 H, diastereomers/rotamers), 5.19 (s, 1 H, diastereomer/rotamer), 5.17 (s, 1 H, diastereomer/rotamer), 5.14 (s, 1 H, diastereomer/rotamer), 5.01 (m, 1 H diastereomer/rotamer), 4.88 (m, 1 H) diastereomer/rotamer, other signals from the same proton overlapping with the HDO-signal), 4.6–3.8 (m, 4 H), 2.77 (m, 1 H, diastereomer/rotamer), 2.62 (m, 1 H, diastereomer/rotamer), 2.49 (m, 1 H, diastereomer/rotamer), 2.3–2.1 (m, 1 H).

$^{13}$C-NMR (75 MHz; D$_2$O), amidine and carbonyl carbons (diastereomers and rotamers): δ175.9, 174.8, 174.3, 173.3, 173.2, 172.9, 167.1.

Example 10

Ph-CH$_2$—(R)CH(OH)—C(O)-Aze-Pab×HCl (i) Ph-CH$_2$—(R)CH(OH)—C(O)-Aze-Pab(Z)

The sub-title compound was prepared according to method described in Example 3(ii) from (R)-phenyllactic acid (0.25 g; 1.5 mmol. Flash chromatography (Si-gel, CH$_2$Cl$_2$:THF (6:4)) yielded 0.28 g (36%).

$^1$H-NMR (500 MHz; CDCl$_3$): δ8.19 (m, 1 H), 7.72 (d, 2 H), 7.43 (d, 2 H), 7.4–7.1 (m, 10 H), 5.19 (s, 2 H), 4.73 (m, 1 H), 4.45–4.25 (m, 2 H), 4.19 (m, 1 H), 3.86 (m, 1 H), 3.18 (m, 1 H), 3.0–2.9 (m, 2 H), 2.42 (m, 1 H), 2.14 (m, 1 H).

$^{13}$C-NMR (125 MHz; CDCl$_3$), amidine and carbonyl carbons: δ174.5, 170.2, 167.9, 164.3.

(ii) Ph-CH$_2$—(R)CH(OH)—C(O)-Aze-Pab×HCl

The title compound was prepared according to the method described in Example 1(v) from Ph-CH$_2$—(R)CH(OH)—C(O)-Aze-Pab(Z) (0.22 g; 0.43 mmol; from step (i) above) to yield 101.5 mg (57%) of white powder.

$^1$H-NMR (600 MHz; D$_2$O): δ7.73 (d, 2 H, major rotamer), 7.62 (d, 2 H, minor rotamer), 7.5–7.4 (m, 2 H), 7.4–7.2 (m, 5 H), 7.10 (m, 2 H, minor rotamer), 4.71 (m, 1 H, major rotamer), 4.5–4.4 (m, 2 H), 4.34 (m, 1 H, minor rotamer), 4.14 (m, 1 H), 4.03 (m, 1 H), 3.53 (m, 1 H), 3.05–2.95 (m, 2 H, major rotamer), 2.9–2.7 (m, 2 H, minor rotamer), 2.65–2.5 (m, 1 H, minor rotamer), 2.5–2.3 (m, 1 H, major rotamer), 2.3–2.1 (m, 1 H).

$^{13}$C-NMR (75 MHz; D$_2$O), amidine and carbonyl carbons (rotamers): δ175.9, 175.0, 173.7, 173.2, 167.1, 166.8.

Example 11

Ch-(R)CH(OH)—C(O)-Pic-Pab (i) Boc-Pic-OH

Prepared according to M. Bodanszky and A. Bodanszky ("The Practise of Peptide Synthesis", Springer-Verlag) using THF instead of dioxan as solvent.

$^1$H NMR (300 MHz; CDCl$_3$): δ5.0–4.8 br d, 1H), 4.0 (br s, 1H), 3.0 (br s, 1H), 2.20 (d, 1H), 1.65 (m, 2H), 1.5–1.3 (s+m, 13H).

(ii) Boc-Pic-Pab(Z)

The sub-title compound was prepared according to the method described in Example 1(ii) above from Boc-Pic-OH (2.02 g; 8.8 mmol; from step (i) above) yielding 1.59 g (44%).

FAB-MS m/z 495 (M+1)$^+$ $^1$H NMR (400 MHz; CDCl$_3$): δ7.83 (d, 2H), 7.43 (d, 2H), 7.36–7.11 (m, 5H), 6.52 (bs, NH), 5.20 (s, 2H), 4.81–4.72 (m, 1H), 4.61–4.34 (m, 2H), 4.10–3.90 (m, 1H), 2.79–2.64 (m, 1H), 236–2.25 (m, 1H), 1.7–1.3 (m, 14H).

(iii) H-Pic-Pab(Z)×2HCl

Boc-Pic-Pab(Z) (1.59 g; 3.25 mmol; from step (ii) above) was dissolved in 100 mL of EtoAc saturated with HCl. The reaction mixture was evaporated after half an hour to give the title product in quantitative yield.

FAB-MS m/z 395 (M+1)$^+$ $^1$H NMR (300 MHz; D$_2$O): δ7.82 (d, 2H), 7.63–7.41 (m, 7H), 5.47 (s, 2H), 4.69–4.49 (AB-system centered at δ4.59, 2H), 4.03 (dd, 1H), 3.52 (bd, 1H), 3.10 (dt, 1H), 2.29 (dd, 1H), 2.08–1.61 (m, 5H).

(iv) H-Pic-Pab(Z)

The sub-title compound was generated by dissolving the dihydrochloride from step (iii) above in 2M NaOH followed by extraction with CH$_2$Cl$_2$ and evaporation of the organic solvent.

(v) Ch-(R)CH(OH)—C(O)-Pic-Pab(Z)

The sub-title compound was prepared according to the method described in Example 3(ii) from (R)-hexahydromandelic acid (0.152 g; 0.96 mmol) and H-Pic-Pab(Z) (0.417 g; 1.06 mmol; from step (iv) above). Flash chromatography (Si gel, first EtOAc:toluene (3:2), then EtOAc) yielded 90 mg (18%).

$^1$H-NMR (300 MHz; CDCl$_3$): δ7.82 (d, 2H), 7.5–7.2 (m, 7H), 6.63 (t, X part of ABX-system, NH), 5.21 (s, 2H), 5.14 (d, 1H), 4.46 (ABX-system, 2H), 4.26 (apparent s, 1H), 3.61 (bd,1H), 3.52 (bd, 1H), 3.06 (dt, 1H), 2.30 (bd, 1H), 1.92–1.0 (m, 14H), 0.95–0.8 (m, 1H).

$^{13}$C-NMR (75 MHz; CDCl$_3$) amidine and carbonyl carbons: δ174.8, 170.3, 167.8 and 164.6.

(vi) Ch-(R)CH(OH)—C(O)-Pic-Pab×HCl

The title compound was prepared according to the method described in Example 1(v) from Ch-(R)CH—(OH)C(O)-Pic-Pab(Z) (from 59 mg; 0.11 mmol; from step (v) above) yielding 19 mg (40%).

FAB-MS m/z 401 (M+1)$^+$ $^1$H-NMR (300 MHz; D$_2$O) the spectrum was complicated due to rotamers: δ7.91–7.72 (m, major and minor rotamer, 2H), 7.58 (d, minor rotamer,2H), 7.53 (d, major rotamer, 2H), 5.17 (apparent bs, major rotamer, 1H), 4.66–4.28 (m, 3H), 3.96 (bd, major rotamer, 1H), 3.26 (bt, major rotamer, 1H), 3.05–2.88 (m, minor rotamer, 1H), 2.39–2.20 (m, 1H), 2.0–0.75 (m, 16H).

$^{13}$C-NMR (75 MHz; MeOD) amidine and carbonyl carbons at δ175.86, 173.20, 168.53.

Example 12

Ch-CH$_2$(R)CH(OH)—C(O)-Pic-Pab×HCl (i) Ch-CH$_2$—(R)CH(OH)—C(O)OH

A solution of phenyllactic acid (2.57 g) and rhodium on alumina (0.75 g) in MeOH (170 mL) was hydrogenated in H$_2$-atmosphere at 3 atmospheres for 2 days. The mixture was filtered through hyflo and evaporated to dryness to give the product in quantitative yield.

$^1$H-NMR (400 MHz; CDCl$_3$): δ4.23 (bdd, 1H), 3.24 (apparent s, OH), 1.68 (bd, 1H), 1.63–1.43 (m, 6H), 143–1.31 (m, 1H), 1.21–1.0 (m, 3H), 0.95–0.75(m, 157 mg (0.91 mmol) 2H).

(ii) Ch-CH$_2$—(R)CH(OH)—C(O)-Pic-Pab(Z)

The sub-title compound was prepared according to the method described in Example 1(iv) from H-Pic-Pab(Z)× 2HCl (353 mg; 0.76 mmol; see Example 11(iii) above) and Ch-CH$_2$—(R)CH—(OH)—COOH (157 mg; 0.91 mmol; from step (i) above). The product was flash chromatographed (Si gel, EtOAc:toluene (7:3)) yielding 92 mg (22%).

$^1$H-NMR (300 MHz; CDCl$_3$): δ7.72 (d, 2H), 7.46–7.1 (m, 7H), 6.90 (t, NH), 5.18 (s, 2H), 5.07 (d, 1H), 4.45 (bd, 1H), 4.37 (d, 2H), 3.73–3.47 (m, 2H), 3.10 (bt, 1H), 2.24 (bd, 1H), 2.15–2.0 (m, 1H), 1.90 (bd, 1H), 1.80–1.05 (m, 12H), 1.05–0.75 (m, 3H).

$^{13}$C-NMR (75 MHz; CDCl$_3$) amidine and carbonyl carbons: δ175.88, 170.43, 168.04 and 164.58.

(iii) Ch-CH$_2$—(R)CH(OH)—C(O)-Pic-Pab×HCl

The title compound was prepared according to the method described in Example 1(v) above from Ch-CH$_2$(R)CH(OH)—C(O)-Pic-Pab(Z) (62 mg; 0.113 mmol; from step (ii) above) yielding 47 mg (92%).

FAB-MS m/z 415 (M+1)$^+$ $^1$H-NMR (300 MHz; D$_2$O) the spectrum was complicated due to rotamers: δ7.85–7.71 (m, major and minor rotamer, 2H), 7.56 (d, minor rotamer,2H), 7.50 (d, major rotamer, 2H), 5.12 (apparent bs, major rotamer, 1H), 4.68–4.25 (m, 3H,partly hidden by HDO), 3.80 (bd, major rotamer, 1H), 3.24 (bt, major rotamer, 1H), 2.89 (bt, minor rotamer, 1H), 2.25 (m, 1H), 1.92–0.82 (m, 17H), 0.60–0.40 (m, major rotamer, 1H).

$^{13}$C-NMR (75 MHz; D$_2$O) amidine and carbonyl carbons (rotamers): δ177.10, 173.88, 173.07, 167.24.

Example 13

Ph-(R)CH(OMe)-C(O)-Aze-Pab×HCl (i) H-Aze-OMe×HCl

MeOH (200 ml) was cooled to −40° C. under an argon atmosphere. Thionyl chloride (47.1 g; 0.396 mol) was added dropwise and the reaction mixture was stirred at −10° C. for 35 minutes. H-Aze-OH (10.0 g; 0.099 mol) was added and the mixture was stirred at room temperature overnight. The reaction mixture was subsequently evaporated to yield 16.1 g (100%) of the title compound.

$^1$H NMR (400 MHz; CDCl$_3$): δ5.12–5.24 (m, 1 H), 4.08–4.29 (m, 2 H), 3.84 (s, 3 H), 2.65–2.87 (m, 2 H).

(ii) Ph-(R)CH(OMe)C(O)-Aze-OMe

The subtitle compound was prepared according to the procedure described in Example 1(ii) from R(−)-α-methoxyphenyl acetic acid (0.60 g; 3.6 mmol) and H-Aze-OMe×HCl (0.55 g, 3.6 mmol, from step (i) above) yielding 0.32 g (34%).

$^1$H NMR (400 MHz; CDCl$_3$): δ7.29–7.48 (m, 5 H), 4.71–5.08 (m, 2 H), 3.92–4.31 (m, 2 H), 3.69–3.83 (m, 3 H), 3.19–3.46 (m, 3 H), 2.13–2.65 (m, 2 H).

(iii) Ph-(R)CH(OMe)-C(O)-Aze-OH

To a solution of Ph-(R)CH(OMe)-C(O)-Aze-OMe (0.32 g; 1.2 mmol; from step (ii) above) in THF (10 ml) a solution of lithium hydroxide monohydrate (0.071 g; 1.7 mmol) in H$_2$O (6 ml) was added The reaction mixture was stirred for 3 h and was subsequently evaporated. The residue was dissolved in H$_2$O and was extracted with toluene. The pH of the H$_2$O layer was adjusted to 3 with aqueous HCl followed by an extraction with ethyl acetate (4 times). The combined organic layer was evaporated to yield 0.28 g (92%) of the title compound.

$^1$H NMR (300 MHz; CDCl$_3$): δ7.30–7.50 (m, 5 H), 4.95–5.10 (m, 1 H), 4.80 (s, 1 H), 4.10–4.35 (m, 2 H), 3.40 (s, 3 H), 2.40–2.80 (m, 2 H).

(iv) Ph-(R)CH(OMe)-C(O)-Aze-Pab(Z)

The sub-title compound was prepared according to the procedure described in Example 1(ii) from H-Pab(Z)×HCl (0.36 g; 1.0 mmol) and PhCH(OMe)-C(O)-Aze-OH (0.25 g; 1.0 mmol; from step (iii) above) to yield 0.39 g (76%) as a white powder.

$^1$H-NMR (400 MHz; CDCl$_3$): δ8.29 (m, 1 H), 7.77 (d, 2 H), 7.45 (d, 2 H), 7.4–7.2 (m, 10 H), 5.22 (s, 2 H), 4.93 (m, 1 H), 4.69 (s, 1 H), 4.44 (m, 2 H), 4.15 (m, 2 H), 3.35 (s, 3 H), 2.69 (m, 1H), 2.42 (m, 1H).

(v) Ph-(R)CH(OMe)-C(O)-Aze-Pab×HCl

The title compound was prepared according to method described in Example 1(v) from Ph-(R)CH(OMe)C(O)-Aze-Pab(Z) (0.15 g; 0.29 mmol; from step (iv) above) yielding 50.4 mg (41%) as a white powder.

$^1$H-NMR (400 MHz; CD$_3$OD; the α-hydrogen of Aze and the benzylic hydrogen from the mandelate were obscured by the CD$_3$OH-signal): δ7.8–7.6 (m, 2 H), 7.6–7.4 (m, 2 H), 7.4–7.1 (m, 5 H), 4.6–4.4 (m, 2 H), 4.3–4.0 (m, 2 H), 3.29 (s, 3 H), 2.7–2.5 (m, 1 H), 2.4–2.1 (m, 1 H).

Example 14

Ph(3-OMe)-(R,S)CH(OH)—C(O)-Aze-Pab×HCl (i) Ph(3-OMe)-(R,S)(CH)(OH)—C(O)-Aze-Pab(Z)

The sub-title compound was prepared according to the method described in Example 3(ii) from (R,S)-3-methoxymandelic acid (270 mg; 1.5 mmol) yielding 340 mg (43%); diastereomeric ratio 1:1.

FAB-MS m/z 531 (M+1)$^+$ $^1$H-NMR (400 MHz; CDCl$_3$): δ8.14 (m, 1H, diastereomer), 7.87 (m, 1H, diastereomer), 7.8–7.0 (m, 10H), 6.9–6.7 (m, 3H), 5.16 (s, 2H), 4.96 (s, 1H, diastereomer), 4.88 (s, 1H, diastereomer), 4.85–4.7 (m, 1H), 4.4–4.2 (m, 2H), 4.05–3.9 (m, 1H), 3.71 (s, 3H, diastereomer), 3.71 (m, 1H, diastereomer), 3.66 (s, 3H, diastereomer), 3.58 (m, 1H, diastereomer), 2.5–2.35 (m, 1H), 2.32 (m, 1H, diastereomer), 2.20 (m, 1H, diastereomer).

$^{13}$C-NMR (100 MHz; CDCl$_3$) amidine and carbonyl carbons (diastereomers): δ173.9, 173.0, 170.5, 170.4, 168.3, 168.2, 164.5.

(ii) Ph(3-OMe)-(R,S)CH(OH)—C(O)-Aze-Pab×HCl

The title compound was prepared according to the method described in Example 1(v) from Ph(3-OMe)-(R,S)CH(OH)—C(O)-Aze-Pab(Z) (230 mg; 0.43 mmol; from step (i) above) yielding 126 mg (67%/) of product Diastereomeric ratio 1:1.

FAB-MS m/z 397 (M+1)$^+$ $^1$H-NMR (400 MHz; D$_2$O; complicated due to (diastereomers/rotamers) and some impurities): δ7.6–7.1 (m, 5H), 6.9–6.6 (m, 3H), 5.2–4.7 (m, 1–2H), 4.4–3.7 (m, 4–5H), 3.63 (s, 3H, diastereomer/rotamer), 3.55 (m, 3H, diastereomer/rotamer), 2.5–2.3 (m, 1H) 2.2–2.0 (m, 1H).

$^{13}$C-NMR (75 MHz; D$_2$O) amidine and carbonyl carbons (diastoeomers/rotamers): δ175.8, 175.4, 174.8, 174.6, 168.5.

Example 15

Ph(3-Me)-(R,S)CH(OH)—C(O)-Aze-Pab×HOAc (i) (R,S)-3-Methylmandelic acid

A mixture of 3-methylbenzaldehyde (12.0 g; 0.1 mol) and benzyltriethylammonium chloride (1.23 g; 0.005 mol) in CHCl$_3$ (16 ml) was sired at 56° C. A solution of NaOH (25 g) in H$_2$O (25 ml) was added dropwise to the mixture. When the addition was completed the reaction mixture was stirred for 1 h. The reaction mixture was diluted with H$_2$O (to give 400 ml) and extracted with diethyl ether (3×50 ml). The pH of the mixture was adjusted to 1 with H$_2$SO$_4$ (conc.) followed by an extraction with diethyl ether (6×50 ml). The combined organic layer was dried (MgSO$_4$) and evaporated. The crude product (11.6 g) was recrystallized from toluene to give 8.47 g (51%) of the title compound.

LC-MS m/z 165 (M−1)$^-$, 331 (2M−1)$^-$ $^1$H NMR (600 MHz; CD$_3$OD): δ7.10–7.28 (m,4 H), 5.08 (s, 1 H), 2.32 (s,3 H).

(ii) Ph(3-Me)-(R,S)CH(OH)—C(O)-Aze-Pab(Z)

The sub-title compound was prepared according to the method described in Example 3(ii) from (R,S)-3-methylmandelic acid (0.22 g; 1.3 mmol; from step(i) above) yielding 0.37 g (54%).

LC-MS m/z 515 (M+1)$^+$ $^1$H NMR (400 MHz; CDCl$_3$): δ8.11–8.21 (t, NH), 6.97–7.89 (m, 13 H), 5.18–5.24 (m, 2 H), 4.83–5.00 (m, 2 H), 4.37–4.58 (m, 2 H), 3.50–4.11 (m, 2 H), 2.39–2.71 (m 2 H), 2.27–2.38 (m, 3 H).

(iii) Ph(3-Me)-(R,S)CH(OH)—C(O)-Aze-Pab×HOAc

A mixture of Ph(3-Me)-(R,S)CH(OH)—C(O)-Aze-Pab (Z) (0.105 g; 0.20 mmol; from step (ii) above), acetic acid (0.012 g, 0.20 mmol) and Pd/C (5%, 0.14 g) in ethanol (12 ml) was hydrogenated at atmospheric pressure for 6 h. The reaction mixture was filtrated and the filtrate was evaporated. The crude product (97 mg) was dissolved in H$_2$O and freeze-dried resulting in a sticky product. The product was dissolved in HOAc and was freeze dried again without any improvement The product was dissolved in H$_2$O, filtered through a HPLC-filter and was freezedried. The yield was 67 mg (76%) of the title compound.

LC-MS m/z 381 (M+1)$^+$ $^1$H NMR (400 MHz; D$_2$O): δ6.89–7.72 (m, 8 H), 4.79–5.23 (m, 2 H), 3.76–4.51 (m, 4 H), 2.38–2.82 (m, 2 H), 2.15–2.27 (m, 3 H).

$^{13}$C NMR (75.5 MHz; D$_2$O; complicated due to diastereomers/rotamers) amidine and carbonyl carbons: δ181.21, 175.43, 174.38, 173.94, 173.23, 173.06, 172.16, 167.00.

Example 16

Ph(3-OEt)-(R,S)CH(OH)—C(O)-Aze-Pab×HOAc (i) (R,S)-3-Ethoxymandelic acid (R,S)-3-hydroxymandelic acid (0.712 g; 4.236 mmol) was dissolved in acetonitrile (15 ml). K$_2$CO$_3$ (2.34 g, 16.94 mmol) was added and ethyl iodide (1.03 ml, 12.71 mmol) was added dropwise. The reaction mixture was refluxed for 2 h and was subsequently evaporated. The residue was dissolved in H$_2$O (25 ml) and acetone (6 ml) and the mixture was stirred at room temperature for 3 h. The reaction mixture was evaporated and the resulting H$_2$O layer was extracted with ethyl acetate. The pH of the H$_2$O layer was adjusted to 2 with aqueous KHSO$_4$ and more H$_2$O was added to dissolve formed salts. The H$_2$O-solution was extracted with ethyl acetate (3 times). The combined organic layer was washed with H$_2$O, dried (Na$_2$SO$_4$) and evaporated. The residue was subjected to preparative RPLC (25% acetonitrile:75% 0.1 M HOAc) and the fractions containing product was evaporated. The resulting H$_2$O layer was extracted with ethyl acetate (3 times) and the combined organic layer was washed with H$_2$O, dried (Na$_2$SO$_4$) and evaporated. The yield was 182 mg (22%) of the sub-title compound.

LC-MS MWZ 195 (M−1)$^-$, 391 (2M−1)$^-$, 587 (3M−1)$^-$ $^1$H NMR (400 MHz; CD$_3$OD): δ6.80–7.27 (m, 4 H), 5.08 (s, 1 H), 3.99–4.13 (m, 2 H) 1.34–1.40 (t, 3 H).

(ii) Ph(3-OEt)-(R,S)CH(OH)—C(O)-Aze-Pab(Z)

The sub-title compound was prepared according to the method described in Example 3(ii) from (R,S)-3-ethoxymandelic acid (0.178 g; 0.907 mmol; from step (i) above) yielding 259 mg (52%).

LC-MS m/z 545 (M+1)$^+$ $^1$H NMR (400 MHz; CDCl$_3$): δ6.77–7.77 (m, 13 H), 5.16–5.21 (d, 2 H), 4.78–4.99 (m, 2 H), 4.27–4.51 (m, 2 H), 3.53–4.07 (m, 4 H), 2.21–2.60 (m, 2 H), 1.29–1.41 (m, 3 H).

(iii) Ph(3-OEt)-(R,S)CH(OH)—C(O)-Aze-Pab×HOAc

The title compound was prepared according to the method described in Example 15(iii) above from Ph(3-OEt)-(R,S)CH(OH)—C(O)-Aze-Pab(Z) (0.182 g; 0.33 mmol; from step (ii) above) yielding 157 mg (100%).

LC-MS m/z 411 (M+1)$^+$ $^1$H NMR (400 MHz; CD$_3$OD): δ7.71–7.79 (m, 2 H), 7.49–7.60 (m, 2 H), 7.19–7.30 (m, 1 H), 6.94–7.02 (m, 2 H), 6.81–6.90 (m, 1 H), 5.09–5.18 (m, 1 H), 4.74–4.81 (m, 1 H), 4.39–4.62 (m, 2 H), 3.93–4.35 (m, 4 H), 2.10–2.61 (m, 2 H), 1.32–1.40 (m, 3 H).

$^{13}$C NMR (100.6 MHz; D$_2$O; complicated due to diastereomers/rotamers) amidine and carbonyl carbons: δ180.68, 174.30, 173.50, 173.07, 172.44, 172.26.

Example 17

Ph(3-OPr(n))-(R,S)CH(OH)—C(O)-Aze-Pab×HOAc (i) (R,S)-3-Allyloxymandelic acid (R,S)-3-Hydroxymandelic acid (0.504 g; 3.0 mmol) was dissolved in dry acetone (25 ml) in nitrogen atmosphere. Allyl bromide (0.907 g; 7.5 mmol) and dry K$_2$CO$_3$ (1.037 g; 7.5 mmol) was added and the reaction mixture was stirred in nitrogen atmosphere for 16 h. The reaction mixture was subsequently evaporated. The residue was dissolved in H$_2$O (25 ml) and acetone (6 ml) and the mixture was stirred for 2 h (the reaction was followed by HPLC). The mixture was evaporated and the water layer was extracted with ethyl acetate. The pH of the water layer was adjusted to 2 with aqueous KHSO$_4$ and extracted with ethyl acetate (3 times). The combined organic layer was washed with H$_2$O, dried (Na$_2$SO$_4$) and evaporated to give the sub-title product in a yield of 0.175 g (28%).

$^1$H NMR (500 MHz; CDCl$_3$): δ6.87–7.30 (m, 4 H), 5.97–6.10 (m, 1 H), 5.26–5.44 (m 2 H), 5.20 (s, 1 H), 4.51–4.55 (d, 2 H).

(ii) Ph(3-OCH$_2$CH=CH$_2$)—(R,S)CH(OH)—C(O)-Aze-Pab(Z)

The sub-title compound was prepared according to the method described in Example 3(ii) from (R,S)-3-allyloxymandelic acid (0.167 g; 0.8 mmol; from step (i) above) yielding 260 mg (58%).

$^1$H NMR (500 MHz; CDCl$_3$): δ8.09–8.17 (t, NH), 6.79–7.87 (m, 13 H), 5.94–6.09 (m, 1 H), 5.20–5.44 (m, 4 H), 4.86–5.02 (m, 2 H),4.32–4.62 (m, 4 H), 3.54–4.15 (m, 2 H), 2.30–2.74 (m, 2H).

(iii) Ph(3-OPr(n))-(R,S)CH(OH)—C(O)-Aze-Pab×HOAc

The title compound was prepared according to the method described in Example 15(iii) from Ph(3-OCH$_2$CH=CH$_2$)—(R,S)CH(OH)—C(O)-Aze-Pab(Z) (0.06 g; 0.1 mmol; from step (ii) above) yielding 47 mg (97%).

LC-MS m/z 425 (M+1)$^+$, 423 (M−1)$^-$ $^1$H NMR (500 MHz; D$_2$O): δ6.70–7.71 (m, 8 H), 4.70–5.25 (m, 2 H), 3.78–4.53 (m, 6 H), 2.05–2.80 (m, 2 H), 1.56–1.75 (m, 2 H), 0.82–0.95 (m, 3 H).

Example 18

Ph(3-OPr(iso))-(R,S)CH(OH)—C(O)-Aze-Pab× HOAc (i) (R,S)-3-isopropoxymandelic acid The sub-title compound was prepared according to the method described in Example 16(i) above from (R,S)-3-hydroxymandelic acid (0.70 g; 4.16 mmol), Cs$_2$CO$_3$ (5.87 g; 16.65 mmol) and isopropyl iodide (1.25 ml; 12.49 mmol) yielding 62 mg (7%).

LC-MS m/z 209 (M−1)$^-$ $^1$H NMR (400 MHz; CD$_3$OD): δ6.81–7.25 (m, 4 H), 5.08 (s, 1 H), 4.53–4.64 (m, 1 H), 1.28–1.32 (d, 6 H).

(ii) Ph(3-OPr(iso))-(R,S)CH(OH)—C(O)-Aze-Pab(Z)

The sub-title compound was prepared according to the method described in Example 3(ii) is above from (R,S)-3-isopropoxymandelic acid (0.063 g; 0.3 mmol; from step (i) above) yielding 60 mg (34%).

LC-MS m/z 559 (M+1)$^+$ $^1$H NMR (400 MHz; CDCl$_3$): δ6.75–7.79 (m, 13 H), 5.18–5.24 (m, 2 H), 4.81–4.99 (m, 2 H), 4.31–4.58 (m, 3 H), 3.97–4.15 (m, 1 H), 3.55–3.77 (m, 1 H), 2.24–2.64 (m, 2 H), 1.23–1.33 (m, 6H).

(iii) Ph(3-OPr(iso))-(R,S)CH(OH)—C(O)-Aze-Pab×HOAc

The title compound was prepared according to the method described in Example 15(iii) above from Ph(3-OPr(iso))-(R,S)CH(OH)—C(O)-Aze-Pab(Z) (0.05 g; 0.090 mmol; from step (ii) above) yielding 41 mg (94%).

LC-MS m/z 425 (M+1)$^+$ $^1$H NMR (400 MHz; CD$_3$OD): δ6.81–7.80 (m, 8 H), 5.08–5.18 (m, 1 H), 4.74–4.80 (m, 1 H), 4.53–4.64 (m, 2 H), 4.41–4.51 (m, 1 H), 3.93–4.35 (m, 2 H), 2.23–2.60 (m, 2 H), 1.25–1.32 (m, 6 H).

$^{13}$C NMR (100.6 MHz; D$_2$O; complicated due to diastereomers/rotamers) amidine and carbonyl carbons: δ181.10, 173.60, 173.15, 172.48, 166.39.

Example 19

Ph(2-OMe)-(R,S)CH(OH)—C(O)-Aze-Pab×HOAc (i) Ph(2-OMe)-(R,S)CH(OH)—C(O)-Aze-Pab(Z)

The sub-title compound was prepared according to the method described in Example 3(ii) above from (R,S)-2-methoxymandelic acid (0.18 g; 1.0 mmol) yielding 80 mg (17%).

$^1$H NMR (500 MHz; CDCl$_3$): δ8.16–8.22, (t, NH), 6.81–7.85 (m, 13 H), 5.16–5.20 (m, 2 H), 4.79–4.91 (m, 1 H), 4.35–4.49 (m,2 H), 3.84–4.02 (m, 2 H), 3.63–3.80 (m, 3 H), 3.32–3.56 (m, 1 H), 2.21–2.57 (m, 2 H).

(ii) Ph(2OMe)-(R,S)CH(OH)—C(O)-Aze-Pab×HOAc

The title compound was prepared according to the method described in Example 15(iii) above from Ph(2-OMe)-(R,S)CH(OH)—C(O)-Aze-Pab(Z) (0.08 g; 0.15 mmol; from step (i) above) yielding 45 mg (71%).

FAB-MS m/z 397 (M+1)$^+$ $^1$H NMR (500 MHz; D$_2$O): δ6.83–7.70 (m, 8 H), 4.71–4.97 (m, 1 H), 4.34–4.51 (m, 2 H), 3.87–4.22 (m, 3 H), 3.67–3.75 (m, 3 H), 2.00–2.74 (m, 2 H).

$^{13}$C NMR (75.5 MHz; D$_2$O; complicated due to diastereomers/rotamers) amidine and carbonyl carbons: δ179.96, 176.28, 174.97, 174.50, 173.44, 173.39, 173.29, 173.10, 167.12.

Example 20

Ph(3,5-diOMe)-(R,S)CH(OH)—C(O)-Aze-Pab×HOAc (i) Ph(3,5-diOMe)-(R,S)CH(OH)—C(O)-Aze-Pab(Z)

The sub-title compound was prepared according to the method described in Example 3(ii) above from (R,S)-3,5-dimethoxymandelic acid (0.21 g; 1.0 mmol; prepared according to the method described in Synthesis (1974) 724) yielding 0.31 g (62%).

$^1$H NMR (500 MHz; CDCl$_3$): δ8.11–8.16 (t NH), 7.17–7.86 (m, 9 H), 6.41–6.49 (m, 3 H), 5.21–5.24 (d, 2 H), 4.84–5.03 (m, 2 H), 4.29–4.66 (m, 2 H), 3.67–4.17 (m, 8 H), 2.32–2.72 (m, 2H).

(ii) Ph(3,5-diOMe)-(R,S)CH(OH)—C(O)-Aze-Pab×HOAc

The title compound was prepared according to the method described in Example 15(iii) above from Ph(3,5-diOMe)-(R,S)CH(OH)—C(O)-Aze-Pab(Z) (0.15 g; 0.27 mmol; from step (i) above) yielding 120 mg (100%).

$^1$H NMR (500 MHz; D$_2$O): δ7.34–7.75 (m, 4 H), 6.44–6.66 (m, 3 H), 4.67–5.12 (m, 1 H), 3.97–4.55 (m, 5 H), 3.79 (s, 3 H), 3.71–3.74 (m, 3 H), 2.14–2.85 (m, 2 H).

$^{13}$C NMR (75.5 MHz; D$_2$O; complicated due to diastereomers/rotamers) amidine and carbonyl carbons: 181.17, 174.85, 173.92, 173.53, 173.09, 172.98, 182.90, 166.77.

Example 21

Ph(3-OMe,4-OH)—(R,S)CH(OH)—C(O)-Aze-Pab×HOAc (i) Ph(3-OMe,4-OH)—(R,S)CH(OH)—C(O)-Aze-Pab(Z)

The sub-title compound was prepared according to the method described in Example 3(ii) above from (R,S)-4-hydroxy-3-methoxymandelic acid (0.20 g; 1.0) yielding 89 mg (16%).

LC-MS m/z 547 (M+1)$^+$, 545 (M–1)$^-$ $^1$H NMR (400 MHz; CDCl$_3$): δ8.07–8.15 (m, NH), 6.64–7.86 (m, 12 H), 5.20–5.27 (m, 2 H), 3.57–5.00 (m, 9 H), 2.31–2.74 (m, 2 H).

(ii) Ph(3-OMe,4-OH)—(R,S)CH(OH)—C(O)-Aze-Pab×HOAc

The title compound was prepared according to the method described in Example 15(iii) above from Ph(3-OMe,4-OH)—(R,S)CH(OH)—C(O)-Aze-Pab(Z) (0.085 g; 0.16 mmol; from step (i) above yielding 57 mg (78%).

FAB-MS m/z 413 (M+1)$^+$ $^1$H NMR (500 MHz; D$_2$O; complicated due to diasteremoers/rotamers): δ6.66–7.83 (m, 8 H), 4.80–5.25 (m, 2 H), 3.88–4.59 (m, 4H), 3.68–3.88 (m 3 H), 2.10–2.85 (m, 2 H).

$^{13}$C NMR (75.5 MHz; D$_2$O; complicated due to diastereomers/rotamers) amidine and carbonyl carbons: δ182.01, 175.56, 174.43, 174.04, 173.20, 173.05, 166.90, 166.85.

Example 22

Ph(2-F,5-CF$_3$)—(R,S)CH(OH)—C(O)-Aze-Pab×HOAc (i) Ph(2-F,5-CF$_3$)—(R,S)CH(OH)—C(O)-Aze-Pab(Z)

The sub-title compound was prepared according to the method described in Example 3(ii) above from (R,S)-2-fluoro-5-trifluoromethylmandelic acid (0.3 g, 1.2 mmol; prepared according to the method described in Org. Synth. Coll. I, 336) yielding 0.32 g (51%).

FAB-MS m/z 587 (M+1)$^+$ $^1$H NMR (400 MHz; CDCl$_3$): δ7.15–7.87 (m, 12 H), 5.19–5.30 (m, 2 H), 4.87–5.00 (m, 1 H), 4.36–4.60 (m, 3 H), 4.05–4.20 (m, 1 H), 3.60–3.73 (m, 1 H), 2.32–2.72 (m, 2 H).

(ii) Ph(2-F,5CF$_3$)—(R,S)CH(OH)—C(O)-Aze-Pab×HOAc

The title compound was prepared according to the method described in Example 15(iii) above from Ph(2-F,5CF$_3$)—(R,S)CH(OH)—C(O)-Aze-Pab(Z) (0.15 g; 0.26 mmol; from step (i) above yielding 110 mg (90/%).

$^1$H NMR (500 MHz, D$_2$O): δ7.28–7.83 (m, 7 H), 5.43–5.65 (m, 1 H), 4.82–5.18 (m, 1 H), 3.97–4.56 (m, 4 H), 2.14–2.85 (m, 2 H).

$^{13}$C NMR (75.5 MHz; D$_2$O; complicated due to diastereomers/rotamers) amidine and carbonyl carbons: δ173.61, 173.33, 173.06, 172.83, 172.68, 172.62, 166.86, 164.27, 161.15, 160.92.

Example 23

Ph-(R,S)C(Et)(OH)—C(O)-Aze-Pab×HOAc (i) Ph-(R,S)C(Et)(OH)—C(O)-Aze-Pab(Z)

The sub-title compound was prepared according to the method described in Example 3(ii) above from (R,S)-2-hydroxy-2-phenyl butanoic acid (0.18 g; 1.0 mmol), yielding 79 mg (15%).

LC-MS m/z 529 (M+1)$^+$, 527 (M–1)$^-$ $^1$H NMR (400 MHz, CDCl$_3$): δ7.27–7.86 (m, 14 H), 5.22 (s, 2 H), 4.82–4.93 (m, 1 H), 4.39–4.57 (m, 2 H), 3.84–3.98 (m, 2 H), 2.02–2.64 (m, 4 H), 0.86–0.93 (m, 3 H).

(ii) Ph-(R,S)C(Et)(OH)—C(O)-Aze-Pab×HOAc

The title compound was prepared according to the method described in Example 15(iii) above from Ph-(R,S)C(Et)(OH)—C(O)-Aze-Pab(Z) (0.08 g; 01.5 mmol; from step (i) above yielding 62 mg (90%) of the title compound.

FAB-MS m/z 395 (M+1)$^+$ $^1$H NMR (400 MHz; D$_2$O): δ7.27–7.84 (m, 9 H), 4.83–5.35 (m, 1 H), 3.89–4.60 (m, 4 H), 2.40–2.61 (m, 1 H), 1.95–2.30 (m, 3 H), 0.78–0.95 (m, 3 H).

$^{13}$C NMR (75.5 MHz; D$_2$O; complicated due to diastereomers/rotamers) amidine and carbonyl carbons: δ182.09, 175.79, 175.48, 173.53, 173.23, 167.05.

Example 24

Ph-(R,S)C(Me)(OH)—C(O)-Aze-Pab×HOAc

(i) Ph-(R,S)C(Me)(OH)—C(O)-Aze-Pab(Z)

The subtitle compound was prepared according to the method described in Example 3(ii) above from (S)-(+)-2-hydroxy-2-phenyl propionic acid (0.20 g; 1.2 mmol) yielding 0.17 g (31%).

$^1$H NMR (500 MHz; CDCl$_3$): δ8.04–8.14 (t, NH), 7.17–7.80 (m, 14 H), 5.20 (s, 2 H), 4.76–4.86 (m, 1 H), 4.31–4.50 (m, 2 H), 3.76–3.94 (m, 2 H), 2.19–2.44 (m, 2 H), 1.70 (s, 3 H).

(ii) Ph-(R,S)C(Me)(OH)—C(O)-Aze-Pab×HOAc

The title compound was prepared according to the method described in Example 15(iii) above from Ph-(R,S)C(Me)(OH)—C(O)-Aze-Pab(Z) (0.08 g; 0.16 mmol; from step (i) above) yielding 48 mg (78%), diasteromeric ratio: 85:15.

$^1$H NMR (500 MHz; D$_2$O): δ7.30–7.79 (m, 9 H), 3.99–4.82 (m, 5 H), 2.09–2.74 (m, 2 H), 1.70–1.77 (m, 3 H).

$^{13}$C NMR (75.5 MHz; D$_2$O; complicated due to rotamers) amidine and carbonyl carbons: δ176.90, 176.34, 173.89, 173.48, 167.00.

Example 25

Ph-(R)CH(OH)—C(O)-Aze-Pac×HOAc

(i) Boc-Aze-OSu

A mixture of Boc-Aze-OH (5 g, 25 mmol) and HOSu (2.88 g, 25 mmol) in 25 ml of THF was cooled on an ice bath. EDC (4.3 ml, 25 mmol) was added and the solution was stirred overnight. It was evaporated, dissolved in ethyl acetate, washed with KHSO$_4$ (aq, 0.3 M), Na$_2$CO$_3$ (aq, 10%), dried (MgSO$_4$) and evaporated. Crystallization from ethyl acetate:petroleum ether afforded 3.78 g (51%) of sub-title compound.

$^1$H NMR (300 MHz; CDCl$_3$) δ4.89 (m, 1 H), 4.07 (m, 1 H), 3.95 (m, 1 H), 2.85 (s, 4H), 2.67 (m, 1H), 2.45 (m, 1H), 1.42 (s, 9H).

(ii) Boc-Aze-Pac(Z)

A mixture of H-Pac(Z)×2HCl (0.227 g, 0.63 mmol), Boc-Aze-OSu (0.194 g, 0.65 mmol) and triethylamine (0.2 ml, 1.4 mmol) in 10 ml of THF was stired at room temperature for 18 h. After evaporation the residue was dissolved in ethyl acetate, filtered through a plug of Celite and chromatographed on a silica gel column with ethyl acetate:THF (2:1). The eluent was evaporated, dissolved in ethyl acetate, washed with water, dried (MgSO$_4$) and evaporated to give 0.250 g (81%) of sub-title compound.

$^1$H NMR (300 MHz; CDCl$_3$) δ7.4–7.2 (m, 5H), 5.05 (s, 2H), 4.55 (bt, 1H), 3.85 (bq, 1H), 3.72 (bq, 1 H), 3.2–3.0 (m, 2H), 2.4–2.2 (m, 2H), 2.10 (m, 1H), 1.9–1.7 (m, 4H), 1.5–1.3 (m, 11H, thereof s at 1.37, 9H) 1.0–0.8 (m, 2H).

(iii) H-Aze-Pac(Z)

The subtitle compound was prepared according to the method described in Example 3(i) from Boc-Aze-Pac(Z) (from step (ii) above) followed by an alkaline extractive work up.

(iv) Ph-(R)CH(OTBDMS)-C(O)-Aze-Pac(Z)

The sub-title compound was prepared analogously to the method described in Example 1(ii) above from Ph-(R)CH(OTBDMS)-C(O)OH (0.236 g, 0.89 mmol, prepared according to Hamada et al. J.Am. Chem. Soc., (1989) 111, 669) and H-Aze-Pac(Z) (0.25 g; 0.53 mmol; from step (iii) above; previously activated by stirring in CH$_2$Cl$_2$:trifluoroacetic acid (1:1; 10 ml) for 30 minutes) yielding 160 mg (48%).

$^1$H NMR (500 MHz; CDCl$_3$): δ7.20–7.44 (m, 10 H), 5.22 (s, 1 H), 5.06–5.16 (m, 2 H), 4.80–4.90 (m, 1 H), 3.92–4.43 (m, 2 H), 2.88–3.12 (m, 2 H), 2.35–2.60 (m, 2 H), 1.25–2.10 (m, 10 H), 0.84–0.94 (m, 9 H), 0.00–0.15 (m, 6 H).

(v) Ph-(R)CH(OH)—C(O)-Aze-Pac×HOAc

The title compound was prepared according to the method described in Example 15(iii) above from Ph-(R)CH(OTBDMS)-C(O)-Aze-Pac(Z) (0.16 g; 0.25 mmol; from step (iv) above), with purification by RPLC yielding 15 mg (14%).

FAB-MS m/z 373 (M+1)$^+$

Example 26

Ph-(R)CH(OH)—C(O)-Aze-Pig×HOAc

(i) Boc-Aze-Pig(Z)

The subtitle compound was prepared analogously to the method described in Example 1(ii) from Boc-Aze-OH (1.03 g; 5.12 mmol; see Example 1(i) above) and H-Pig(Z)×2HCl (1.86 g, 5.12 mmol; prepared according to the method described in International Patent Application WO 94/29336) yielding 1.24 g (51%).

$^1$H NMR (400 MHz; CDCl$_3$): δ7.27–7.43 (m, 5 H), 5.12 (s,2 H), 4.60–4.67 (t, 1 H), 4.16–4.26 (d, 2 H), 3.86–3.95 (m, 1 H), 3.74–3.82 (m, 1 H), 3.11–3.30 (m, 2 H), 2.78–2.89 (m, 2 H), 2.33–2.52 (bs, 2 H), 1.71–1.83 (m, 3 H), 1.44 (s, 9 H), 1.15–1.29 (m, 2 H).

(ii) H-Aze-Pig(Z)×2HCl

Boc-Aze-Pig(Z) (1.2 g; 2.53 mmol; from step (i) above) in ethyl acetate saturated with HCl (75 ml) was stired at room temperature for 1 h. The reaction mixture was evaporated, diluted with water and extracted with toluene. The water layer was freeze dried to give 1.085 g (96%) of the title compound.

$^1$H NMR (500 MHz; CD$_3$OD): δ7.32–7.46 (m, 5 H), 5.28 (s, 2 H), 4.99–5.05 (t, 1 H), 4.08–4.16 (m, 1 H), 3.91–3.99 (m, 3 H), 3.13–3.25 (m, 4 H), 2.79–2.88 (m, 1 H), 2.47–2.57 (m, 1 H), 1.82–1.96 (m, 3 H), 1.26–1.40 (m, 2H).

(iii) Ph-(R)CH(OTBDMS)-C(O)-Aze-Pig(Z)

The sub-title compound was prepared analogously to the method described in Example 25(iv) above from Ph-(R)CH(OTBDMS)-C(O)OH (0.401 g; 1.5 mmol) and H-Aze-Pig(Z)×2HCl (0.672 g; 1.5 mmol; from step (iii) above) yielding 350 mg (46%).

LC-MS m/z 508 (M+1)$^+$, 530 (M+Na)$^+$ (iv) Ph-(R)CH(OH)—C(O)-Aze-Pig×HOAc

The title compound was prepared according to the method described in Example 15(iii) above from Ph-(R)CH(OH)—C(O)-Aze-Pig(Z) (0.1 g; 0.197 mmol; from step (iv) above) yielding 81 mg (95%) of the title compound.

LC-MS mz 374 (M+1)$^+$ $^1$H NMR (400 MHz; CD$_3$OD): δ7.25–7.50 (m, 5 H), 5.15 (s, 1 H), 4.65–4.75 (m, 1 H), 4.25–4.35 (m, 1 H), 3.80–4.00 (m, 3 H), 2.95–3.50 (m, 4 H), 2.05–2.50 (m, 2 H), 1.75–1.90 (m, 3 H), 1.15–1.30 (m, 2 H).

Example 27

Ph-(R)CH(OH)—C(O)-Pro-(R,S)Hig×HOAc

(i) H—(R,S)Hig(Z)×2HCl

The subtitle compound was prepared according to the method described in Example 3(i) from Boc-(R,S)Hig(Z) (prepared according to the method described in International Patent Application WO 94/29336).

(ii) Ph-(R)CH(OTBDMS)-C(O)-Pro-OBn

The sub-title compound was prepared according to the method described in Example 1(ii) from L-proline benzylester×HCl (2.0 g, 8.26 mmol) and Ph-(R)CH(OTBDMS)-C(O)OH (2.0 g, 7.51 mmol, prepared according to the method described by Hamada et al in J. Am. Chem. Soc. (1989) 111, 669) yielding 2.0 g (59%).

¹H NMR (500 MHz; CDCl₃): δ7.22–7.55 (m, 10 H), 5.45 (s, 1 H), 5.15 (s, 2 H), 4.45–4.55 (m, 1 H), 3.70–3.82 (m, 1 H), 3.05–3.15 (m, 1 H), 1.65–2.15 (m, 4 H), 0.85–1.05 (m, 9 H), 0.00–0.22 (m, 6 H).

(iii) Ph-(R)CH(OTBDMS)-C(O)-Pro-OH

A mixture of Ph-(R)CH(OTBDMS)-C(O)-Pro-OBn (1.9 g, 4.19 mmol, from step (ii) above) and Pd/C (10%, 0.21 g) in ethanol (80 ml) was hydrogenated at atmospheric pressure for 3 h. The reaction mixture was filtered through celite and the filtrate was evaporated. The yield was 1.36 g (91%) of the title compound.

LC-MS m/z 362 (M−1)⁻

¹H NMR (500 MHz; CD₃OD): δ7.20–7.50 (m, 5 H), 5.45 (s, 1 H), 4.30–4.40 (m, 1 H), 3.30–3.70 (m, 2 H), 1.75–2.30 (m, 4 H), 0.85–1.00 (m, 9 H), 0.00–0.20 (m, 6 H).

(iv) Ph-(R)CH(OTBDMS)-C(O)-Pro-(R,S)-Hig(Z)

The sub-title compound was prepared analogously to the method described in Example 25(iv) above from Ph-(R)CH(OTBDMS)-C(O)-Pro-OH (0.36 g; 1 mmol; from step (iii) above) and H—(R,S)Hig(Z)×2HCl (0.36 g; 1 mmol; from step (i) above yielding 0.63 g of crude product which was used without further purification in the proceeding step.

LC-MS m/z 636 (M+1)⁺

¹³C NMR (100.5 MHz; CDCl₃) amidine and carbonyl carbons: δ171.57, 171.20, 163.79, 159.22.

(v) Ph-(R)CH(OH)—C(O)-Pro-(R,S)Hig(Z)

A mixture of Ph-(R)CH(OTBDMS)-C(O)-Pro-(R,S)Hig(Z) (0.63 g; 1 mmol; from step (iv) above) and TFA (10 ml, 20% in CH₂Cl₂) was stirred at room temperature for 3 h. The pH of the reaction mixture was adjusted to 9 with aqueous K₂CO₃ and the reaction mixture was subsequently extracted with CH₂Cl₂. The combined organic layer was dried (Na₂SO₄) and evaporated. The crude product was purified by flash chromatography on a silica gel column (40 g) eluted with CH₂Cl₂ (100 ml), CH₂Cl₂:EtOH 95:5 (100 ml) and CH₂Cl₂:EtOH (9:1; 300 ml). The yield was 138 mg (26%) of the sub-title compound.

LC-MS m/z 522 (M+1)⁺

¹³C NMR (100.5 MHz; CDCl₃) amidine and carbonyl carbons: δ172.21, 171.20, 163.64, 159.11.

(vi) Ph-(R)CH(OH)—C(O)-Pro-(R,S)Hig×HOAc

The title compound was prepared according to the method described in Example 15(iii) above from Ph-(R)CH(OH)—C(O)-Pro-(R,S)Hig(Z) (0.071 g; 0.14 mmol; from step (v) above yielding 49 mg (80%).

LC-MS m/z 388 (M+1)⁺

¹H NMR (400 MHz; D₂O; complicated due to diastereomers/rotamers): δ7.32–7.56 (m, 5 H), 5.37–5.52 (m, 1 H), 4.32–4.64 (m, 1 H), 3.57–3.75 (m, 2 H), 3.24–3.56 (m, 4 H), 2.89–3.15 (m, 2 H), 1.25–2.80 (m, 9 H).

¹³C NMR (75.5 MHz; D₂O; complicated due to diastereomers/rotamers) amidine and carbonyl carbons: 181.92, 174.92, 173.69, 173.03.

Example 28

Ph-(R)CH(OH)—C(O)-Pro-Dig×HOAc (i) Ph-(R)CH(OTBDMS)—C(O)-Pro-Dig(Z)

The sub-title compound was prepared analogously to the method described in Example 25(iv) above from H-Dig(Z) (0.14 g; 0.507 mmol; see International Patent Application WO 94/29336) and Ph-(R)CH(OTBDMS)-C(O)-Pro-OH (0.23 g; 0.608 mmol; see Example 27(iii) above) yielding 316 mg of crude product which was used in the proceeding step without further purification.

LC-MS m/z 622 (M+1)⁺

(ii) Ph-(R)CH(OH)—C(O)-Pro-Dig(Z)

Trifluoroacetic acid (6 ml; 20% in CH₂Cl₂) was added to Ph-(R)CH(OTBDMS)-C(O)-Pro-Dig(Z) (0.315 g; 0.506 mmol; from step (i) above) at 0° C. and the mixture was stirred at room temperature for 2 h. The pH of the reaction mixture was adjusted to 8 with aqueous K₂CO₃ and was extracted with CH₂Cl₂. The organic layer was washed with aqueous NaCl, dried (Na₂SO₄) and evaporated. The crude product (250 mg) was flash chromatographed on a silica gel column using CH₂Cl₂:MeOH (9:1) as eluent yielding 180 mg (70%) of the title compound.

¹H NMR (400 MHz; CDCl₃): δ7.25–7.39 (m, 10 H), 5.32–5.37 (bs, 1 H), 5.08–5.19 (m, 2 H), 4.40–4.49 (m, 1 H), 4.21–4.35 (m, 2 H), 3.87–4.03 (m, 2 H), 3.71–3.79 (m, 2 H), 3.18–3.32 (m, 2 H), 3.00–3.10 (m, 1 H), 2.61–2.73 (m, 1 H), 2.14–2.24 (m, 1 H), 1.62–2.07 (m, 8 H).

(ii) Ph-(R)CH(OH)—C(O)-Pro-Dig×HOAc

The title compound was prepared according to the method described in Example 15(iii) above from Ph-(R)CH(OH)—C(O)-Pro-Dig(Z) (0.14 g; 0.276 mmol; from step (iii) above yielding 112 mg (94%).

¹H NMR (400 MHz; CD₃OD): δ7.27–7.44 (m, 5 H), 5.34 (s, 1 H), 4.29–4.35 (m, 1 H), 4.17–4.25 (m, 2 H), 3.75–3.83 (m, 2 H), 3.63–3.73 (m, 1 H), 3.25–3.34 (m, 1 H), 3.08–3.23 (m, 2 H), 2.79–2.90 (m, 1 H), 1.71–2.10 (m, 6 H).

¹³C NMR (100.6 MHz; CD₃OD) amidine and carbonyl signals: δ174.79, 173.26, 158.16.

Example 29

Ph-(R)CH(OH)—C(O)—(R or S)Pic(cis-4-Me)-Pab×HOAc and Ph-(R)CH(OH)—C(O)—(S or R) Pic(cis-4-Me)-Pab×HOAc (i) (R,S)—N-Boc-Pic(cis-4-Me)-Pab(Z)

The sub-title compound was prepared analogously to the method described in Example 1(ii) from (R,S)—N-Boc-Pic(cis-4-Me)-OH (0.88 g; 4.1 mmol; prepared according to the method described in Shiman et al J. Org. Chem. (1990), 55, 738) yielding 405 mg (19%).

FAB-MS m/z 509 (M+1)⁺

¹H NMR (400 MHz; CDCl₃): δ7.25–7.90 (m, 9 H), 5.20 (s, 2 H), 4.45–4.50 (m, 2 H), 4.30–4.40 (m, 1 H), 3.15–3.70 (m, 2 H), 170–2.00 (m, 4H), 1.45 (s, 9 H), 1.15–1.30 (m, 1 H), 0.90–1.05 (m, 3 H).

(ii) H—(R,S)Pic(cis-4-Me)-Pab(Z)

(R,S)—N-Boc-Pic(cis-4-Me)-Pab(Z) (0.40 g; 0.79 mmol; from step (i) above) was dissolved in CH₂Cl₂ (5 ml). Trifluoroacetic acid (5 ml) was added and the mixture was stirred for 0.5 h. The reaction mixture was evaporated and the residue was dissolved in CH₂Cl₂, washed with aqueous Na₂CO₃, dried (MgSO₄) and evaporated. The crude product was purified by flash chromatography on a silica gel column eluted with CH₂Cl₂:MeOH 95:5 and CH₂Cl₂:MeOH 9:1. The yield was 300 mg (94%) of the sub-title compound.

FAB-MS m/z 409 (M+1)⁺

¹H NMR (500 MHz; CD₃OD): δ7.25–7.85 (m, 9 H), 5.15 (s, 2 H), 4.35–4.45 (m, 2 H), 2.55–3.60 (m, 3 H), 1.85–2.05 (m, 1 H), 1.35–1.65 (m, 2 H), 0.90–1.20 (m, 5 H).

(iii) Ph-(R)CH(OTBDMS)-C(O)—(R,S)Pic(cis-4-Me)-Pab(Z)

The sub-title compound was prepared analogously to the method described in Example 3(ii) above from H—(R,S)Pic(cis-4-Me)-Pab(Z) (0.290 g; 0.71 mmol; from step (ii) above) and Ph-(R)CH(OTBDMS)-C(O)—OH (0.189 g; 0.71 mmol; prepared according to the method described in Hamada et al J. Am. Chem. Soc. (1989) 111, 669) yielding 0.40 g of crude product which was used in the proceeding step without purification.

(iv) Ph-(R)CH(OH)—C(O)—(R,S)Pic(cis-4-Me)-Pab(Z)

Ph-(R)CH(OTBDMS)-C(O)—(R,S)Pic(cis-4-Me)-Pab(Z) (0.40 g; crude from step (iii) above) was treated with trifluoroacetic acid (20% in CH$_2$Cl2) for 3 h. The reaction mixture was evaporated and the residue was purified by flash chromatography on a silica gel column eluted with CH$_2$Cl$_2$:MeOH (98:2, 95:5 and 9:1). The yield was 45 mg (11%) of the sub-title compound.

(v) Ph-(R)CH(OH)—C(O)—(R or S)Pic(cis-4-Me)-Pab× HOAc and Ph(R)CH(OH)—C(O)—(S or R)Pic(cis-4-Me)-Pab×HOAc A mixture of Ph-(R)CH(OH)—C(O)—(R,S)Pic(cis-4-Me)-Pab(Z) (0.045 g; 0.083 mmol; from step (iv) above) and Pd/C (5%; 0.06 g) in ethanol (8 mL) was hydrogenated at atmospheric pressure for 2.5 h. The reaction mixture was filtered and the filtrate was evaporated. The crude product was subjected to preparative RPLC (0.1M NH$_4$OAc; 30% acetonitrile) where the diastereomers were separated. The yield was 7 mg of compound 29A with a diastereomeric ratio>99:1 and 11 mg of compound 29B with a diastereomeric ratio 98:2.

Compound 29A:
LC-MS m/z 409 (M+1)$^+$, 407 (M-1)$^-$
$^1$H NMR (500 MHz; D$_2$O): δ7.20–7.80 (m, 9 H), 5.65 (s, 1 H), 4.65–5.35 (m, 1 H), 4.40–4.55 (m, 2 H), 3.85–4.00 (m, 1 H), 3.65–3.75 (m, 1 H), 2.65–3.15 (m, 2 H), 2.05–2.20 (m, 1 H), 1.05–1.75 (m, 2 H), 0.70–0.90 (m, 3 H).

Compound 29B:
LC-MS m/z 409 (M+1)$^+$, 407 (M-1)$^-$
$^1$H NMR (500 MHz; D$_2$O): δ7.25–7.80 (m, 9 H), 4.55–5.75 (m, 2 H), 4.35–4.50 (m, 3 H), 3.75–3.85 (m, 1 H), 2.70–2.80 (m, 1 H), 1.80–2.20 (m, 1 H), 0.70–1.70 (m, 6 H).

Example 30

Ph-(CH$_2$)$_2$—(R)CH(OH)—C(O)-Aze-Pab×HCl
(i) Ph-(CH$_2$)$_2$—(R)CH(OH)—C(O)-Aze-Pab(Z)

The sub-title compound was prepared analogously to the method described in Example 3(ii) above from H-Aze-Pab (Z)×2HCl (0.434 g, 0.988 mmol) and (R)-(–)-2-hydroxy-4-phenylbuturic acid (0.162 g; 0.898 mmol), TBTU (0.433 g, 1.348 mmol) and N-methylmorpholine (0.363 g; 3.59 mmol) in DMF (15 ml) yielding 105 mg (22%).

LC-MS m/z 529 (M+1)$^+$, 527 (M-1)$^-$
$^1$H NMR (500 MHz; CDCl$_3$): δ8.17–8.25 (m, NH), 7.05–7.72 (m, 14 H), 5.16–5.22 (m, 2 H), 4.71–4.88 (m, 1 H), 4.32–4.41 (m, 2 H), 3.92–4.04 (m, 2 H), 3.79–3.88 (m, 1 H), 2.62–2.86 (m, 2 H), 2.29–2.57 (m, 2 H), 1.80–1.98 (m, 2 H).

(ii) Ph-(CH$_2$)$_2$—(R)CH(OH)—C(O)-Aze-Pab×HCl

The title compound was prepared according to the method described in Example 1(v) above from Ph-(CH$_2$)$_2$—(R)CH(OH)—C(O)-Aze-Pab(Z) (0.112 g; 0.212 mmol; from step (i) above) yielding 77 mg (84%).

LC-MS m/z 395 (M+1), 393 (M-1)$^-$
$^1$H NMR (400 MHz; CD$_3$OD): δ7.77–7.77 (m, 9H), 4.73–5.19 (m, 1 H), 4.40–4.62 (m, 2 H), 3.92–4.34 (m, 3 H), 2.48–2.84 (m, 3 H), 2.09–2.33 (m, 1 H), 1.83–2.05 (m, 2 H).

$^{13}$C NMR (100.6 MHz; D$_2$O; complicated due to rotamers) amidine and carbonyl carbons: δ175.66, 174.80, 172.56, 172.49, 166.14, 165.87.

Example 31

2-Naphthyl-(R,S)CH(OH)—C(O)-Aze-Pab×HOAc
(i) (R,S)-(2-naphthyl)glycolic acid

The sub-title compound was prepared according to the method described in Example 15(i) above from 2-naphthaldehyde (15.6 g; 100 mmol) yielding 12.37 g (61%).

LC-MS m/z 201 (M-1)$^+$, 403 (2M-1)$^-$
$^1$H NMR (500 MHz; CD$_3$OD): δ7.43–7.98 (m, 7 H), 5.29–5.35 (m, 1 H).

(ii) 2-Naphthyl-(R,S)CH(OH)—C(O)-Aze-Pab(Z)

The sub-title compound was prepared according to the method described in Example 3(ii) above from (R,S)-(2-naphthyl)glycolic acid (0.162 g; 0.8 mmol; from step (i) above yielding 266 mg (60%).

LC-MS m/z 551 (M+1)$^+$
$^1$H NMR (400 MHz; CDCl$_3$): δ7.18–7.91 (m, 16 H), 4.86–5.26 (m, 3 H), 4.05–4.60 (m, 3 H), 3.52–3.78 (m, 2H), 2.24–2.73 (m, 2 H).

(iii) 2-Naphthyl-(R,S)CH(OH)—C(O)-Aze-Pab×HOAc

The title compound was prepared according to the method described in Example 15(iii) above from 2-naphthyl-(R,S) CH(OH)—C(O)-Aze-Pab(Z) (0.266 g; 0.48 mmol; from step (ii) above yielding 202 mg (88%).

LC-MS m/z 417 (M+1)$^+$
$^1$H NMR (500 MHz; CD$_3$OD): δ7.28–7.96 (m, 11 H), 5.30–5.40 (m, 1 H), 3.95–4.82 (m, 5 H), 2.09–2.59 (m, 2 H).

Example 32

3-Indolyl-CH$_2$—(R,S)CH(OH)—C(O)-Aze-Pab× HOAc
(i) 3-Indolyl-CH$_2$—(R,S)CH(OH)—C(O)-Aze-Pab(Z)

The sub-title compound was prepared according to the method described in Example 3(ii) above from (R,S)-3-(3-indolyl)lactic acid (0.21 g; 1.0 mmol) yielding 0.22 g (45%).

$^1$H NMR (500 MHz; CDCl$_3$): δ6.57–7.80 (m, 14 H), 5.24 (s, 2 H), 4.59–4.83 (m, 1 H), 4.19–4.51 (m, 3 H), 3.69–3.99 (m, 2 H), 3.03–3.36 (m, 2 H), 2.31–2.56 (m, 2 H).

(ii) 3Indolyl-CH$_2$—(R,S)CH(OH)—C(O)-Aze-Pab×HOAc

The title compound was prepared according to the method described in Example 15(iii) above from 3-indolyl-CH$_2$—(R,S)CH(OH)—C(O)-Aze-Pab(Z) (0.11 g; 0.20 mmol; from step (i) above yielding 75 mg (80%).

FAB-MS m/z 420 (M+1)$^+$
$^1$H NMR (500 MHz; D$_2$O): δ7.00–7.75 (m, 9 H), 4.61–4.71 (m, 1 H), 3.74–4.51 (m, 5 H), 3.00–3.28 (m, 2 H), 1.95–2.42 (m, 2 H).

$^{13}$C NMR (75.5 MHz; D$_2$O; complicated due to diastereomers/rotamers) amidine and carbonyl carbons: δ179.38, 176.19, 175.56, 173.06, 166.78.

Example 33

(CH$_3$)$_2$CH—(R)CH(OH)—C(O)-Aze-Pab×HOAc
(i) (CH$_3$)$_2$CH—(R)CH(OH)—C(O)-Aze-Pab(Z)

The sub-title compound was prepared according to the method described in Example 3(ii) above from (R)-2-hydroxyisovaleric acid (0.12 g; 1.0 mmol) yielding 68 mg (16%).

$^1$H NMR (300 MHz; CDCl$_3$): δ8.25–8.40 (t, NH), 7.15–7.90 (m, 9 H), 5.20 (s, 2 H), 4.85–4.95 (m, 1 H), 4.30–4.55 (m, 2 H), 4.05–4.25 (m, 2 H), 3.75–3.90 (m, 1 H), 1.65–2.75 (m, 3 H), 0.70–1.05 (m, 6 H).

(ii) (CH$_3$)$_2$CH—(R)CH(OH)—C(O)-Aze-Pab×HOAc

The title compound was prepared according to the method described in Example 15(iii) above from (CH$_3$)$_2$CH—(R) CH(OH)—C(O)-Aze-Pab(Z) (0.068 g; 0.15 mmol; froms step (i) above yielding 13 mg (23%).

$^1$H NMR (300 MHz; D$_2$O): δ7.45–7.80 (m, 4 H), 4.85–5.25 (m, 1 H), 4.45–4.65 (m, 2 H), 4.30–4.40 (m, 1 H), 3.80–4.10 (m, 2 H), 2.60–2.80 (m, 1 H), 2.20–2.35 (m, 1 H), 1.90–2.05 (m, 1 H), 0.70–1.00 (m, 6 H).

$^{13}$C NMR (75.5 MHz; D$_2$O; complicated due to rotamers) amidine and carbonyl carbons: 182.37, 176.34, 175.38, 173.84, 173.26, 167.16.

Example 34

(CH₃)₂CH—(CH₂)₂—(R,S)CH(OH)—C(O)-Aze-Pab×HOAc (i) (CH₃)₂CH—(CH₂)₂—(R,S)CH(OH)—C(O)-Aze-Pab(Z)

The sub-title compound was prepared according to the method described in Example 3(ii) above from (R,S)-isoleucic acid (0.12 g; 0.88 mmol) yielding 0.15 g (36%).

¹H NMR (300 MHz; CDCl₃): δ7.15–7.80 (m, 9 H), 5.20 (s, 2 H), 4.85–4.95 (m, 1 H), 4.35–4.55 (m, 2 H), 3.85–4.20 (m, 3 H), 2.40–2.80 (m, 2 H), 1.75–2.10 (m, 1 H), 1.20–1.55 (m, 2 H), 0.75–1.00 (m, 6H).

(ii) (CH₃)₂CH—(CH₂)₂—(R,S)CH(OH)—C(O)-Aze-Pab×HOAc

The title compound was prepared according to the method described in Example 15(iii) above from (CH₃)₂CH—(CH₂)₂—(R,S)CH(OH)—C(O)-Aze-Pab(Z) (0.13 g; 0.27 mmol; from step (i) above) yielding 0.11 g (100%).

¹H NMR (400 MHz; D₂O): δ7.63–7.69 (m, 2 H), 7.37–7.46 (m, 2 H), 4.72–5.12 (m, 1 H), 4.40–4.46 (m, 2 H), 4.17–4.31 (m, 2 H), 3.90–4.02 (m, 1 H), 2.50–2.69 (m, 1 H), 2.11–2.27 (m, 1 H), 1.12–1.72 (m, 3 H), 0.61–0.85 (m, 6 H).

¹³C NMR (75.5 MHz; D₂O; complicated due to diastereomers/rotamers) amidine and carbonyl carbons: δ176.97, 176.80, 176.61, 176.19, 173.38, 173.28, 173.17, 173.10, 166.78, 182.02.

Example 35

Ph(3-OH)—(R,S)CH(OH)—C(O)-Pro-Pab×HCl (i) Boc-Pro-Pab(Z)×HCl

The subtitle compound was prepared according to the method described in Example 1(ii) from Boc-Pro-OH (10.2 g, 47.4 mmol) and added H-Pab(Z)×HCl (15.9 g, 49.8 mmol), yielding 21.74 g (95.5%).

FAB-MS m/z 481 (M+1)⁺

¹H NMR (400 MHz; CD₃OD) δ8.0–7.8 (m, 2H), 7.5–7.25 (m, 7H), 5.17 (s, 2 H), 4.6–4.15 (m, 3H), 3.6–3.35 (m, 2H), 2.3–2.1 (m, 1H), 2.1–1.8 (m, 3H), 1.5–1.3 (two broad singlets, rotamers of Boc, 9H).

(ii) H-Pro-Pab(Z)

The subtitle compound was prepared according to the method described in Example 3(i) from Boc-Pro-Pab(Z)×HCl (from step (ii) above) followed by an alkaline extractive work up.

(iii) Ph(3-OH)—(R,S)CH(OH)—C(O)-Pro-Pab(Z)

The sub-title compound was prepared according to the method described in Example 3(ii) above from (R,S)-3-hydroxymandelic acid (0.25 g; 1.5 mmol) and H-Pro-Pab(Z) (0.63 g; 1.65 mmol; from step (ii) above) yielding 51 mg (6%) of the title compound.

FAB-MS m/z 531 (M+1)⁺

(iv) Ph(3-OH)—(R,S)CH(OH)—C(O)-Pro-Pab×HCl

The title compound was prepared according to the method described in Example 1(v) above from Ph(3-OH)—(R,S)CH(OH)—C(O)-Pro-Pab(Z) (0.05 g; 0.094 mmol; from step (iii) above) yielding 30 mg (74%).

FAB-MS m/z 397 (M+1)⁺

¹³C NMR (75.5 MHz; D₂O; complicated due to diastereomers/rotamers) amidine and carbonyl carbons: δ175.36, 175.13, 172.92, 167.13.

Example 36

Ph(3,5-diOMe)-(R,S)CH(OH)—C(O)-Pro-Pab×HOAc (i) Ph(3,5-diOMe)-(R,S)CH(OH)—C(O)-Pro-Pab(Z)

The sub-title compound was prepared according to the method described in Example 3(ii) above from (R,S)-3,5-dimethoxymandelic acid (0.08 g; 0.38 mmol; prepared according to the method described in Synthesis (1974), 724) and H-Pro-Pab(Z) (0.16 g; 0.42 mmol; see Example 35(ii)) yielding 61 mg (28%).

¹H NMR (500 MHz; CDCl₃): δ7.70–7.80 (t, NH), 7.08–7.50 (m, 9 H), 6.30–6.50 (m, 3 H), 5.20 (s, 2 H), 5.00–5.10 (m, 1 H), 4.25–4.70 (m, 3 H), 3.60–3.80 (m, 6 H), 3.35–3.55 (m, 1 H), 2.95–3.25 (m, 1 H), 1.70–2.25 (m, 4 H).

(ii) Ph(3,5-diOMe)-(R,S)CH(OH)—C(O)-Pro-Pab×HOAc

The title compound was prepared according to the method described in Example 15(iii) above from Ph(3,5-diOMe)-(R,S)CH(OH)—C(O)-Pro-Pab(Z) (0.06 g; 0.10 mmol; from step (i) above) yielding 35 mg (72%).

¹H NMR (500 MHz; D₂O): δ7.23–7.80 (m, 4 H), 6.41–6.65 (m, 3 H), 5.35–5.45 (m, 1 H), 4.35–4.60 (m, 3 H), 3.80 (s, 3 H), 3.10–3.75 (m, 5 H), 1.70–2.35 (m, 4 H).

¹³C NMR (75.5 MHz; D₂O; complicated due to diastereomers/rotamers) amidine and carbonyl carbons: δ175.28, 175.05, 174.03, 173.46, 172.80, 172.73, 167.11, 166.95.

Example 37

Ph(3-OMe)-(R,S)CH(OH)—C(O)-Pro-Pab×HOAc (i) Ph(3-OMe)-(R,S)CH(OH)—C(O)-Pro-Pab(Z)

The sub-title compound was prepared according to the method described in Example 3(ii) above from (R,S)-3-methoxymandelic acid (0.27 g; 1.5 mmol) and H-Pro-Pab(Z) (0.57 g; 1.5 mmol; see Example 35(ii) above) yielding 158 mg (20%).

FAB-MS m/z 545 (M+1)⁺

¹H NMR (400 MHz; CDCl₃): δ7.77–7.84 (m, 2 H), 7.01–7.48 (m, 8 H), 6.80–6.91 (m, 3 H), 5.20–5.24 (m, 2 H), 5.06–5.11 (m, 1 H), 4.30–4.72 (m, 3 H), 3.68–3.79 (m, 3 H), 3.28–3.57 (m, 1 H), 2.91–3.17 (m, 1 H), 1.68–2.31 (m, 4 H).

(ii) Ph(3-OMe)-(R,S)CH(OH)—C(O)-Pro-Pab×HOAc

The title compound was prepared according to the method described in Example 15(iii) above from Ph(3-OMe)-(R,S)CH(OH)—C(O)-Pro-Pab(Z) (0.06 g; 0.11 mmol; from step (i) above yielding 39 mg (75%).

LC-MS m/z 411 (M+1)⁺, 409 (M−1)⁻

¹H NMR (400 MHz; D₂O): δ6.81–7.84 (m, 8 H), 5.47 (s, 1 H), 4.35–4.59 (m, 3 H), 3.60–3.88 (m, 4 H), 3.07–3.29 (m, 1 H), 1.74–2.37 (m, 4 H).

Example 38

Ph(3,4-(—O—CH₂—O—))—(R,S)CH(OH)—C(O)-Aze-Pab×HOAc (i) Ph(3,4-(—O—CH₂—O—))—(R,S)CH(OH)—C(O)-Aze-Pab(Z)

The sub-title compound was prepared according to the method described in Example 3(ii) above from (R,S)-3,4-methylenedioxymandelic acid (0.20 g, 1.0 mmol, prepared according to the method described in Synthesis (1974) 724) yielding 0.22 g (44%).

¹H NMR (400 MHz; acetone-d₆): δ6.68–8.12 (m, 12 H), 5.94–6.05 (m, 2 H), 5.18 (s, 2 H), 3.81–5.12 (m, 6 H), 2.30–2.54 (m, 2 H).

(ii) Ph(3,4-(—O—CH₂—O—))—(R,S)CH(OH)—C(O)-Aze-Pab×HOAc

The title compound was prepared according to the method described in Example 15(iii) above from Ph(3,4-(—O—CH₂—O—))—(R,S)CH(OH)—C(O)-Aze-Pab(Z) (0.11 g; 0.20 mmol; from step (i) above) yielding 72 mg (76%).

¹H NMR (500 MHz; D₂O): δ6.64–7.80 (m, 7 H), 5.91–6.01 (m, 2 H), 4.80–5.25 (m, 2 H), 3.88–4.57 (m, 4 H), 2.11–2.84 (m, 2 H).

$^{13}C$ NMR (75.5 MHz; $D_2O$; complicated due to diastereomers/rotamers) amidine and carbonyl carbons: δ176.03, 175.70, 175.07, 174.82, 168.86.

Example 39

Ph(3-OMe,4-OH)—(R,S)CH(OH)—C(O)-Pro-Pab×HOAc (i) Ph(3-OMe,4-OH)—(R,S)CH(OH)—C(O)-Pro-Pab(Z)

The sub-title compound was prepared according to the method described in Example 3(ii) above from (R,S)-4-hydroxy-3-methoxymandelic acid (0.40 g; 2.0 mmol) and H-Pro-Pab(Z) (0.76 g; 2.0 mmol; see Example 35(ii)) yielding 132 mg (12%).

FAB-MS m/z 561 $(M+1)^+$ $^1H$ NMR (400 MHz; $CDCl_3$): δ6.62–7.84 (m, 12 H), 5.20–5.25 (m, 2 H), 4.15–5.08 (m, 3 H), 3.42–3.84 (m, 4 H), 2.91–3.25 (m, 1 H), 1.66–2.37 (m, 4 H).

(ii) Ph(3-OMe,4-OH)—(R,S)CH(OH)—C(O)-Pro-Pab×HOAc

The title compound was prepared according to the method described in Example 15(iii) above from Ph(3-OMe,4-OH)—(R,S)CH(OH)—C(O)-Pro-Pab(Z) (0.048 g; 0.09 mmol; from step (i) above) yielding 23 mg (55%).

FAB-MS m/z 427 $(M+1)^+$ $^1H$ NMR (400 MHz; $D_2O$): δ6.72–7.83 (m, 7 H), 5.42 (s, 1 H), 4.38–4.68 (m, 3 H), 3.55–4.10 (m, 4 H), 3.09–3.29 (m, 1 H), 1.72–2.37 (m, 4 H).

$^{13}C$ NMR (75.5 MHz; $D_2O$) amidine and carbonly carbons: δ175.12, 173.25, 167.09.

Example 40

Ph-(R,S)C(Et)(OH)—C(O)-Pro-Pab×HOAc (i) Ph-(R,S)C(Et)(OH)—C(O)-Pro-Pab(Z)

The sub-title compound was prepared according to the method described in Example 3(ii) above from (R,S)-2-hydroxy-2-phenyl butanoic acid (0.36 g; 2.0 mmol) and H-Pro-Pab(Z) (0.76 g; 2.0 mmol; see Example 35(ii) above) yielding 57 mg (5%).

FAB-MS m/z 543 $(M+1)^+$ $^1H$ NMR (400 MHz; $CDCl_3$): δ7.24–7.88 (m, 14 H), 5.23 (s, 2 H), 4.44–4.81 (m, 3 H), 2.98–3.25 (m, 2 H), 1.49–2.32 (m, 6 H), 0.85–0.95 (m, 3 H).

(ii) Ph-(R,S)C(Et)(OH)—C(O)-Pro-Pab×HOAc

The title compound was prepared according to the method described in Example 15(iii) above from Ph-(R,S)C(Et)(OH)—C(O)-Pro-Pab(Z) (0.055 g; 0.1 mmol; from step (i) above yielding was 34 mg (72%).

FAB-MS m/z 409 $(M+1)^+$ $^1H$ NMR (400 MHz; $D_2O$): δ7.33–7.82 (m, 9 H), 4.38–4.60 (m, 3 H), 3.19–3.71 (m, 2 H), 1.54–2.34 (m, 6 H), 0.73–0.90 (m, 3 H).

$^{13}C$ NMR (75.5 MHz; $D_2O$; complicated due to diastereomers/rotamers) amidine and carbonyl carbons: δ182.05, 176.42, 175.73, 175.59, 174.70, 174.47, 167.18.

Example 41

Ph(3,5-diMe)-(R,S)CH(OH)—C(O)-Aze-Pab×HOAC (i) (R,S)-3,5-Dimethylmandelic acid

The sub-title compound was prepared according to the method described in Example 15(i) above from 3,5-dimethylbenzaldehyde (5.0 g; 37 mmol) yielding 2.8 g (42%).

$^1H$ NMR (400 MHz; $CD_3OD$): δ7.05 (s, 2 H), 6.94 (s, 1 H), 5.04 (s, 1 H), 2.28 (s, 6 H).

(ii) Ph(3,5-diMe)-(R,S)CH(OH)—C(O)-Aze-Pab(Z)

The sub-title compound was prepared according to the method described in Example 3(ii) from (R,S)-3,5-dimethylmandelic acid (0.27 g; 1.5 mmol; from step (i) above) yielding 0.403 g (51%).

FAB-MS m/z 529 $(M+1)^+$ $^1H$ NMR (500 MHz; $CDCl_3$): δ6.85–7.88 (m, 12 H), 5.22–526 (m, 2 H), 4.84–5.03 (m, 2 H), 4.43–4.62 (m, 2 H), 3.57–4.13 (m, 2 H), 2.25–2.74 (m, 8 H).

(iii) Ph(3,5diMe)-(R,S)CH(OH)—C(O)-Aze-Pab×HOAc

The title compound was prepared according to the method described in Example 15(iii) from Ph(3,5-diMe)-(R,S)CH(OH)—C(O)-Aze-Pab(Z) (0.102 g, 0.194 mmol; from step (ii) above) yielding 74 mg (84%).

FAB-MS m/z 395 $(M+1)^+$ $^1H$-NMR (400 MHz; $D_2O$): δ6.76–7.82 (m, 7 H), 4.80–5.27 (m, 2 H), 3.87–4.62 (m, 4 H), 2.20–2.87 (m, 8 H).

$^{13}C$-NMR (75.5 MHz; $D_2O$; complicated due to diastereomers/rotamers) amidine and carbonyl carbons: δ182.07, 175.60, 174.49, 174.37, 173.96, 173.23, 173.09, 173.05, 172.93, 166.98, 166.90.

Example 42

Ph(3-$NH_2$)—(R,S)CH(OH)—C(O)-Aze-Pab×HOAc (i) Ph(3-$NO_2$)—(R,S)CH(OH)—C(O)-Aze-Pab(Z)

The sub-title compound was prepared according to the method described in Example 3(ii) from (R,S)-3-nitromandelic acid (0.30 g; 1.5 mmol) yielding 0.40 g (48%).

LC-MS m/z 545 $(M+1)^+$ $^1H$ NMR (400 MHz; $CDCl_3$): δ7.16–8.22 (m, 13 H), 5.18–5.23 (m, 2 H), 4.85–5.15 (m, 2 H), 4.08–4.60 (m, 3 H), 3.65–3.81 (m, 1 H), 2.31–2.71 (m, 2 H).

(ii) Ph(3-$NH_2$)—(R,S)CH(OH)—C(O)-Aze-Pab×HOAc

The title compound was prepared according to the method described in Example 15(iii) from Ph(3-$NO_2$)—(R,S)CH(OH)—C(O)-Aze-Pab(Z) (0.102 g; 0.19 mmol; from step (i) above) yielding 0.074 g (89%).

LC-MS m/z 382 $(M+1)^+$ $^1H$-NMR (400 MHz; $D_2O$): δ6.58–7.82 (m, 8 H), 4.80–5.25 (m, 2 H), 3.60–4.60 (m, 4 H), 2.12–2.88 (m, 2 H).

$^{13}C$ NMR (75:5 MHz; $D_2O$; complicated due to diastereomers/rotamers) amidine and carbonyl carbons: δ181.96, 175.27, 174.25, 173.84, 173.19, 173.01, 166.93.

Example 43

Ph(3-$NO_2$)—(R,S)CH(OH)—C(O)-Aze-Pab×HOAc

Anisole (0.030 g; 0.27 mmol) and trifluoromethanesulfonic acid (0.138 g; 0.92 mmol) was added to a mixture of Ph(3-$NO_2$)—(R,S)CH(OH)—C(O)-Aze-Pab(Z) (0.100 g; 0.18 mmol; see Example 42(i) above) and $CH_2Cl_2$ (10 ml). The reaction mixture was stirred at room temperature for 10 minutes. $H_2O$ was added and the pH was adjusted to 9 with $Na_2CO_3$/aq. The $CH_2Cl_2$ was removed in vacuo and the remaining $H_2O$-layer was extracted with diethylether (3×5 ml) followed by freeze drying. The crude product was subjected to preparative RPLC yielding 62 mg (60%) of the title compound after freeze drying.

$^1H$ NMR (400 MHz; $D_2O$): δ7.38–8.31 (m, 8 H), 4.83–5.50 (m, 2 H), 4.03–4.57 (m, 4 H), 2.17–2.86 (m, 2 H).

$^{13}C$ NMR (75.5 MHz; $D_2O$; complicated due to diastereomers/rotamers) amidine and carbonyl carbons: δ181.5, 173.84, 173.39, 173.15, 173.04, 172.96, 172.80, 166.85.

Example 44

Ph(3-NH$_2$)—(R,S)CH(OH)—C(O)-Pro-Pab×HOAc
(i) Ph(3-NO$_2$)—(R,S)CH(OH)—C(O)-Pro-Pab(Z)

The sub-title compound was prepared according to the method described in Example 3(ii) from (R,S)-3-nitromandelic acid (0.30 g; 1.5 mmol) and H-Pro-Pab(Z)× 2HCl (0.75 g; 1.65 mmol; see Example 35(ii) above) yielding 0.61 g (73%).

LC-MS m/z 560 (M+1)$^+$
$^1$H-NMR (400 MHz; CDCl$_3$): δ7.26–8.23 (m, 13 H), 5.20–5.28 (m 3 H), 4.33–4.73 (m, 3 H), 3.46–3.68 (m, 1 H), 2.92–3.14 (m, 1 H), 1.79–2.33 (m, 4 H).
(ii) Ph(3-NH$_2$)—(R,S)CH(OH)—C(O)-Pro-Pab×HOAc

The title compound was prepared according to the method described in Example 15(iii) from Ph(3-NO$_2$)—(R,S)CH(OH)—C(O)-Pro-Pab(Z) (0.104 g; 0.19 mmol; from step (i) above) yielding 64 mg (76%).

LC-MS m/z 396 (M+1)$^+$
$^1$H-NMR (400 MHz; D$_2$O): δ6.74–7.82 (m, 8 H), 5.34–5.40 (m, 1 H), 4.35–4.58 (m, 3 H), 3.09–3.78 (m, 2 H), 1.75–2.35 (m, 4 H).
$^{13}$C-NMR (75.5 MHz; D$_2$O; complicated due to diastereomers/rotamers) amidine and carbonyl carbons: δ182.04, 175.38, 175.18, 173.12, 173.04, 167.07.

Example 45

Ph(3-NO$_2$)—(R or S)CH(OH)—C(O)-Pro-Pab× HOAc

The title compound was prepared according to the method described in Example 43 from Ph(3-NO$_2$)—(R,S)CH(OH)—C(O)-Pro-Pab(Z) (0.117 g; 0.21 mmol; see Example 44(i) above). Some fractions were concentrated to give 23 mg (45%) of a compound with a diastereomeric ratio of >99:1.

LC-MS m/z 424 (M−1)$^-$; 426 (M+1)$^+$
$^1$H-NMR (500 MHz; D$_2$O): δ7.31–8.35 (m, 8 H), 5.50–5.71 (m, 1 H), 3.64–4.57 (m, 4 H), 3.24–3.32 (m, 1 H) 1.76–2.42 (m, 4 H).
$^{13}$C NMR (75.5 MHz; D$_2$O; complicated due to rotamers) amidine and carbonyl carbons: δ175.21, 173.98, 172.58, 172.18, 167.12, 166.82.

(Earlier fractions were concentrated to give 22 mg (43%) of the epimer of the above compound with a diastereomeric ratio of >99:1).

Example 46

Ph(3,4(—O—CH$_2$—O—))—(R,S)CH(OH)—C(O)-Pro-Pab×HCl
(i) Ph(3,4-(—O—CH$_2$—O—))—(R,S)CH(OH)—C(O)-Pro-Pab(Z)

The sub-title compound was prepared according to the method described in Example 3(ii) above from (R,S)-3,4-methylenedioxymandelic acid (0.20 g, 1.0 mmol, prepared according to the method described in Synthesis (1974) 724) and H-Pro-Pab(Z)×2HCl (0.35 g; 0.91 mmol; see Example 35(ii) above) yielding 80 mg (16%).

FAB-MS m/z 559 (M+1)$^+$
$^1$H-NMR (500 MHz; CDCl$_3$): δ6.69–7.89 (m, 12 H), 5.91–6.04 (m, 2 H), 4.30–5.28 (m, 2 H), 3.00–3.61 (m, 6 H), 1.95–2.35 (m, 4 H).
(ii) Ph(3,4-(—O—CH$_2$—O—))—(R,S)CH(OH)—C(O)-Pro-Pab×HCl

The title compound was prepared according to the method described in Example 1(v) above from Ph(3,4-(—O—CH$_2$—O—))—(R,S)CH(OH)—C(O)-Pro-Pab(Z) (0.08 g; 0.14 mmol; from step (i) above) yielding 48 mg (73%).

FAB-MS m/z 425 (M+1)$^+$
$^1$H-NMR (500 MHz; D$_2$O): δ6.81–7.85 (m, 7 H), 5.90–6.05 (m, 2 H), 5.33–5.44 (m, 1 H), 4.37–4.90 (m, 3 H), 3.62–3.77 (m, 1H), 3.13–3.28 (m, 1 H), 1.80–2.36 (m, 4 H).
$^{13}$C NMR (75.5 MHz; D$_2$O; complicated due to diastereomers/rotamers) amidine and carbonyl carbons: δ175.37, 175.09, 173.66, 173.08, 173.00, 167.03.

Example 47

Ph(3,5-diF)-(R,S)CH(OH)—C(O)-Pro-Pab×HOAc
(i) Ph(3,5-diF)-(R,S)CH(OH)—C(O)-Pro-Pab(Z)

The sub-title compound was prepared according to the method described in Example 3(ii) above from (R,S)-3,5-difluoromandelic acid (0.28 g; 1.5 mmol) and H-Pro-Pab(Z)×2HCl (0.75 g; 1.65 mmol; see Example 35(ii) above) yielding 0.42 g (51%).

LC-MS m/z 549 (M−1)$^-$; 551 (M+1)$^+$
$^1$H-NMR (400 MHz; CDCl$_3$): δ6.72–7.84 (m, 12 H), 5.22 (s, 2 H), 5.08 (s, 1), 4.34–4.73 (m, 3 H), 3.41–3.60 (m, 1 H), 2.96–3.19 (m, 1 H), 1.80–2.34 (m, 4 H).
(ii) Ph(3,5diF)-(R,S)CH(OH)—C(O)-Pro-Pab×HOAc

The title compound was prepared according to the method described in Example 15(iii) above from Ph(3,5-diF)-(R,S)CH(OH)—C(O)-Pro-Pab(Z) (0.104 g; 0.19 mmol; from step (i) above) yielding 79 mg (88%).

LC-MS m/z 415 (M−1)$^-$; 417 (M+1)$^+$
$^1$H NMR (400 MHz; D$_2$): δ6.86–7.80 (m, 7 H), 5.50 (s, 1 H), 3.58–4.72 (m, 4 H), 3.19–3.32 (m, 1 H), 1.80–2.37 (m, 4 H).
$^{13}$C NMR (75.5 MHz; D$_2$O; complicated due to diastereomers/rotamers) amidine and carbonyl carbons: δ181.87, 175.21, 174.98, 174.12, 172.57, 172.12, 171.97, 167.10, 165.24.

Example 48

Ph-(R)CH(O—CH$_2$—(R,S)CH(OH)—CH$_2$OH)—C(O)-Aze-Pab×HOAc
(i) Ph-(R)CH(OH)—C(O)OBn (R)-Mandelic acid (3.0 g, 19.7 mmol) was dissolved in DMF (50 ml) and cesium carbonate (3.21 g, 9.86 mmol) was added. The reaction mixture was stirred at room temperature overnight The mixture was diluted with H$_2$O (200 ml) and the H$_2$O-layer was extracted with EtOAc. After separation the organic layer was washed with NaCl/aq, dried (Na$_2$SO$_4$) and evaporated. The yield of the sub-title compound was 4.2 g (88%).

LC-MS m/z 265 (M+Na)$^+$
$^1$H-NMR (400 MHz; CDCl$_3$): δ7.17–7.44 (m, 10 H), 5.12–5.27 (m, 3 H).
(ii) Ph-(R)CH(O—CH$_2$—CH=CH$_2$)—C(O)OBn

A mixture of Ph-(R)CH(OH)—C(O)OBn (1.0 g; 4.13 mmol; from step (i) above), magnesium sulphate (0.1 g; 0.83 mmol) and silver (I) oxide (2.58 g; 11.2 mmol) in petroleum ether (bp 40–60° C.; 25 ml) was stirred at room temperature in nitrogen atmosphere and darkness. Allyl bromide (0.75 g; 6.19 mmol) was added dropwise followed by silver (I) oxide (2.58 g; 11.2 mmol) in two portions. The reaction mixture was stirred at room temperature overnight. The mixture was subsequently filtered through celite and the filtrate was evaporated yielding 1.143 g (98%) of the sub-title compound.

$^1$H-NMR (500 MHz; CDCl$_3$): δ7.20–7.50 (m, 10), 5.89–5.99(m, 1 H), 5.09–5.31 (m, 4 H), 4.99 (s, 1 H), 4.03–4.11 (m, 2 H).

(iii) Ph-(R)CH(O—CH$_2$—(R,S)CH(OH)—CH$_2$OH)—C(O)OBn

A mixture of Ph-(R)CH(O—CH$_2$—CH=CH$_2$)—C(O)OBn (0.74 g; 2.62 mmol; from step (ii) above), N-methylmorpholine-N-oxide (0.425 g; 3.15 mmol) and osmium tetroxide (0.0027 g; 0.01 mmol) in H$_2$O: acetone (2:1; 10 ml) was stirred at room temperature for 2 days. Sodium pyrosulfite (1.5 g; 7.89 mmol) was added and the mixture was stirred for 1 h. The reaction mixture was subsequently filtered through celite and the filtrate was evaporated. The yield of the subtitle compound was 0.51 g (62%).

$^1$H-NMR (400 MHz; CDCl$_3$): δ7.16–7.44 (m, 10 H), 5.09–5.20 (m, 2 H), 4.96 (s, 1 H), 3.55–3.97 (m, 5 H).

(iv) Ph-(R)CH(O—CH$_2$—(R,S)CH(—O—C(CH$_3$)$_2$—O—CH$_2$—))—C(O)OBn

Ph-(R)CH(O—CH$_2$—(R,S)CH(OH)—CH$_2$OH)—C(O)OBn (0.51 g; 1.61 mmol; from step (iii) above) was dissolved in acetone (20 ml). p-Toluenesulfonic acid monohydrate (0.007 g, 0.037 mmol) was added and the mixture was stirred at room temperature for 24 h. Potassium carbonate (0.09 g) was added and the reaction mixture was stirred at room temperature for 1 h. The mixture was subsequently filtered through celite and the filtrate was evaporated yielding 0.559 g (97%) of the sub-title compound.

$^1$H-NMR (400 MHz; CDCl$_3$): δ7.18–7.48 (m, 10 H), 5.01–5.21 (m, 3 H), 4.27–4.40 (m, 1 H), H), 4.02–4.11 (m, 1 H), 3.76–3.90 (m, 1 H), 3.49–3.67 (m, 2 H), 1.34–1.41 (m, 6 H).

(v) Ph-(R)CH(O—CH$_2$—(R,S)CH(—O—C(CH$_3$)$_2$—O—CH$_2$—))—C(O)OH

Ph-(R)CH(O—CH$_2$—(R,S)CH(—O—C(CH$_3$)$_2$—O—CH$_2$—))—C(O)OBn (0.183 g; 0.51 mmol; from step (iv) above) was dissolved in ethanol (10 ml). Pd/C (5%; 0.09 g) was added and the reaction mixture was hydrogenated at atmospheric pressure for 1 h The mixture was subsequently filtered through celite and the filtrate was evaporated yielding 0.137 g (100%) of the sub-title compound LC-MS m/z 265 (M−1)$^-$ $^1$H-NMR (400 MHz; CD$_3$OD): δ7.28–7.48 (m, 5 H), 4.97 (s, 1 H), 4.25–4.35 (m, 1 H), 4.01–4.09 (m, 1 H), 3.72–3.84 (m, 1 H), 3.43–3.65 (m, 2 H), 1.30–1.37 (m, 6 H).

(vi) Ph-(R)CH(O—CH$_2$—(R,S)CH(—O—C(CH$_3$)$_2$—O—CH$_2$—))—C(O)-Aze-Pab(Z)

The sub-title compound was prepared according to the method described in Example 3(ii) above from Ph-(R)CH(O—CH$_2$—(R,S)CH(—O—C(CH$_3$)$_2$—O—CH$_2$—))—C(O)OH (0.165 g; 0.62 mmol; from step (v) above) yielding 0.20 g (52%).

LC-MS m/z 613 (M−1)$^-$; 615 (M+1)$^+$ $^1$H-NMR (500 MHz; CDCl$_3$): δ7.22–7.88 (m, 14 H), 5.22 (s, 2 H), 4.87–4.95 (m, 2 H), 3.40–4.54 (m, 9 H), 2.36–2.76 (m, 2 H), 1.22–1.42 (m, 6 H).

(vii) Ph-(R)CH(O—CH$_2$—(R,S)CH(—O—C(CH$_3$)$_2$—O—CH$_2$—))—C(O)-Aze-Pab×HOAc

The title compound was prepared according to the method described in Example 15(iii) above from Ph-(R)CH(O—CH$_2$—(R,S)CH(—O—C(CH$_3$)$_2$—O—CH$_2$—))—C(O)-Aze-Pab(Z) (0.20 g; 0.325 mmol; from step (vi) above) yielding 179 mg (100%).

LC-MS m/z 479 (M−1)$^-$, 481 (M+1)$^+$ $^1$H-NMR (500 MHz; D$_2$O): δ7.33–7.80 (m, 9 H), 4.81–5.31 (m, 2 H), 3.94–4.59 (m, 6 H), 3.25–3.80 (m 3 H), 2.16–2.88 (m, 2 H), 1.29–1.44 (m, 6 H).

$^{13}$C-NMR (75.5 MHz; D$_2$O; complicated due to diastereomers/rotamers) amidine and carbonyl carbons: δ181.99, 173.12, 172.93, 172.18, 166.84.

(viii) Ph-(R)CH(O—CH$_2$—(R,S)CH(OH)—CH$_2$OH)—C(O)-Aze-Pab×HOAc

Ph-(R)CH(O—CH$_2$—(R,S)CH(—O—C(CH$_3$)$_2$—O—CH$_2$—))-C(O)-Aze-Pab×HOAc (0.094 g; 0.17 mmol; from step (vii) above) was dissolved in HOAc:H$_2$O (4:1; 10 ml) and the reaction is mixture was stirred at room temperature for 24 h. The mixture was evaporated and the residue was dissolved in H$_2$O and freeze dried. The yield of the title compound was 85 mg (100%).

LC-MS m/z 439 (M−1)$^-$, 441 (M+1)$^+$ $^1$H-NMR (500 MHz; D$_2$O): δ7.32–7.78 (m, 9 H), 4.81–5.28 (m, 2 H), 3.28–4.56 (m, 9 H), 2.15–2.90 (m, 2 H).

$^{13}$C-NMR (100.6 MHz; D$_2$O; complicated due to diastereomers/rotamers) amidine and carbonyl carbons: δ179.14, 172.93, 172.89, 172.51, 171.96, 166.54.

Example 49

Ph-(R)CH(O—CH$_2$—(R,S)CH(OH)—CH$_2$OH)—C(O)-Pro-Pab×HOAc (i) Ph-(R)CH(O—CH$_2$(R,S)CH(—O—C(CH$_3$)$_2$—O—CH$_2$—))—C(O)-Pro-Pab(Z)

The sub-title compound was prepared according to the method described in Example 3(ii) above from Ph-(R)CH(O—CH$_2$(R,S)CH(—O—C(CH$_3$)$_2$—O—CH$_2$—))—C(O)OH (0.108 g; 0.4 mmol; see Example 48(v) above) and H-Pro-Pab(Z)×2HCl (0.202g; 0.46 mmol; see Example 35(ii) above), yielding 0.10 g (40%).

LC-MS m/z 627 (M−1)$^-$; 629 (M+1)$^+$; 651 (M+Na)$^+$ $^1$H-NMR (500 MHz; CDCl$_3$): δ7.23–7.87 (m, 14 H), 5.03–5.27 (m, 3 H), 3.34–4.64 (m, 10 H), 1.71–2.39 (m, 4 H), 1.23–1.41 (m, 6H).

(ii) Ph-(R)CH(O—CH$_2$—(R,S)CH(—O—C(CH$_3$)$_2$—O—CH$_2$—))—C(O)-Pro-Pab×HOAc

The sub-title compound was prepared according to the method described in Example 15(iii) above from Ph-(R)CH(O—CH$_2$—(R,S)CH(—O—C(CH$_3$)$_2$—O—CH$_2$—))—C(O)-Pro-Pab(Z) (0.100 g; 0.159 mmol; from step (i) above yielding 85,mg (96%).

LC-MS m/z 493 (M−1)$^-$, 495 (M+1)$^+$ $^1$H-NMR(500 MHz; D$_2$O): δ7.30–7.82 (m, 9 H), 5.22–5.38 (m, 1 H), 4.32–4.62 (m, 4 H), 4.01–4.11 (m, 1 H), 3.22–3.83 (m, 5H),1.78–2.22 (m, 4H), 1.33–1.44 (m, 6 H).

$^{13}$C-NMR (100.6 MHz; D$_2$O; complicated due to diastereomers/rotamers) amidine and carbonyl carbons: δ181.47, 174.74, 173.53, 171.64, 171.50, 171.00, 170.94, 166.58.

(iii) Ph-(R)CH(O—CH$_2$—(R,S)CH(OH)—CH$_2$OH)—C(O)-Pro-Pab×HOAc

The title compound was prepared according to the method described in Example 48(viii) above from Ph-(R)CH(O—CH$_2$—(R,S)CH(—O—C(CH$_3$)$_2$—O—CH$_2$—)—C(O)-Pro-Pab×HOAc (0.038 g; 0.069 mmol; from step (ii) above) yielding 35 mg (98%).

LC-MS m/z 453 (M−1)$^-$; 455 (M+1)$^+$ $^1$H-NMR (500 MHz; D$_2$O): δ7.30–7.82 (m, 9 H), 5.20–5.38 (m, 1 H), 3.18–4.60 (m, 10 H), 1.70–2.38 (m, 4 H).

$^{13}$C-NMR (100.6 MHz; D$_2$O; complicated due to diastereomers/rotamers) amidine and carbonyl carbons: δ180.26, 174.74, 173.47, 171.80, 171.26, 166.61.

Example 50

Ph-(R or S)C(—O—C(CH$_3$)$_2$—O—CH$_2$—)—C(O)-Aze-Pab×HOAc and Ph-(S or R)C(—O—C(CH$_3$)$_2$—C(O)-Aze-Pab×HOAc (i) Ph-(R,S)C(—O—C(CH$_3$)$_2$—O—CH$_2$—)—C(O)OH The sub-title compound was prepared analogously to the method described in Example 48(iv) above from α-hydroxytropic acid (3.5 g; 20.35 mmol; prepared according to Guthrie et al., Can. J. Chem. (1991) 69, 1904) yielding 3.37 g (74%).

$^1$H-NMR (500 MHz; CDCl$_3$): δ7.30–7.65 (m, 5 H), 4.95 (d, 1 H), 4.10 (d, 1 H), 1.70 (s, 3H), 1.50 (s, 3 H).

(ii) Ph-(R,S)C(—O—C(CH$_3$)$_2$—O—CH$_2$—)—C(O)-Aze-Pab(Z)

The sub-title compound was prepared according to the method described in Example 3(ii) above from Ph-(R,S)C(—O—C(CH$_3$)$_2$—O—CH$_2$—)—C(O)OH (0.25 g; 1.12 mmol; from step (i) above) yielding 0.30 g (53%).

$^1$H-NMR (400 MHz; CDCl$_3$): δ7.20–7.90 (m, 14 H), 5.22 (s, 2 H), 3.70–5.10 (m, 7 H), 2.15–2.75 (m, 2 H), 1.40–1.65 (m, 6 H).

(iii) Ph-(R or S)C(—O—C(CH$_3$)$_2$—O—CH$_2$—C(O)-Aze-Pab×HOAc and Ph-(S or R)C(—O—C(CH$_3$)$_2$—O—CH$_2$—)—C(O)-Aze-Pab×HOAc A mixture of Ph-(R,S)C(—O—C(CH$_3$)$_2$—O—CH$_2$—)—C(O)-Aze-Pab(Z) (0.30 g; 0.53 mmol; from step (ii) above), ammonium formate (0.30 g, 4.76 mmol), formic acid (3 drops) and Pd/C (5%, 0.30 g) in methanol (10 ml) was stirred at room temperature for 30 minutes. The reaction mixture was filtered through celite and the filtrate was evaporated. The crude product (0.29 g) was subjected to preparative RPLC. Some fractions were concentrated to give 80 mg (35%) of compound 50A with a diastereomeric ratio>99:1. Later fractions were concentrated to give 80 mg (35%) of compound 50B with a diastereomeric ratio of 98:2.

Compound 50A:
LC-MS m/z 437 (M+1)$^+$
$^1$H NMR (400 MHz; CD$_3$OD): δ7.28–7.85 (m, 9 H), 3.70–4.95 (m, 7 H), 2.10–2.55 (m, 2 H), 1.55 (s, 3 H), 1.50 (s, 3 H).

Compound 50B:
LC-MS m/z 437 (M+1)$^+$
$^1$H-NMR (400 MHz; CD$_3$OD): δ7.25–7.80 (m, 9 H), 3.70–5.00 (m, 7 H), 2.25–2.45 (m, 2 H), 1.60 (s, 3 H), 1.48 (s, 3 H).

Example 51

Ph-(R or S)C(OH)(CH$_2$OH)—C(O)-Aze-Pab×HCl and Ph-(S or R)C(OH)(CH$_2$OH)—C(O)-Aze-Pab×HCl (i) Ph-(R or S)C(OH)(CH$_2$OH)—C(O)-Aze-Pab×HCl Ph-(R or S)C(—O—C(CH$_3$)$_2$—O—CH$_2$—)—C(O)-Aze-Pab×HOAc (0.060 g; 0.12 mmol; compound 50A from Example 50 above) was dissolved in acetic acid (4 ml) and H$_2$O (1 ml) was added. The mixture was stirred at room temperature overnight followed by stirring at 90° C. for 6 h HCl (conc.; 1 ml) was added and the mixture was stirred at room temperature for 5 minutes. The acetic acid and HCl were removed in vacua in the presence of toluene and EtOH and the residue was dissolved in H$_2$O (4 ml) and freeze dried. The crude product was subjected to preparative RPLC to give 9 mg (16%) of the title compound.

LC-MS m/z 395 (M−1)$^-$, 397 (M+1)$^+$
$^1$H-NMR (400 MHz; CD$_3$OD): δ7.20–7.85 (m, 9 H), 3.90–4.70 (m, 5 H), 3.30–3.70 (m, 2 H), 2.00–2.65 (m, 2 H).

(ii) Ph-(S or R)C(OH)(CH$_2$OH)—C(O)-Aze-Pab×HCl

The title compound was prepared according to the method described in step (i) above from Ph-(S or R)C(—O—C(CH$_3$)$_2$—O—CH$_2$—)—C(O)-Aze-Pab×HOAc (0.060 g; 0.12 mmol; compound 50B from Example 50 above) yielding 22 mg (40%).

LC-MS m/z 397 (M+1)$^+$
$^1$H-NMR (400 MHz; CD$_3$OD): δ7.20–7.85 (m, 9 H), 3.90–4.75 (m, 6 H), 3.50–3.60 (m, 1 H), 2.10–2.50 (m, 2 H).

Example 52

Ph-(R or S)C(—O—C(CH$_3$)$_2$—O—CH$_2$—)—C(O)-Pro-Pab×HOAc and Ph-(S or R)C(—O—C(CH$_3$)$_2$—O—CH$_2$—)—C(O)-Pro-Pab×HOAc (i) Ph-(R,S)C(—O—C(CH$_3$)$_2$—O—CH$_2$—)—C(O)-Pro-Pab(Z)

The sub-title compound was prepared according to the method described in Example 3(ii) above from Ph-(R,S)C(—O—C(CH$_3$)$_2$—O—CH$_2$—)—C(O)OH (0.25 g; 1.12 mmol; see Example 50(i) above) yielding 0.19 g (32%).

FAB-MS m/z 585 (M+1)$^+$
$^1$H-NMR (400 MHz; CDCl$_3$): δ7.20–7.95 (m, 14 H), 5.25 (s, 2 H), 5.10–5.20 (m, 1 H), 4.32–4.70 (m, 3 H), 3.65–3.95 (m, 2 H), 3.00–3.25 (m, 1 H), 1.30–2.35 (m, 10 H).

(ii) Ph-(R or S)C(—O—C(CH$_3$)$_2$—O—CH$_2$—)—C(O)-Pro-Pab×HOAc and Ph-(S or R)C(—O—C(CH$_3$)$_2$—O—CH$_2$—)—C(O)-Pro-Pab×HOAc The title compounds were prepared according to the method described in Example 50(iii) above from Ph-(R,S)C(—O—C(CH$_3$)$_2$—CH$_2$—)—C(O)-Pro-Pab(Z) (0.37 g; 0.63 mmol; from step (i) above). Some fractions were concentrated to give 120 mg of compound 52A with a diastereomeric ratio>99:1. Later fractions were concentrated to give 120 mg of compound 52B with a diastereomeric ratio of 98:2.

Compound 52A:
LC-MS m/z 451 (M+1)$^+$
$^1$H-NMR (400 MHz; CD$_3$OD): δ7.25–7.80 (m, 9 H), 4.35–5.05 (m, 4 H), 3.80–3.95 (m, 1 H), 3.60–3.65 (m, 1 H), 3.00–3.10 (m, 1 H), 2.10–2.20 (m, 1 H), 1.75–1.90 (m, 3 H), 1.55 (s, 3 H), 1.45 (s, 3H).

Compound 52B:
LC-MS m/z 451 (M+1)$^+$
$^1$H-NMR (400 MHz; CD$_3$OD): δ7.25–7.80 (m, 9 H), 4.40–5.10 (m, 4 H), 3.30–3.80 (m, 3 H), 1.75–2.20 (m, 4 H), 1.50–1.55 (m, 6 H).

Example 53

Ph-(R or S)C(OH)(CH$_2$OH)—C(O)-Pro-Pab×HCl and Ph-(S or R)C(OH)(CH$_2$OH)—C(O)-Pro-Pab×HCl (i) Ph-(R or S)C(OH)(CH$_2$OH)—C(O)-Pro-Pab×HCl The title compound was prepared according to the method described in Example 51(i) above from Ph-(R or S)C(—O—C—CH$_3$)$_2$—O—CH$_2$—C(O)-Pro-Pab×HOAc (0.060 g; 0.12 mmol; compound 52A from Example 52 above) yielding 2 mg (2%).

LC-MS m/z 409 (M−1)$^-$, 411 (M+1)$^+$
$^1$H-NMR (400 MHz; CD$_3$OD): δ7.20–7.85 (m, 9 H), 4.40–4.60 (m, 3 H), 4.05–4.30 (m, 1 H), 2.95–3.90 (m, 3 H), 1.60–2.20 (m, 4 H).

(ii) Ph-(S or R)C(OH)(CH$_2$OH)—C(O)-Pro-Pab×HCl

The title compound was prepared according to the method described in Example 51(i) above from Ph-(S or R)C(—O—C(CH$_3$)$_2$—O—CH$_2$—)—C(O)-Pro-Pab×HOAc (0.060 g; 0.12 mmol; compound 52B from Example 52 above) yielding 1 mg (1%).

LC-MS m/z 409 (M−1)⁻; 411 (M+1)⁺

¹H-NMR (400 MHz; CD₃OD): δ7.25–7.85 (m,9 H), 4.40–4.65 (m, 3 H), 4.05–4.20 (m, 1 H), 3.25–3.75 (m, 3 H), 1.40–2.20 (m, 4 H).

Example 54

Ph-(R)C(Me)(OH)—C(O)-Pro-Pab×HCl (i) Ph-(R)C(Me)(OH)—C(O)-Pro-Pab(Z)

The sub-title compound was prepared according to the method described ir Example 3(ii) above from (R)-(−)-2-hydroxy-2-phenylpropionic acid (0.20 g; 1.2 mmol) and H-Pro-Pab(Z)×2HCl (0.50 g; 1.1 mmol; see Example 35(ii) above) yielding 0.13 g (22%).

¹H-NMR (500 MHz; CDCl₃): δ7.18–7.87 (m, 14 H), 5.25 (s, 2 H), 4.37–4.61 (m, 3 H), 3.03–3.19 (m, 2 H), 1.50–2.17 (m, 7 H).

(ii) Ph-(R)C(Me)(OH)—C(O)-Pro-Pab×HCl

The title compound was prepared analogously to the method described in Example 1(v) above from Ph-(R)C(Me)(OH)—C(O)-Pro-Pab(Z) (0.13 g; 0.25 mmol; from step (i) above) yielding 94 mg (89%).

FAB-MS m/z 395 (M+1)⁺

¹H-NMR (500 MHz; D₂O): δ7.37–7.91 (m, 9 H), 4.33–4.61 (m, 3 H), 3.15–4.01 (m, 2 H), 1.72–2.33 (m, 7 H).

¹³C-NMR (75.5 MHz; D₂O; complicated due to rotamers) amidine and carbonyl carbons: 176.06, 175.49, 174.88, 166.90.

Example 53

Ph-(S)C(Me)(OH)—C(O)-Pro-Pab×HCl (i) Ph-(S)C(Me)(OH)—C(O)-Pro-Pab(Z)

The sub-title compound was prepared according to the method described in Example 3(ii) above from (S)-(+)-2-hydroxy-2-phenylpropionic acid (0.20 g; 1.2 mmol) and H-Pro-Pab(Z)×2HCl (0.50 g; 1.1 mmol; see Example 35(ii) above) yielding 0.19 g (33%).

¹H-NMR (500 MHz; CDCl₃): δ7.20–7.77 (m, 14 H), 5.22 (s, 2 H), 4.53–4.58 (m, 1 H), 4.32–4.44 (m, 2 H), 3.13–3.38 (m, 2 H), 1.53–2.04 (m, 7 H).

(ii) Ph-(S)C(Me)(OH)—C(O)-Pro-Pab×HCl

The title compound was prepared according to the method described in Example 1(v) above from Ph-(S)C(Me)(OH)—C(O)-Pro-Pab(Z) (0.12 g; 0.23 mmol; from step (i) above) is yielding 80 mg (822%).

FAB-MS m/z 395 (M+1)⁺

¹H-NMR (500 MHz; D₂O): δ7.35–7.84 (m, 9 H), 4.47–4.63 (m, 3 H), 3.30–3.70 (m, 2 H), 1.60–2.29 (m, 7 H).

¹³C-NMR (75.5 MHz; D₂O; complicated due to rotamers) amidine and carbonyl carbons: δ175.58, 175.23, 174.79, 167.07.

Example 56

Ph(3,4-diF)-(R,S)CH(OH)—C(O)-Pro-Pab×HCl (i) Ph(3,4-diF)-(R,S)CH(OH)—C(O)-Pro-Pab(Z)

The sub-title compound was prepared according to the method described in Example 3(ii) above from (R,S)-3,4-difluoromandelic acid (0.20 g; 1.06 mmol) and H-Pro-Pab(Z)×2 HCl (0.53 g; 1.17 mmol; see Example 35(ii) above) yielding 445 mg (76%).

LC-MS m/z 549 (M−1)⁻; 551 (M+1)⁺

¹H-NMR (400 MHz; CDCl₃): δ6.98–7.74 (m, 12 H), 5.16–5.21 (m, 2 H), 5.06–5.01 (m, 1 H), 4.22–4.56 (m, 3 H), 3.32–3.58 (m, 1 H), 2.88–3.12 (m, 1 H), 1.70–2.12 (m, 4 H).

(ii) Ph-(3,4-diF)-(R,S)CH(OH)—C(O)-Pro-Pab×HCl

The title compound was prepared according to the method described in Example 1(v) above from Ph(3,4-diF)-(R,S)CH(OH)—C(O)-Pro-Pab(Z) (0.175 g; 0.31 mmol; from step (i) above) yielding 127 mg (88%).

LC-MS m/z 417 (M+1)⁺

¹H-NMR (400 MHz; CD₃OD): δ7.11–7.86 (m, 7 H), 5.37 (s, 1 H), 4.36–5.00 (m, 4 H), 3.66–3.78 (m, 1 H), 1.80–2.31 (m, 4 H).

¹³C-NMR (100.6 MHz; D₂O; complicated due to diastereomerslrotamers) amidine and carbonyl carbons: δ174.66, 174.40, 171.96, 171.82, 166.48.

Example 57

Ph-(R)CH(OH)—C(O)—(R,S)Pic(4-oxo)-Pab× HOAc (i) Boc-(R,S)Pic(4-oxo)-OCH₃

A mixture of Boc-(R,S)Pic(4-hydroxy)OCH₃ (1.1 g; 4.25 mmol; prepared according to Gillard et al., J. Org. Chem., (1996) 61, 2226), PCC (1.8 g; 8.5 mmol) and molecular sieves (powdered; 3 Å; 1.0 g) in CH₂Cl₂ (20 ml) was stirred at room temperature for 4 h. Diethyl ether (60 ml) was added and the reaction mixture was filtered through a short silica gel column eluted with EtOAc:Hexane (1:1). The filtrate was evaporated yielding 1.0 g (92%) of the sub-title compound.

FAB-MS m/z 258 (M+1)⁺

¹H-NMR (500 MHz; CDCl₃): δ4.75–5.20 (m, 1 H), 3.55–4.15 (m, 5 H), 2.40–2.90 (m, 4 H), 1.30–1.65 (m, 9 H).

(ii) H—(R,S)Pic(4-oxo)-OCH₃

Boc-(R,S)Pic(4-oxo)-OCH₃ (0.48 g; 1.87 mmol; from step (i) above) was treated with trifluoroacetic acid in CH₂Cl₂ (50%, 4 ml) at room temperature for 30 minutes. The reaction mixture was evaporated and the residue was dissolved in CH₂Cl₂, washed with Na₂CO₃/aq, dried (K₂CO₃) and evaporated. The yield of the sub-title compound was 0.23 g (78%).

¹H-NMR (500 MHz; CDCl₃): δ3.65–3.80 (m, 4 H), 3.30–3.40 (m, 1 H), 2.90–3.00 (m, 1 H), 2.30–2.70 (m, 4 H).

(iii) Ph-(R)CH(OTBDMS)-C(O)—(R,S)Pic(4-oxo)-OCH₃

The sub-title compound was prepared analogously to the method described in Example 3(ii) above from H—(R,S)Pic(4-oxo)-OCH₃ (0.22 g; 1.4 mmol; from step (ii) above) and Ph-(R)CH(OTBDMS)-C(O)OH (0.372 g; 1.4 mmol; prepared according to the method described in Hamada et al J. Am. Chem. Soc. (1989) 111, 669) yielding 288 mg (51%).

FAB-MS m/z 406 (M+1)⁺

¹H-NMR (500 MHz; CDCl₃): δ7.20–7.50 (m, 5 H), 5.25–5.70 (m, 2 H), 4.15–4.75 (m, 1H), 3.20–3.80 (m, 4 H), 2.00–2.90 (m, 3 H), 1.30–1.65 (m,1 H), 0.85–1.15 (m,9 H), 0.10–0.35 (m, 6 H).

(iv) Ph-(R)CH(OTBDMS)-C(O)—(R,S)Pic(4-oxo)-OH

A mixture of Ph-(R)CH(OTBDMS)-C(O)—(R,S)Pic(4-oxo)-OCH₃ (0.28 g; 0.69 mmol; from step (iii) above) and a solution of lithium hydroxide (2 M, 10 ml) in THF (10 ml) was stirred at room temperature for 1.5 h. The ThF was removed in vacuo, the residue was acidified (pH 2) with KHSO₄ (2 M) and extracted with EtOAc. The organic layer was washed with H₂O, dried (MgSO₄) and evaporated. The yield of the subtitle compound was 0.24 g (89%).

FAB-MS m/z 392 (M+1)⁺

¹H-NMR (400 MHz; CDCl₃): δ7.20–7.55 (m, 5 H), 5.15–5.75 (m, 2 H), 4.10–4.30 (m, 1 H), 3.20–3.80 (m, 1 H), 2.05–3.00 (m, 4 H), 1.35–1.55 (m, 1 H), 0.90–1.05 (m, 9 H), 0.10–0.25 (m, 6H).

(v) Ph-(R)CH(OTBDMS)-C(O)—(R,S)Pic(4-oxo)-Pab(Z)

The sub-title compound was prepared analogously to the method described in Example 1(ii) above from Ph-(R)CH(OTBDMS)-C(O)—(R,S)Pic(4oxo)-OH (0.227 g; 0.58 mmol; from step (iv) above) yielding 92 mg (24%).

FAB-MS m/z 657 (M+1)$^+$ $^1$H-NMR (500 MHz; CDCl$_3$): δ6.90–7.90 (m, 14 H), 5.10–5.80 (m, 4 H), 3.60–4.70 (m, 3 H), 2.10–3.20 (m, 4 H), 1.40–1.70 (m, 1 H), 0.80–1.10 (m, 9 H), 0.00–0.25 (m, 6 H).

(vi) Ph-(R)CH(OH)—C(O)—(R,S)Pic(4-oxo)-Pab(Z)

The sub-title compound was prepared analogously to the method described in step (ii) above from Ph-(R)CH(OTBDMS)-C(O)—(R,S)Pic(4-oxo)-Pab(Z) (0.09 g; 0.14 mmol; from step (v) above) yielding 61 mg (82%).

FAB-MS m/z 543 (M+1)$^+$ $^1$H-NMR (500 MHz; CDCl$_3$): δ6.95–7.90 (m, 14 H), 5.00–5.55 (m, 4 H), 3.95–4.70 (m, 2 H), 3.20–3.70 (m, 2 H), 1.20–2.80 (m, 4 H).

(vii) Ph-(R)CH(OH)—C(O)—(R,S)Pic(4oxo)-Pab×HOAc

The title compound was prepared according to the method described in Example 15(iii) above from Ph-(R)CH(OH)—C(O)—(R,S)Pic(4-oxo)-Pab(Z) (0.061 g; 0.11 mmol; from step (vi) above) yielding 46 mg (90%).

LC-MS m/z 407 (M–1)$^-$; 409 (M+1)$^+$ $^1$H-NMR (400 MHz; D$_2$O): δ7.20–7.85 (m, 9 H), 5.00–5.80 (m, 2 H), 4.35–4.55 (m, 2 H), 3.40–4.05 (m, 2 H), 1.80–3.10 (m, 4 H).

Example 58

Ph-(R)CH(OH)—C(O)—(R or S)Pic(4-methylene)-Pab×HOAc and Ph-(R)CH(OH)—C(O)—(S or R)Pic(4-methylene)-Pab×HOAc (i) Boc-(R,S)Pic(4-methylene)-OCH$_3$ Methyltriphenylphosphonium bromide (2.68 g; 7.5 mmol) was dried under vacuum for 20 minutes and was then suspended with dry THF (20 ml) at 0° C. Butyllithium (1.6 N in hexane; 4.7 ml; 7.5 mmol) was added dropwise and the mixture was stirred at room temperature for 30 minutes. The reaction mixture was cooled to –78° C. and Boc-(R,S)Pic(4-oxo)-OCH$_3$ (1.3 g; 5.0 mmol; see Example 57(i) above) was added. The reaction mixture was stirred at –78° C. for 30 minutes followed by 2 h at room temperature. Ammnonium chloride was added to the reaction mixture and after separation the H$_2$O-layer was extracted twice with diethyl ether. The combined organic layer was dried and evaporated to give a crude product which was purified by flash chromatography eluting with EtOAc:Hexane (30:70) to give 480 mg (37%) of the subtitle compound.

FAB-MS m/z 256 (M+1)$^+$ $^1$H NMR (500 MHz; CDCl$_3$): δ4.70–5.10 (m,3 H), 3.95–4.15 (m, 1 H) 3.70 (s, 3 H), 2.10–3.10 (m, 5 H), 1.35–1.60 (m, 9 H).

(ii) H—(R,S)Pic(4-methylene)-OCH$_3$

Boc-(R,S)Pic(4-methylene)-OCH$_3$ (0.48 g; 1.88 mmol; from step (i) above) was treated with trifluoroacetic acid (50% in CH$_2$Cl$_2$, 6 ml) at room temperature for 40 minutes. The reaction mixture was evaporated and the residue was dissolved in CH$_2$Cl$_2$, washed with Na$_2$CO$_3$ (saturated), dried (K$_2$CO$_3$) and evaporated. The yield of the sub-title compound was 0.27 g (95%).

$^1$H-NMR (500 MHz; CDCl$_3$): δ4.70–4.85 (m, 2 H), 3.75 (m, 3 H), 3.35–3.45 (m, 1 H), 3.15–3.25 (m, 1 H), 2.55–2.70 (m, 2 H), 2.10–2.30 (m, 3 H).

(iii) Ph-(R)CH(OTBDMS)-C(O)—(R,S)Pic(4-methylene)-OCH$_3$

The sub-title compound was prepared analogously to the method described in Example 3(ii) above from Ph-(R)CH(OTBDMS)-C(O)OH (0.37 g; 1.4 mmol; prepared according to the method described in Hamada et al J. Am. Chem. Soc. (1989) 111, 669) and H—(R,S)Pic(4-methylene)-OCH$_3$ (0.21 g; 1.4 mmol; from step (ii) above) yielding 0.283 g (52%).

FAB-MS m/z 404 (M+1)$^+$ $^1$H-NMR (500 MHz; CDCl$_3$): δ7.25–7.55 (m, 5 H), 5.15–5.70 (m, 2 H), 4.20–4.85 (m, 3 H), 3.65–3.75 (m, 3 H), 1.90–3.20 (m, 5 H), 0.90–1.10 (m, 9 H), 0.10–0.30 (m, 6 H).

(iv) Ph-(R)CH(OTBDMS)-C(O)—(R,S)Pic(4-methylene)-OH

The subtitle compound was prepared according to the method described in Example 57(iv) above from Ph-(R)CH(OTBDMS)-C(O)—(R,S)Pic(4-methylene)-OCH$_3$ (0.28 g; 0.69 mmol; from step (iii) above) yielding 0.24 g (89%).

FAB-MS m/z 390 (M+1)$^+$ $^1$H-NMR (500 MHz; CDCl$_3$): δ7.15–7.50 (m, 5 H), 5.15–5.95 (m, 2 H), 3.55–5.00 (m, 3 H), 1.75–3.25 (m, 5 H), 0.85–1.05 (m, 9 H), 0.10–0.25 (m, 6 H).

(v) Ph-(R)CH(OTBDMS)-C(O)—(R,S)Pic(4-methylene)-Pab(Z)

The sub-title compound was prepared analogously to the method described in Example 3(ii) above from Ph-(R)CH(OTBDMS)-C(O)—(R,S)Pic(4-methylene)-OH (0.235 g; 0.6 mmol; from step (iv) above) and H-Pab(Z)×HCl (0.211 g; 0.66 mmol) yielding 0.124 g (35%).

FAB-MS m/z 655 (M+1)$^+$ $^1$H-NMR (500 MHz; CDCl$_3$): δ7.10–7.90 (m, 14 H), 5.15–5.70 (m, 4 H), 4.10–5.05 (m, 4 H), 1.75–3.05 (m, 6 H), 0.80–1.10 (m, 9 H), 0.00–4.25 (m, 6H).

(vi) Ph-(R)CH((OH)—C(O)—(R,S)Pic(4-methylene)-Pab(Z)

The sub-title compound was prepared analogously to the method described in Example 57(vi) above from Ph-(R)CH(OTBDMS)-C(O)—(R,S)Pic(4-methylene)-Pab(Z) (0.08 g; 0.12 mmol; from step (v) above) yielding 0.06 g (91%).

LC-MS m/z 541 (M+1)$^+$ $^1$H-NMR (500 MHz; CD$_3$OD): δ7.15–7.90 (m, 14 H), 5.20–5.80 (m, 4 H), 4.35–4.90 (m, 4 H), 3.70–4.15 (m, 1 H), 3.20–3.40 (m, 1 H), 1.10–2.90 (m, 4 H).

(vii) Ph-(R)CH(OH)—C(O)—(R or S)Pic(4-methylene)-Pab×HOAc and Ph-(R)CH(OH)—C(O)—(S or R)Pic(4-methylene)-Pab×HOAc A mixture of Ph-(R)CH(OH)—C(O)—(R,S)Pic(4methylene)-Pab(Z) (0.035 g; 0.065 mmol; from step (vi) above), ammonium acetate (0.50 g, 7.4 mmol) and imidazole (0.20 g; 3.0 mmol) in methanol (5 ml) was stirred at 60° C. overnight. The reaction mixture was evaporated and the residue was subjected to preparative RPLC. Some fractions were concentrated to give 1.8 mg of compound 58B. Later fractions were concentrated to give 7 mg of compound 58A.

Compound 58A:

LC-MS m/z 405 (M–1)$^-$; 407 (M+1)$^+$ $^1$H-NMR (400 MHz; D$_2$O): δ7.15–7.80 (m, 9 H), 5.65–5.70 (m, 1 H), 4.80–5.25 (m, 1 H), 4.45–4.60 (m, 2 H), 3.60–4.00 (m, 2 H), 1.30–3.30 (m, 6 H).

Compound 58B:

LC-MS m/z 407 (M+1)$^+$ $^1$H-NMR (400 MHz; D$_2$O): δ7.30–7.80 (m, 9 H), 5.45–5.75 (m, 1 H), 4.80–5.20 (m, 1 H), 4.35–4.70 (m, 3 H), 3.75–3.90 (m, 1 H), 1.70–3.05 (m, 6 H).

Example 59

Ph(3-Cl)-(R,S)CH(OH)—C(O)-Aze-Pab×HOAc (i) (R,S)-3-Chloromandelic acid

The sub-title compound was prepared according to the method described in Example 15(i) above from 3-chlorobenzaldehyde (7.03 g; 50 mmol) yielding 2 g (21%).

LC-MS m/z 185 (M–1)$^-$, 370 (2M–1)$^-$ $^1$H NMR (400 MHz; CD$_3$OD): δ7.28–7.51 (m, 4 H), 5.14 (s, 1 H).

(ii) Ph(3-Cl)-(R,S)CH(OH)—C(O)-Aze-Pab(Z)

The sub-title compound was prepared according to the method described in Example 3(ii) above from (R,S)-3-chloromandelic acid (0.149 g; 0.8 mmol; from step (i) above) yielding 0.30 g (70%).

$^1$H-NMR (500 MHz; CDCl$_3$): δ7.08–7.84 (m, 13 H), 5.18–5.24 (m, 2 H), 4.86–5.01 (m, 2 H), 4.02–4.56 (m, 3 H), 3.57–3.76 (m, 1 H), 2.30–2.72 (m, 2 H).

(iii) Ph(3-Cl)-(R,S)CH(OH)—C(O)-Aze-Pab×HOAc

The title compound was prepared according to the method described in Example 43 above from Ph(3-Cl)-(R,S)CH(OH)—C(O)-Aze-Pab(Z) (0.10 g; 0.19 mmol; from step (ii) above) yielding 55 mg (63%).

LC-MS m/z 399 (M−1)$^-$, 401 (M+1)$^+$ $^1$H-NMR (400 MHz; D$_2$O): δ7.10–7.85 (m, 8 H), 4.82–5.37 (m, 2 H), 3.96–4.79 (m, 4 H), 2.14–2.85 (m, 2 H).

$^{13}$C NMR (100.6 MHz; D$_2$O; complicated due to diastereomers/rotamers) amidine and carbonyl carbons: δ174.00, 173.17, 172.83, 172.61, 166.59.

Example 60

Ph(3-Cl,4-OH)-(R,S)CH(OH)—C(O)-Pro-Pab×HCl
(i) Ph(3-Cl,4-OH)-(R,S)CH(OH)—C(O)-Pro-Pab(Z)

The sub-title compound was prepared according to the method described in Example 3(ii) above from (R,S)-3-chloro-4-hydroxymandelic acid (0.25 g; 1.23 mmol) and H-Pro-Pab(Z)×2HCl (0.615 g; 1.35 mmol; see Example 35(ii) above) yielding 382 mg (55%).

LC-MS m/z 564 (M−1)$^-$ $^1$H-NMR (400 MHz; CD$_3$OD): δ6.80–7.85 (m, 12 H), 5.16–5.25 (m, 3 H), 4.35–4.51 (m, 3 H), 3.45–3.75 (m, 1 H), 3.07–3.42 (m, 1 H), 1.72–2.18 (m, 4 H).

$^{13}$C NMR (100.6 CD$_3$OD; complicated due to diastereomers/rotamers) amidine and carbonyl carbons: δ174.62, 174.27, 173.02, 172.88, 170.41, 165.04.

(ii) Ph(3-Cl,4-OH)-(R,S)CH(OH)—C(O)-Pro-Pab×HCl

The title compound was prepared analogously to the method described in Example 43 above from Ph(3-Cl,4-OH)-(R,S)CH(OH)—C(O)-Pro-Pab(Z) (0.10 g; 0.177 mmol; from step (i) above), trifluoroacetic acid (3.7 ml; 48 mmol) and thioanisole (1.04 ml; 8.85 mmol) yielding 57 mg (70%).

LC-MS m/z 431 (M+1)$^+$ $^1$H NMR (500 MHz; D$_2$O): δ6.84–7.86 (m, 7 H), 5.29–5.42 (m, 1 H), 4.30–4.68 (m, 3 H), 3.05–4.05 (m, 2 H), 1.70–2.37 (m, 4 H).

Example 61

The title compounds of Examples 1 to 60 were tested in Test A above and were all found to exhibit an IC$_{50}$TT value of less than 0.3 μM.

Abbreviations
aq=aqueous
Aze=azetidine-2-carboxylic acid
Boc=tert-butyloxycarbonyl
Bn=benyl
Bu=butyl
Ch=cyclohexyl
DCC=dicyclohexylcarbodiimide
DIPEA=diisopropylethylamine
DMAP=N,N-dimethylaminopyridine
DMF=dimethylformamide
EDC=1-(3-dimethylaminopropyl)-3-ehtylcarbodiimide hydrochloride
Et=ethyl
EtOH=ethanol
h=hours
HCl=hydrochloric acid
HOAc=acetic acid
HOSu=N-hydroxysuccinimide
H-Dig=1-amidino-3-aminoethylazetidine
H-Dig(Z)=3-aminoethyl-1-(N-benzyloxycarbonylamidino)azetidine
H-Hig=1-amidino-3-aminoethylpyrrolidine
H-Hig(Z)=3-aminoethyl-1-(N-benzyloxycarbonylamidino)pyrrolidine
H-Pac=1-amidino-4-aminomethylcyclohexane
H-Pac(Z)=4-aminomethyl-1-(N-benzyloxycarbonylamidino)cyclohexane
H-Pic=pipecolinic acid
H-Pig=1-amidino-3-aminomethylpiperidine
H-Pig(Z)=3-aminomethyl-1-(N-benzyloxycarbonylamidino)piperidine
H-Pab=1-amidino-4-aminomethylbenzene
H-Pab(Z)=4-aminomethyl-1-(N-benzyloxycarbonylamidino)benzene
PCC=pyridinium chlorochromate
HPLC=high performance liquid chromatography
Me=methyl
Ph=phenyl
RPLC=reverse phase high performance liquid chromatography
Su=succinimide
TBDMS=tert-butyldimethylsilyl
TBTU=[N,N,N',N'-tetramethyl-O-(benzotriazol-1-yl) uronium tetrafluoroborate]
THF=tetrahydrofuran
THP=tetrahydropyranyl
TMS=trimethylsilyl
WSCI=water soluble carbodiimide
Z=benyloxycarbonyl Prefixes n, s, i and t have their usual meanings: normal, iso, secondary and tertiary. The stereochemistry for the amino acids is by default (S) if not otherwise stated

What is claimed is:

1. A compound of formula I, wherein p represents 0, 1, 2, 3 or 4;

q represents 0;

R$^1$ represents H,

R$^2$ represents H or C$_{1-4}$ alkyl (which latter group is optionally substituted or terminated by one or more hydroxy group)

R$^3$ represents C$_{3-8}$ cyclohexyl or phenyl (which latter two groups are optionally substituted by one or more of C$_{1-4}$ alkyl, C$_{1-4}$ alkoxy, halo, hydroxy, cyano, nitro, methylenedioxy, trifluoromethyl, N(H)R$^{27}$ or C(O)OR$^{28}$;

R$^{27}$ represents H, C$_{1-4}$ alkyl or C(O)R$^{29}$;

R$^{28}$ and R$^{29}$ independently represent H or C$_{1-4}$ alkyl;

R$^4$ represents H or C$_{1-4}$ alkyl;

Y represents CH$_2$ n represents 1, 2, 3 or 4; and

B represents a structural fragment of formula IVa

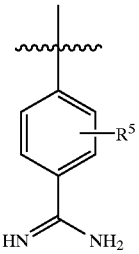

IVa wherein

R$^5$ represents H, halo or C$_{1-4}$ alkyl;

or a pharmaceutically acceptable salt thereof.

2. A compound as claimed in claim 1 wherein n represents 1.

3. A compound as claimed in claim 1 wherein R$^5$ represents H.

4. A compound as claimed in claim 1 wherein R$^4$ represents H.

5. A compound as claimed in claim 1 wherein p represents 0.

6. A compound as claimed in claim 1 wherein R$^2$ represents H, or optionally substituted C$_{1-4}$ alkyl.

7. A compound as claimed in claim 6 wherein, when R$^2$ represents optionally substituted C$_{1-4}$ alkyl, the hydroxy group is attached to the carbon atom which is α to the carbon atom to which OR$^1$ is attached.

8. A compound as claimed in claim 6 wherein R$^2$ represents H, methyl, hydroxymethyl or ethyl.

9. A compound as claimed in claim 1 wherein when R$^1$ and R$^2$ both represent H, R$^3$ represents unsubstituted phenyl or unsubstituted cyclohexyl.

10. A compound as claimed in claim 1 wherein R$^2$ represents methyl, hydroxymethyl or ethyl when R$^1$ represents H, and R$^3$ represents unsubstituted phenyl or unsubstituted cyclohexyl.

11. A compound as claimed in claim 1 wherein R$^3$ is substituted by one or more of hydroxy, fluoro, chloro, methyl, methoxy, amino, nitro, trifluoromethyl, methylenedioxy, ethoxy or propoxy, when it represents optionally substituted phenyl or optionally substituted cyclohexyl.

12. A compound as claimed in claim 11 wherein R$^3$ is substituted by one or more of hydroxy, mono- or difluoro, chloro, methyl, methoxy or methylenedioxy.

13. A compound as claimed in claim 1 wherein the α-amino acid carbon in the fragment

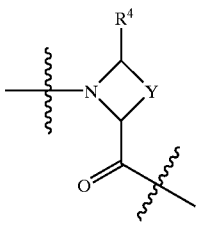

is in the S-configuration.

14. A compound as claimed in claim 1 wherein, when R$^1$ and R$^2$ both represent H and p represents 0, the α-carbon in the fragment

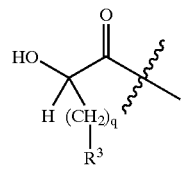

is in the R-configuration.

15. A compound as claimed in claim 1 which is selected from the group consisting of:

Ch-(R,S)CH(OH)—C(O)-Aze-Pab;
Ch-(R)(CH)(OH)—C(O)-Aze-Pab;
Ph-(R)CH(OH)—C(O)-Aze-Pab;
Ph(3-Me)-(R,S)CH(OH)—C(O)-Aze-Pab;
Ph(3-OMe)-(R,S)CH(OH)—C(O)-Aze-Pab;
Ph(3,5-diOMe)-(R,S)CH(OH)—C(O)-Aze-Pab;
Ph(3-OMe,4-OH)—(R,S)CH(OH)—C(O)-Aze-Pab;
Ph-(R,S)C(Et)(OH)—C(O)-Aze-Pab;
Ph(3,4-(—O—CH$_2$—O—))—(R,S)CH(OH)—C(O)-Aze-Pab;
Ph-(R,S)C(Me)(OH)—C(O)-Aze-Pab;
Ph(3,5-diMe)-(R,S)CH(OH)—C(O)-Aze-Pab;
Ph(3-NH$_2$)—(R,S)CH(OH)—C(O)-Aze-Pab;
Ph(3-Cl)—(R,S)CH(OH)—C(O)-Aze-Pab; and
Ph-(R,S)C(CH$_2$OH)(OH)—C(O)-Aze-Pab.

16. A pharmaceutical composition comprising a compound as defined in claim 1, or a pharmaceutically-acceptable salt thereof, in admixture with a pharmaceutically-acceptable adjuvant, diluent or carrier.

17. A compound as claimed in claim 1, wherein R$^3$ represents phenyl substituted by one or more substituents selected from the group consisting of N(H)R$^{23}$ and halogen.

18. A compound as claimed in claim 1, wherein R$^3$ represents phenyl substituted by N(H)R$^{23}$ and halogen.

19. A compound as claimed in claim 18, wherein R$^3$ represents phenyl substituted by N(H)R$^{23}$ and chloro.

* * * * *

UNITED STATES PATENT AND TRADEMARK OFFICE
CERTIFICATE OF CORRECTION

PATENT NO.     : 6,617,320 B2
DATED          : Septemeber 9, 2003
INVENTOR(S)    : Gustafsson et al It is certified that error appears in the above-identified patent and that said Letters Patent is hereby corrected as shown below:

Column 1,
Line 32, please delete "crossinks" and insert -- crosslinks --
Line 52, please delete "P9-2-P1" and insert -- P9-P2-P1 --;
Line 63, please delete "bennamidines" and insert -- benzamidines --;

Column 2,
Line 22, please delete "fluoroalkylaride" and insert -- fluoroalkylamide --;
Line 41, please delete "thiombin" and insert -- thrombin --;

Column 3,
Line 46, please delete "group) is" and insert -- group is --;

Column 4,
Line 59, please delete "factional" and insert -- fractional --;

Column 5,
Line 43, please delete "a" and insert -- $\alpha$ --;

Column 6,
Line 23, please delete "carbon" and insert -- $\alpha$-carbon --;

Column 8,
Line 2, please "$C_{1-4}$ ally" and insert -- $C_{1-4}$ alkyl --;

Column 9,
Line 45, please delete "theater" and insert -- thereafter --;

Column 11,
Line 2, please delete "usefull" and insert -- useful --;
Line 21, please delete "angioplast" and insert -- angioplasty --;
Line 59, please delete "subcutaneously buccally" and insert -- subcutaneously, buccally --;
Line 63, please delete "pharmaceutical" and insert -- pharmaceutically --;

Column 13,
Line 52, please delete "Mhz" and insert -- MHz --;

Column 14,
Line 3, please delete "Bo-Aze-Pab(Z)" and insert -- Boc-Aze-Pab(Z);
Line 24, please delete "vacua" and insert -- vacuo --;

UNITED STATES PATENT AND TRADEMARK OFFICE
CERTIFICATE OF CORRECTION

PATENT NO. : 6,617,320 B2
DATED : Septemeber 9, 2003
INVENTOR(S) : Gustafsson et al It is certified that error appears in the above-identified patent and that said Letters Patent is hereby corrected as shown below:

Column 15,
Line 15, please delete "diastreomers" and insert -- diastereomers --;
Line 15, pelase delete "δ1763" and insert -- δ176.3 --;
Line 52, please delete "stired" and insert -- stirred --;
Line 62, please delete "0.9-4.75"and insert -- 0.9-0.75 --;

Column 16,
Line 43, please delete "n" and insert -- m --;
Line 60, please delete "diasteomers" and insert -- diastereomers --;

Column 17,
Line 5, please delete "2H," (first occurrence) and insert -- 2H), --
Line 20, please delete "freezered" and insert -- freeze-dried --;
Line 51, please delete, "crystaline" and insert -- crystalline --;
Line 60, please delete "diastermers" and insert -- diastereomers --;

Column 18,
Line 27, please delete "anidine" and insert -- amidine --;
Line 42, please delete "diastreomersrotamers" and insert -- diastereomers/rotamers --;
Line 54, please delete "1H)" and insert -- 1H --;

Column 19,
Line 31, please delete "br" (first occurrence) and insert -- (br --;
Line 43, please delete "236" and insert -- 2.36 --;

Column 20,
Line 34, please delete "143" and insert -- 1.43 --;

Column 22,
Line 23, please delete "diastoeomers" and insert -- diastereomers --;
Line 30, please delete "sired" and insert -- stirred --;

Column 30,
Line 14, please delete "(ii)" and insert -- (iii) --;
Line 34, please delete "Shiman" and insert -- Shuman --;

UNITED STATES PATENT AND TRADEMARK OFFICE
CERTIFICATE OF CORRECTION

PATENT NO. : 6,617,320 B2
DATED : Septemeber 9, 2003
INVENTOR(S) : Gustafsson et al It is certified that error appears in the above-identified patent and that said Letters Patent is hereby corrected as shown below:

Column 32,
Line 59, please delete "froms" and insert -- from --;

Column 34,
Line 34, please delete "3.28" and insert -- 3.38 --;

Column 35,
Line 29, please delete "carbonly" and insert -- carbonyl --;

Column 40,
Line 6, please delete "is".
Line 43, please delete "85,mg" and insert -- 85 mg --;

Column 41,
Lines 2 and 3, please delete "Ph-(S or R)C(-O-C(CH$_3$)$_2$-C(O)-Aze-PabxHOAc" and insert -- Ph-(S or R)C(-O-C(CH$_3$)$_2$-O-CH$_2$-)-C(O)-Aze-PabxHOAc --.
Line 23, please delete "Ph-(R or S)C(-O-C(CH$_3$)$_2$-O-CH$_2$-C(O)-Aze-PabxHOAc" and insert -- Ph-(R or S)C(-O-C(CH$_3$)$_2$-O-CH$_2$)-C(O)-Aze-PabxHOAc --;
Line 60, please delete "vacua" and insert -- vacuo --;

Column 42,
Lines 28-29, please delete "Ph-(R,S)C(-O-C(CH$_3$)$_2$-CH$_2$-)-C(O)-Pro-Pab(Z)" and insert -- Ph-(R,S)C(-O-C(CH$_3$)$_2$-O-CH$_2$-)-C(O)-Pro-Pab(Z)"
Lines 54-55, please delete "Ph-(R or S)C(-O-C-CH$_3$)$_2$-O-CH$_2$-C(O)-Pro-PabxHOAc" and insert -- Ph-(R or S)C(-O-C(CH$_3$)$_2$-O-CH$_2$-)C(O)-Pro-PabxHOAc --;

Column 43,
Line 10, please delete "ir" and insert -- in --;
Line 28, please delete "53" and insert -- 55 --;
Line 44, please delete "is";

Column 44,
Line 8, please delete "diastereomerslrotamers" and insert -- diastereomers/rotamers --;
Line 53, please delete "ThF" and insert -- THF --;
Line 66, please delete "4oxo" and inert -- 4-oxo --;

UNITED STATES PATENT AND TRADEMARK OFFICE
CERTIFICATE OF CORRECTION

PATENT NO.     : 6,617,320 B2
DATED          : Septemeber 9, 2003
INVENTOR(S)    : Gustafsson et al It is certified that error appears in the above-identified patent and that said Letters Patent is hereby corrected as shown below:

Column 45,
Line 38, please delete "Ammnonium" and insert -- Ammonium --;

Column 46,
Line 25, please delete "0.00-4.25" and insert -- 0.00-0.25 --;
Line 26, please delete "CH((OH)" and insert -- CH(OH) --;
Line 40, please delete "4methylene" and insert -- 4-methylene --;

Column 47,
Line 64, please delete "-3-ehtylcarbodiimide" and insert -- -3-ethylcarbodiimide --;

Column 48,
Line 35, please delete "benyloxycarbonyl" and insert -- benzyloxycarbonyl --;
Line 59, please delete "cyclohexyl" and insert -- cycloalkyl --;

Signed and Sealed this

Seventeenth Day of August, 2004

JON W. DUDAS
*Acting Director of the United States Patent and Trademark Office*